United States Patent
Woodard, Jr. et al.

(10) Patent No.: US 9,451,946 B2
(45) Date of Patent: Sep. 27, 2016

(54) LAPAROSCOPIC SUTURING INSTRUMENT WITH PARALLEL CONCENTRIC SHAFT PAIRS

(75) Inventors: James A. Woodard, Jr., Mason, OH (US); Aaron J. Brickner, Milford, OH (US); Jason R. Lesko, Harrison, OH (US); William J. White, West Chester, OH (US); David T. Martin, Milford, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 120 days.

(21) Appl. No.: 13/449,494

(22) Filed: Apr. 18, 2012

(65) Prior Publication Data
US 2013/0282027 A1 Oct. 24, 2013

(51) Int. Cl.
*A61B 17/04* (2006.01)
*A61B 17/062* (2006.01)
*A61B 17/06* (2006.01)

(52) U.S. Cl.
CPC ....... *A61B 17/0469* (2013.01); *A61B 17/0491* (2013.01); *A61B 17/0625* (2013.01); *A61B 2017/061* (2013.01); *A61B 2017/0608* (2013.01)

(58) Field of Classification Search
CPC .......... A61B 17/0469; A61B 17/0625; A61B 2017/2912; A61B 17/7007; A61B 17/8057; A61B 2017/044; A61B 17/0491; A61B 2017/0608; A61B 2017/061
USPC .......... 606/144, 139, 147, 271, 264
See application file for complete search history.

(56) References Cited

U.S. PATENT DOCUMENTS

| | | | |
|---|---|---|---|
| 5,954,731 A * | 9/1999 | Yoon | 606/144 |
| 6,056,771 A | 5/2000 | Proto | |
| 6,071,289 A * | 6/2000 | Stefanchik et al. | 606/147 |
| 6,159,224 A * | 12/2000 | Yoon | 606/147 |
| 6,206,894 B1 | 3/2001 | Thompson et al. | |
| 6,224,614 B1 | 5/2001 | Yoon | |
| 7,628,796 B2 | 12/2009 | Shelton, IV et al. | |

(Continued)

FOREIGN PATENT DOCUMENTS

WO WO 98/48705 11/1998
WO WO 2012/068002 5/2012

OTHER PUBLICATIONS

International Search Report and Written Opinion dated Aug. 6, 2013 for Application No. PCT/US2013/036752.
U.S. Appl. No. 61/355,832, filed Jun. 17, 2010.
U.S. Appl. No. 61/413,680, filed Nov. 15, 2010.
US Office Action, Non-Final, dated Dec. 17, 2013 for U.S. Appl. No. 13/449,514, 14 pages.

(Continued)

*Primary Examiner* — Katrina Stransky
(74) *Attorney, Agent, or Firm* — Frost Brown Todd LLC

(57) ABSTRACT

A suture needle driving instrument comprises a shaft assembly, an end effector, and a grasping actuation assembly. The end effector is located at the distal end of the shaft assembly and includes a pair of grasping arms. Each grasping arm comprises a respective pair of jaws. Each pair of jaws is operable to cooperate to grasp and release a suture needle. The grasping actuation assembly is operable to drive one jaw of each pair in one direction while simultaneously driving the other jaw of the pair in an opposite direction, to selectively grasp or release the suture needle. The shaft assembly includes two pairs of parallel concentric shafts, which form part of the actuation assembly. Each shaft pair is operable to drive a respective internal drive shaft having separate threaded regions with opposing pitch. The instrument may be used through a trocar during minimally invasive surgery.

20 Claims, 78 Drawing Sheets

(56) References Cited

U.S. PATENT DOCUMENTS

| | | | |
|---|---|---|---|
| 7,666,196 B1* | 2/2010 | Miles | 606/144 |
| 8,137,339 B2 | 3/2012 | Jinno et al. | |
| 2007/0225754 A1 | 9/2007 | Measamer et al. | |
| 2010/0100125 A1 | 4/2010 | Mahadevan | |
| 2011/0313433 A1 | 12/2011 | Woodard, Jr. et al. | |
| 2012/0123471 A1 | 5/2012 | Woodard, Jr. et al. | |
| 2012/0150199 A1 | 6/2012 | Woodard, Jr. et al. | |
| 2013/0282031 A1 | 10/2013 | Woodard, Jr. et al. | |

OTHER PUBLICATIONS

US Office Action, Final, dated Jul. 2, 2014 for U.S. Appl. No. 13/449,514, 11 pages.
US Office Action, Non-Final, dated Feb. 5, 2015 for U.S. Appl. No. 13/449,514, 13 pages.
US Office Action, Non-Final, dated Dec. 10, 2015 for U.S. Appl. No. 13/449,514, 8 pages.

* cited by examiner

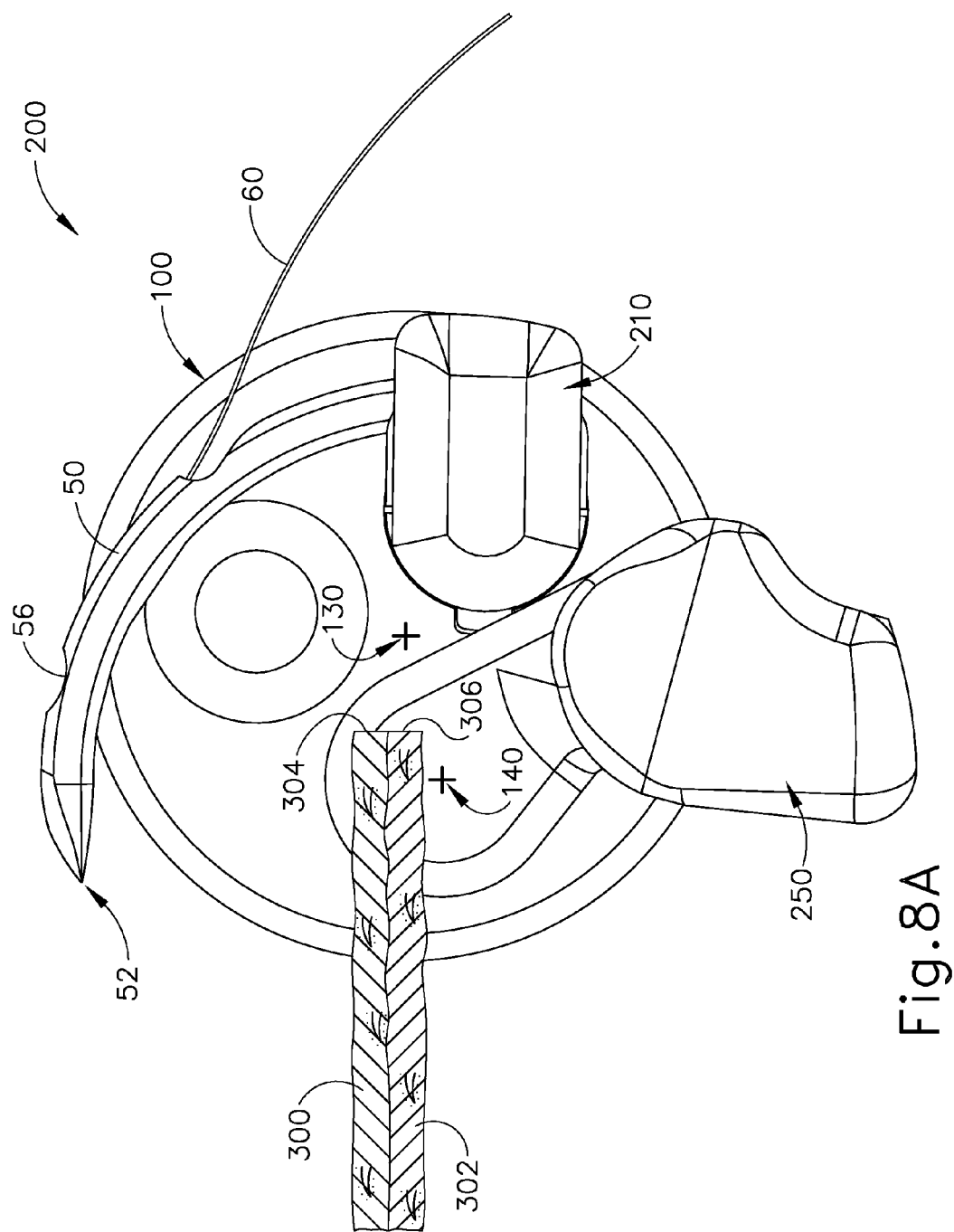

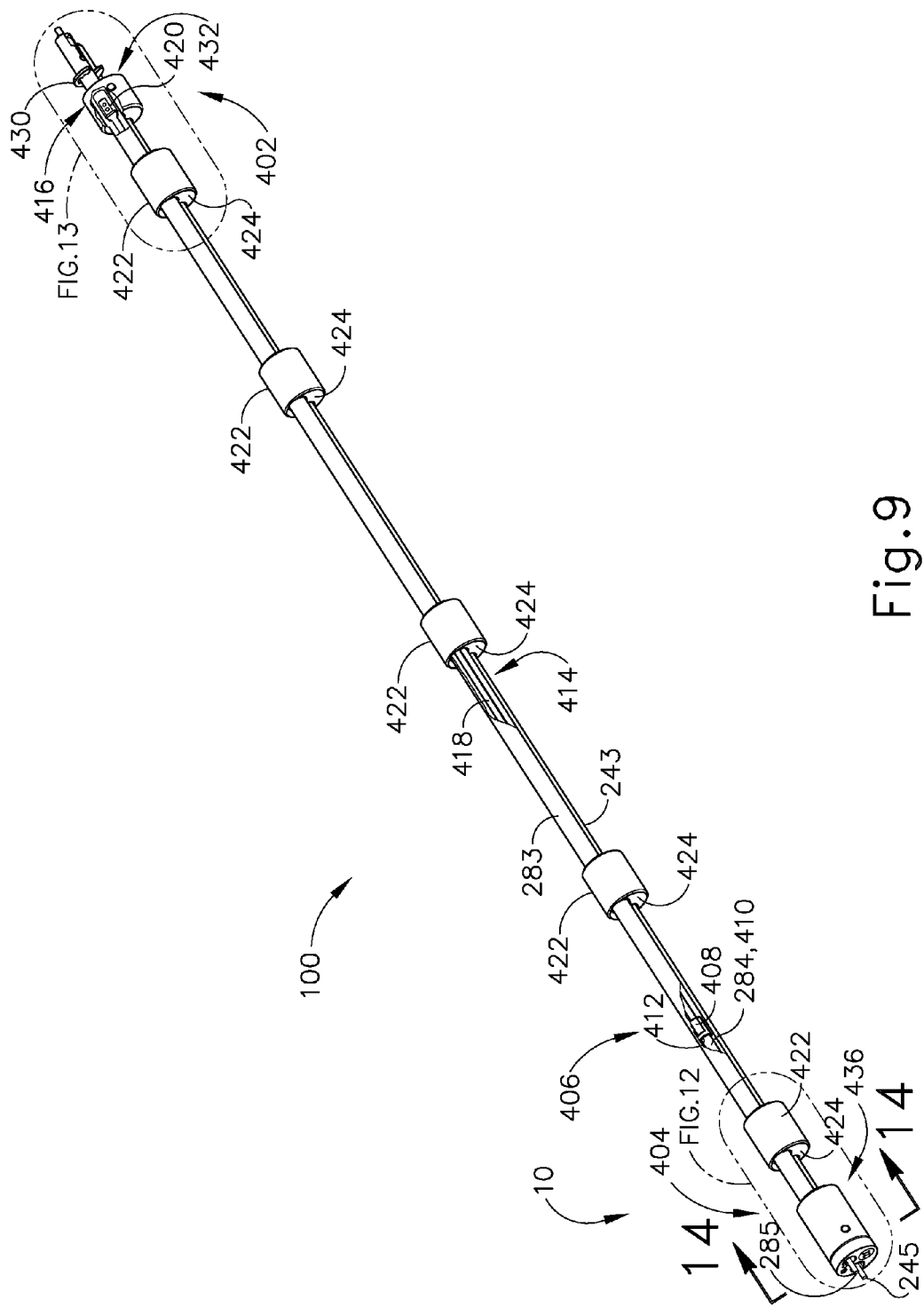

LAPAROSCOPIC SUTURING INSTRUMENT WITH PARALLEL CONCENTRIC SHAFT PAIRS

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparoscopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio. Additional suturing instruments are disclosed in U.S. Pat. No. 7,628,796, entitled "Surgical Suturing Apparatus with Anti-Backup System," issued Dec. 8, 2009, the disclosure of which is incorporated by reference herein; U.S. Pat. No. 6,071,289, entitled "Surgical Device for Suturing Tissue," issued Jun. 6, 2000, the disclosure of which is incorporated by reference herein; U.S. Pub. No. 2011/0313433, entitled "Laparoscopic Suture Device with Asynchronous In-Line Needle Movement," filed Jun. 9, 2011, now U.S. Pat. No. 9,186,037, issued Oct. 27, 2015, the disclosure of which is incorporated by reference herein; and U.S. Provisional Patent Application No. 61/355,832, entitled "Laparoscopic Suture Device," filed Jun. 17, 2010, the disclosure of which is incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; U.S. Pub. No. 2010/0100125, entitled "Suture Needle and Suture Assembly," published Apr. 22, 2010, the disclosure of which is incorporated by reference herein; U.S. Provisional Application Ser. No. 61/413,680, filed Nov. 15, 2010, entitled "Custom Needle for Suture Instrument," the disclosure of which is incorporated by reference herein; U.S. patent application Ser. No. 13/295,186, entitled "Needle for Laparoscopic Suturing Instrument," filed on Nov. 14, 2011, now U.S. Pat. No. 9,125,646, issued Sep. 8, 2015, the disclosure of which is incorporated by reference herein; and U.S. patent application Ser. No. 13/295,203, entitled "Laparoscopic Suturing Instrument with Dual-Action Needle Graspers," filed on Nov. 14, 2011, now U.S. Pat. No. 8,702,732, issued Apr. 22, 2014, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8A depicts an end view of the end effector and needle of FIG. 2A, during an exemplary first stage of operation;

FIG. 9 depicts a fragmented, perspective view of the shaft assembly of the suturing instrument of FIG. 1 without the outer sheath;

Figure 1:
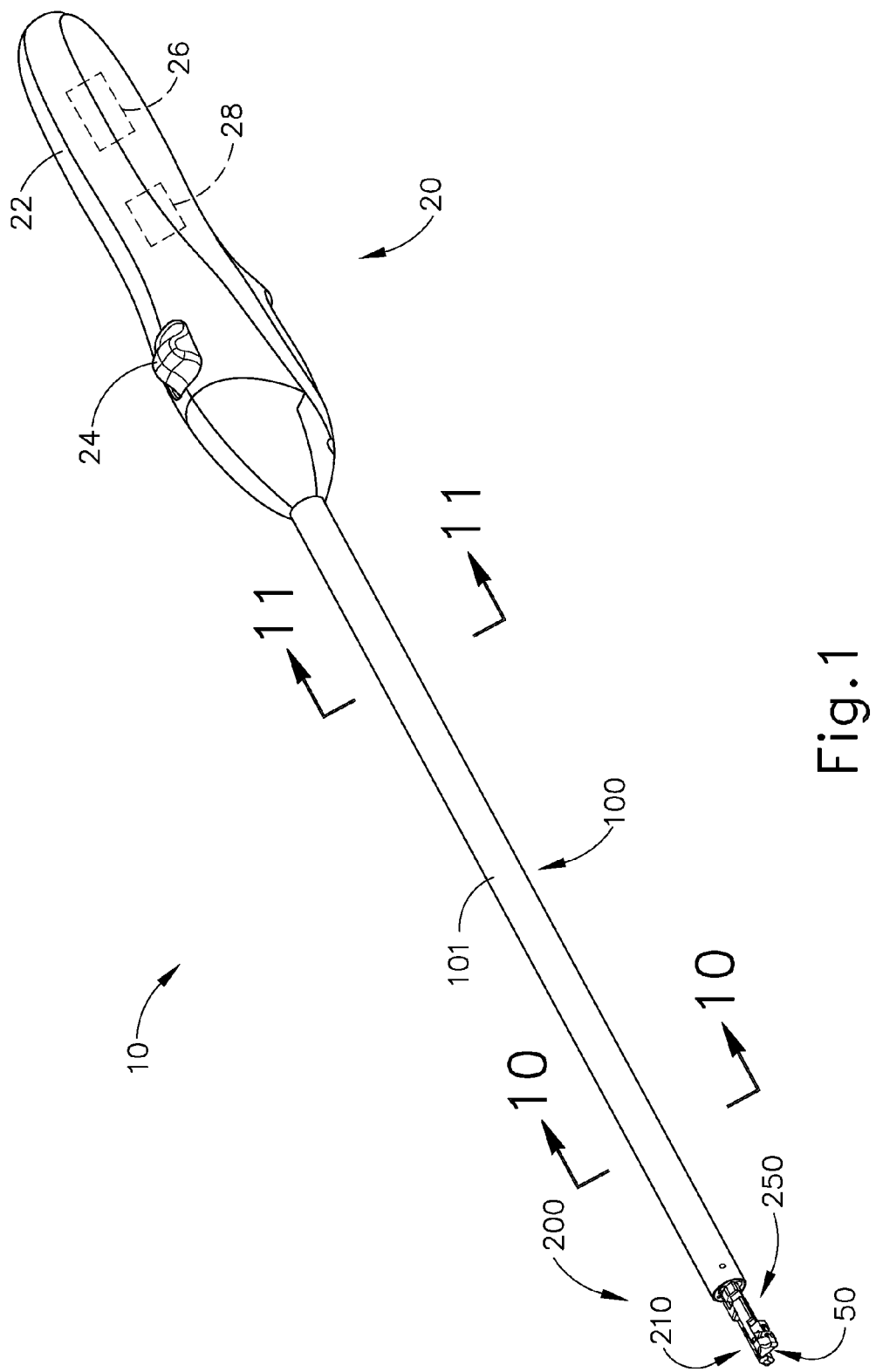
FIG. 1 depicts a perspective view of an exemplary laparoscopic suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview

FIG. 1 shows an exemplary laparoscopic suturing instrument (10). Instrument (10) of this example includes a handle portion (20), a shaft assembly (100) extending distally from handle portion (20), and an end effector (200) at the distal end of shaft assembly (100). Handle portion (20) includes a grip (22), a rocker (24), an integral power source (26), and a motor (28) in communication with the integral power source (26). Rocker (24) is resiliently biased to a generally vertical position (e.g., generally perpendicular to grip (22)), though rocker (24) may be rocked forwardly or rearwardly. In addition or in the alternative, rocker (24) may be rocked to the left or to the right. Rocker (24) is operable to actuate features of end effector (200) as will be described in greater detail below. Of course, rocker (24) is merely one example of a user input feature, and any other suitable type of user input feature may be used.

Integral power source (26) comprises a rechargeable battery in the present example, though it should be understood that any other suitable power source may be used. By way of example only, instrument (10) may use a power source that is external to instrument (10) (e.g., coupled with instrument (10) via a cable, etc.). Similarly, while end effector (200) is powered by motor (28) in the present example, it should be understood that any other suitable source may be used, including but not limited to a manually operable mechanism. Various other suitable components, features, and configurations for handle portion (20) will be apparent to those of ordinary skill in the art in view of the teachings herein. By way of example only, handle portion (20) may be constructed in accordance with at least some of the teachings of U.S. Provisional Patent Application No. 61/355,832, the disclosure of which is incorporated by reference herein; and/or in accordance with at least some of the teachings of U.S. Patent Application No. 2011/0313433, now U.S. Pat. No. 9,186,037, the disclosure of which is incorporated by reference herein.

Shaft assembly (100) of the present example has an outer diameter sized to permit shaft assembly (100) to be inserted through a conventional trocar (not shown). Shaft assembly (100) also has a length sized to permit end effector (200) to be positioned at a surgical site within a patient while also allowing handle portion (20) to be manipulated by a user (e.g., a surgeon) from a location outside the patient when shaft assembly (100) is disposed in a trocar. Of course, shaft assembly (100) need not necessarily be dimensioned for use through a trocar. For instance, instrument (10) may be used and/or configured for use in open surgical procedures.

In some versions, shaft assembly (100) includes one or more articulating features, allowing end effector (200) to be articulated to various angles and positions relative to the longitudinal axis defined by shaft assembly (100). Merely illustrative examples of such articulation are taught in U.S. Provisional Application Ser. No. 61/355,832, the disclosure of which is incorporated by reference herein. Various other suitable ways in which articulation may be provided will be apparent to those of ordinary skill in the art in view of the teachings herein. In addition or in the alternative, shaft assembly (100) may be rotatable about the longitudinal axis, relative to handle portion (20), to selectively position end effector (200) at various angular orientations about the longitudinal axis. Of course, a user may rotate the entire instrument (10) about the longitudinal axis to selectively position end effector (200) at various angular orientations about the longitudinal axis.

End effector (200) of the present example includes a first grasping arm (210) and a second grasping arm (250). As will be described in greater detail below, arms (210, 250) are configured to alternatingly throw and catch a curved suturing needle (50) along a path/plane that is substantially perpendicular to the longitudinal axis defined by shaft assembly (100). Alternatively, arms (210, 250) may be configured to alternatingly throw and catch needle (50) along a path that is substantially parallel to the longitudinal axis defined by shaft assembly (100); or along some other path.

In some versions, arms (210, 250) pass needle (50) back and forth from arm (42) to arm (210) and from arm (250) to arm (210) in an oscillating motion (i.e., back and forth in opposite directions), such that needle (50) does not traverse a circular path as needle (50) is being passed between arms (210, 250). Such action of needle (50) may be referred to as a "reverse reset." In some other versions, needle (50) may be passed between arms (210, 250) along a circular path in a single direction. Such action of needle (50) may be referred to as a "forward reset." By way of example only, arms (210, 250) may move in accordance with at least some of the teachings of U.S. Provisional Patent Application No. 61/355,832, the disclosure of which is incorporated by reference herein; and/or in accordance with at least some of the teachings of U.S. Patent Application No. 2011/0313433, now U.S. Pat. No. 9,186,037, the disclosure of which is incorporated by reference herein. Regardless of whether arms (210, 250) move synchronously or asynchronously, arms (210, 250) may be configured to grip and/or compress tissue that is positioned between arms (210, 250) when arms are in approximated positions, which may facilitate passage of needle (50) through the tissue.

As shown in FIGS. 3A and 3C, needle (50) of this example includes a sharp tip (52), a blunt end (54), and a pair of grasping regions (56, 58) configured for grasping by arms (210, 250). In particular, grasping regions (56, 58) comprise scallops in the present example, though it should be understood that grasping regions (56, 58) may have various other configurations. A suture (60), shown in FIG. 8A, is secured to a mid-region of needle (50). The configuration and relationship of suture (60) and needle (50) provides an exit of suture (60) from needle (50) at an angle that is generally tangent to or oblique relative to the curvature of needle (50). Such an angle may provide reduced drag forces and/or reduced tissue trauma as compared to drag forces and/or tissue trauma that might otherwise be encountered using a needle with a suture that exits at a generally perpendicular angle.

While the example described below includes just a single strand of suture extending from the needle, it should be understood that two or more strands may extend from the needle (e.g., double leg suture, etc.). As yet another merely illustrative example, suture (60) may be secured to blunt end (54) of needle (50) instead of being secured to a mid-region of needle (50). In still other versions, end (54) includes a sharp tip instead of being blunt. It should also be understood that needle (50) may be straight instead of curved in some versions. By way of example only, needle (50) may be constructed in accordance with at least some of the teachings of U.S. Provisional Application Ser. No. 61/413,680; U.S. patent application Ser. Nos. 13/295,186, now U.S. Pat. No. 9,125,646 and 13/295,203, now U.S. Pat. No. 8,702,732; U.S. Pat. No. 6,056,771; and/or U.S. Pub. No. 2010/0100125. Still other suitable configurations for needle (50) will be apparent to those of ordinary skill in the art in view of the teachings herein.

It should also be understood that needle (50) may be constructed using various techniques. By way of example only, needle (50) may be constructed using metal-injection-molding (MIM) processes. Needle (50) may also be formed from a sheet, wire, tube, extrusion, or other components that are bent, stamped, coined, milled, otherwise machined, and/or otherwise formed. Other suitable ways in which needle (50) may be constructed will be apparent to those of ordinary skill in the art in view of the teachings herein.

II. Exemplary End Effector

As noted above, end effector (200) comprises a pair of grasping arms (210, 250) that are operable to selectively grasp needle (50) during a suturing procedure. Grasping arms (210, 250) are exposed relative to an endcap (102) of shaft assembly (100). Each grasping arm (210, 250) extends along a respective axis that is parallel to yet offset from the center axis of shaft assembly (100). First grasping arm (210) maintains a fixed rotational position relative to shaft assembly (100) during operation of instrument (10) in the present example. In some other versions, first grasping arm (210) is rotatable about its own longitudinal axis, relative to shaft assembly (100). Second grasping arm (250) of the present example is rotatable about its longitudinal axis. Such motion can be seen in the series shown by FIGS. 2A-2C.

Figure 2A:
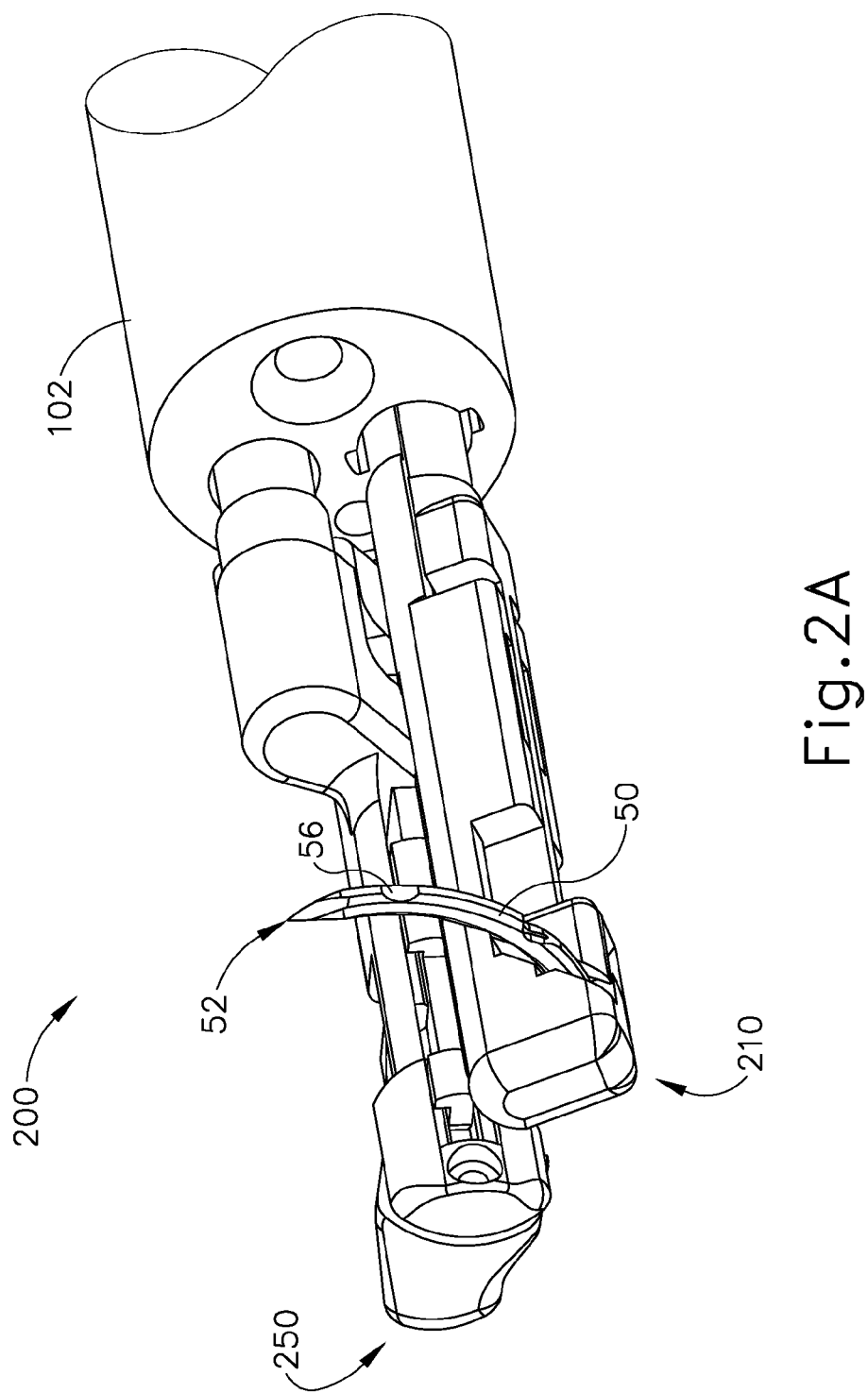
FIG. 2A depicts a perspective view of the end effector of the suturing instrument of FIG. 1 and a needle in a first operational configuration.
Figure 2B:
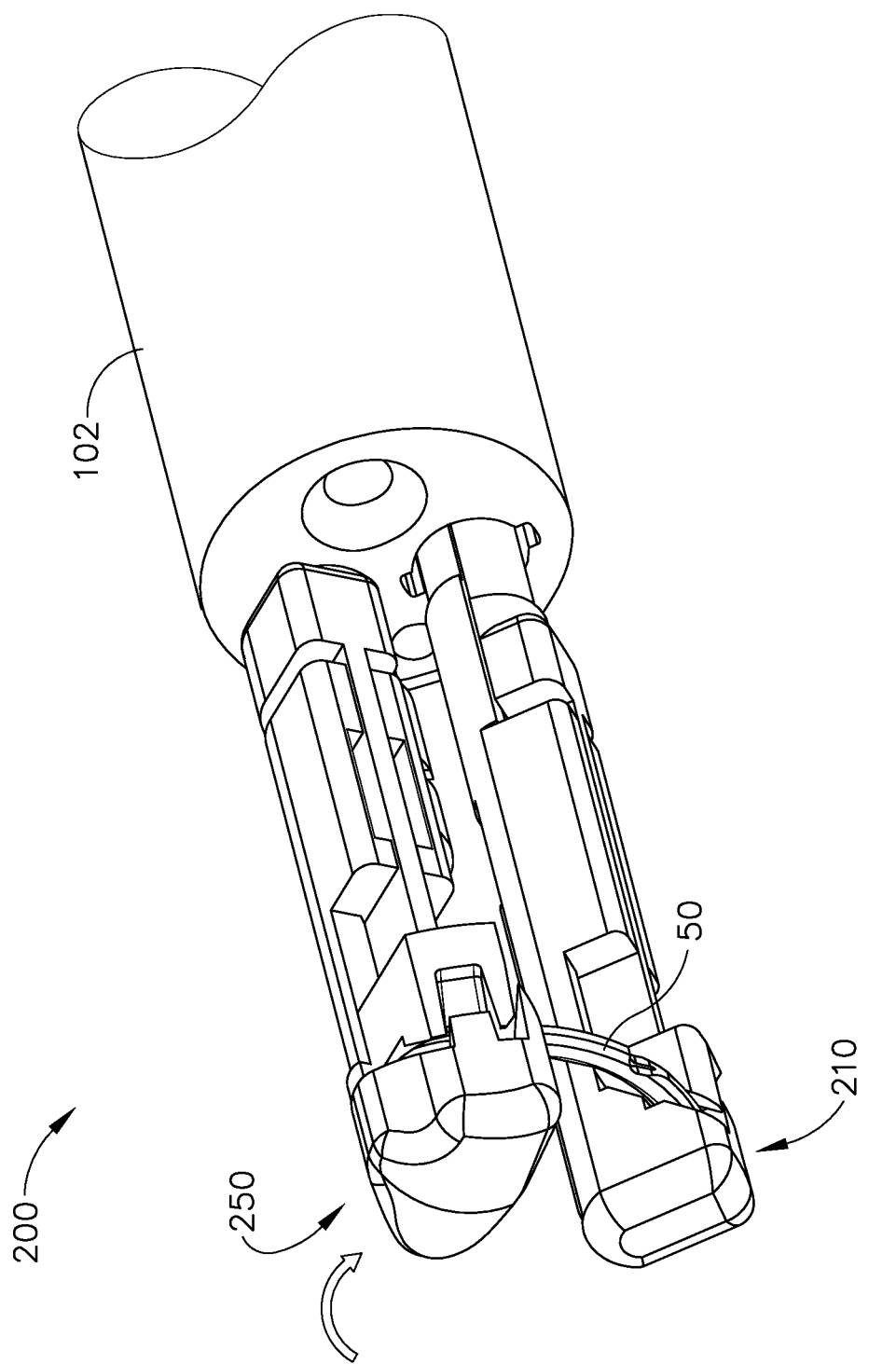
FIG. 2B depicts a perspective view of the end effector and needle of FIG. 2A, in a second operational configuration.
Figure 2C:
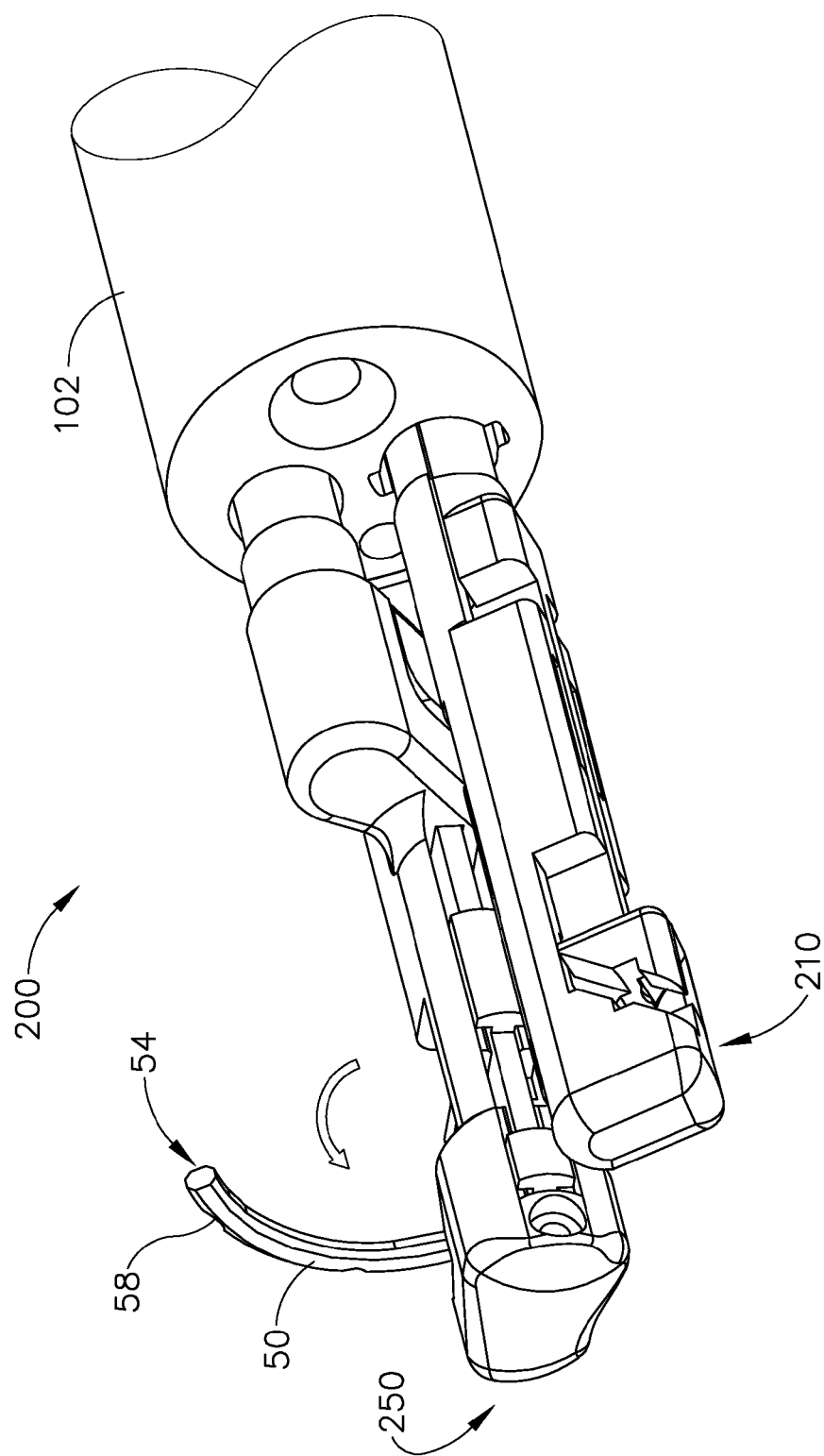
FIG. 2C depicts a perspective view of the end effector and needle of FIG. 2A, in a third operational configuration.

FIG. 2A shows first grasping arm (210) grasping needle (50), with second grasping arm (250) rotated away from needle (50), exposing sharp tip (52) of needle (50). FIG. 2B shows second grasping arm (250) rotated toward needle (50) to a position enabling second grasping arm (250) to grasp needle (50) and first grasping arm (210) to release needle (50). FIG. 2C shows second grasping arm (250) rotated away from first grasping arm (210), pulling needle (50) away from second grasping arm (250). After reaching this position, second grasping arm (250) may be rotated back to the position shown in FIG. 2B, to thereby pass needle (50) back to first grasping arm (210); then rotate back to the position shown in FIG. 2A to start the cycle over again.

In the examples described herein, needle (50) is driven along a plane that is substantially perpendicular to the longitudinal axis of shaft assembly (100). In some other examples, needle (50) is driven along a plane that is oblique relative to the longitudinal axis of shaft assembly (100) or substantially parallel to the longitudinal axis of shaft assembly (100). During some uses of instrument (10), needle (50)

may deviate from the desired perpendicular plane. Such deviation may be due to manufacturing tolerances, deflections caused by tissue or other structures, and/or for other reasons. Such deviation may be accentuated by using a needle (50) having a relatively great length. As will be described below, end effector (200) of the present example is configured to readily accommodate and correct such off-plane deviations. In other words, arms (210, 250) are operable to grasp needle (50) even in instances where needle (50) has deviated away from the expected perpendicular plane of motion; and arms (210, 250) are further operable to redirect a deviated needle (50) back onto the expected perpendicular plane of motion.

It should be noted that suture (60) is omitted from FIGS. 2A-2C for clarity. Various components of grasping arms (210, 250) will be described in greater detail below. Various ways in which grasping arms (210, 250) may be used will also be described in greater detail below. Other suitable components of and uses for grasping arms (210, 250) will be apparent to those of ordinary skill in the art in view of the teachings herein.

A. Exemplary First Grasping Arm

Figure 3:
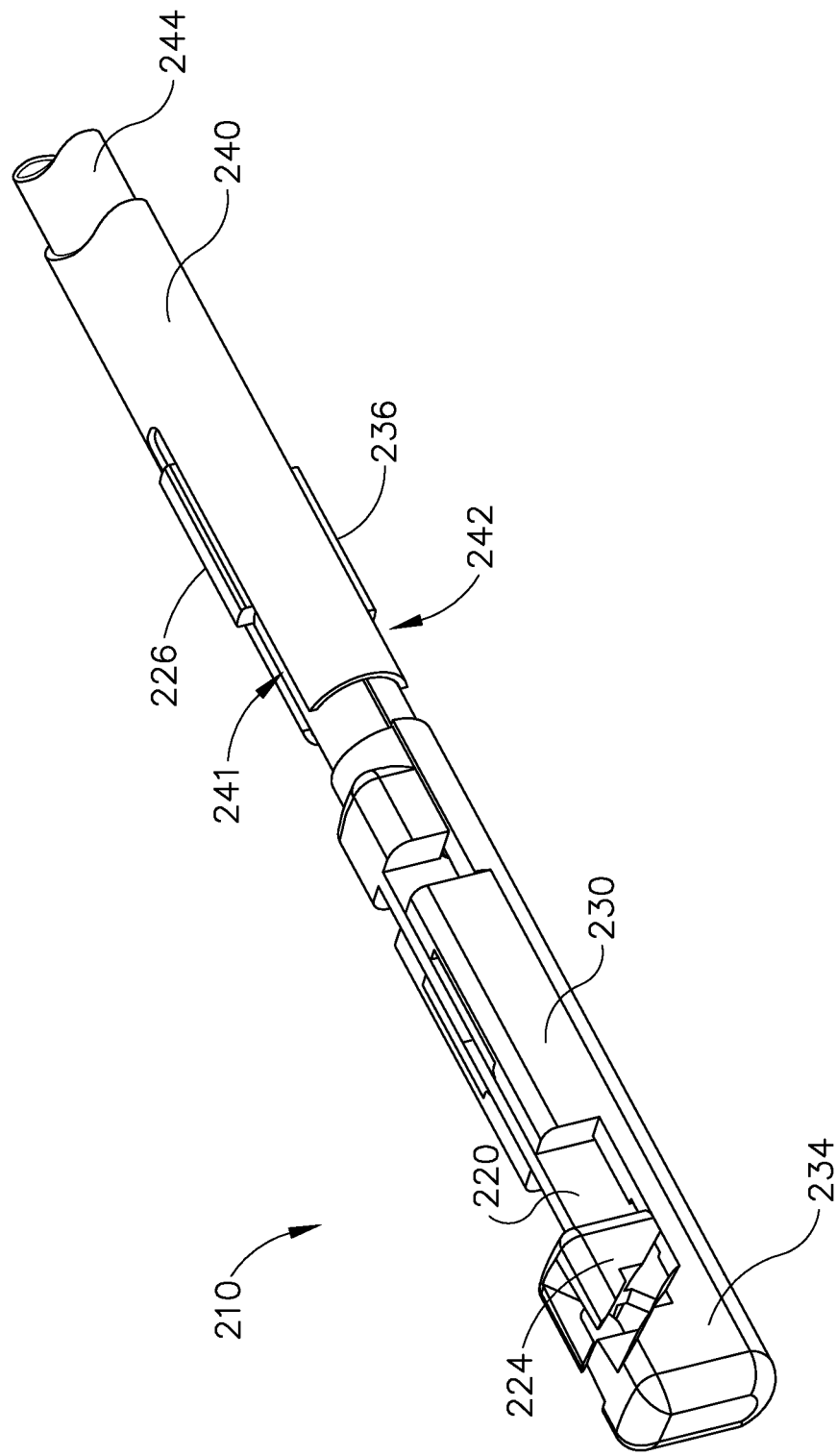
FIG. 3 depicts a first partial perspective view of a first needle grasping arm of the end effector of FIG. 2A.
Figure 4A:
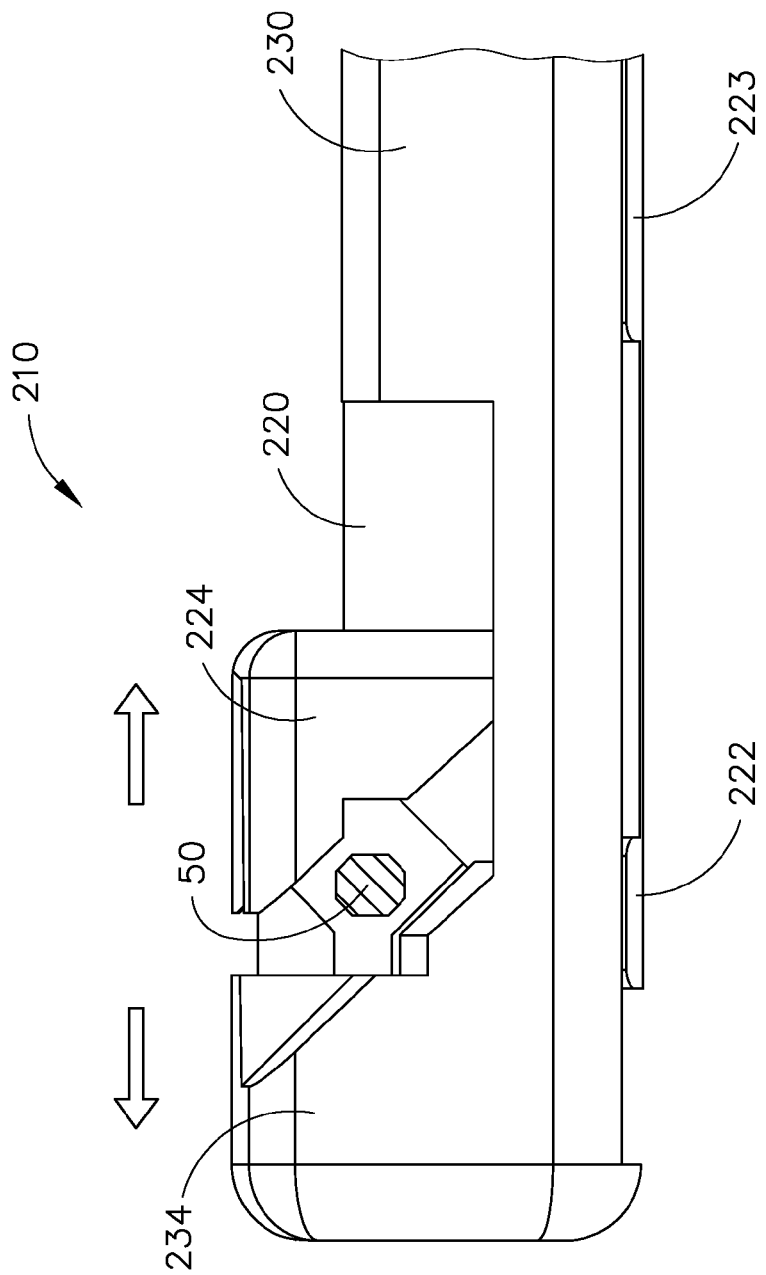
FIG. 4A depicts a partial side elevational view of the first needle grasping arm of FIG. 3, in a first operational configuration.
Figure 4B:
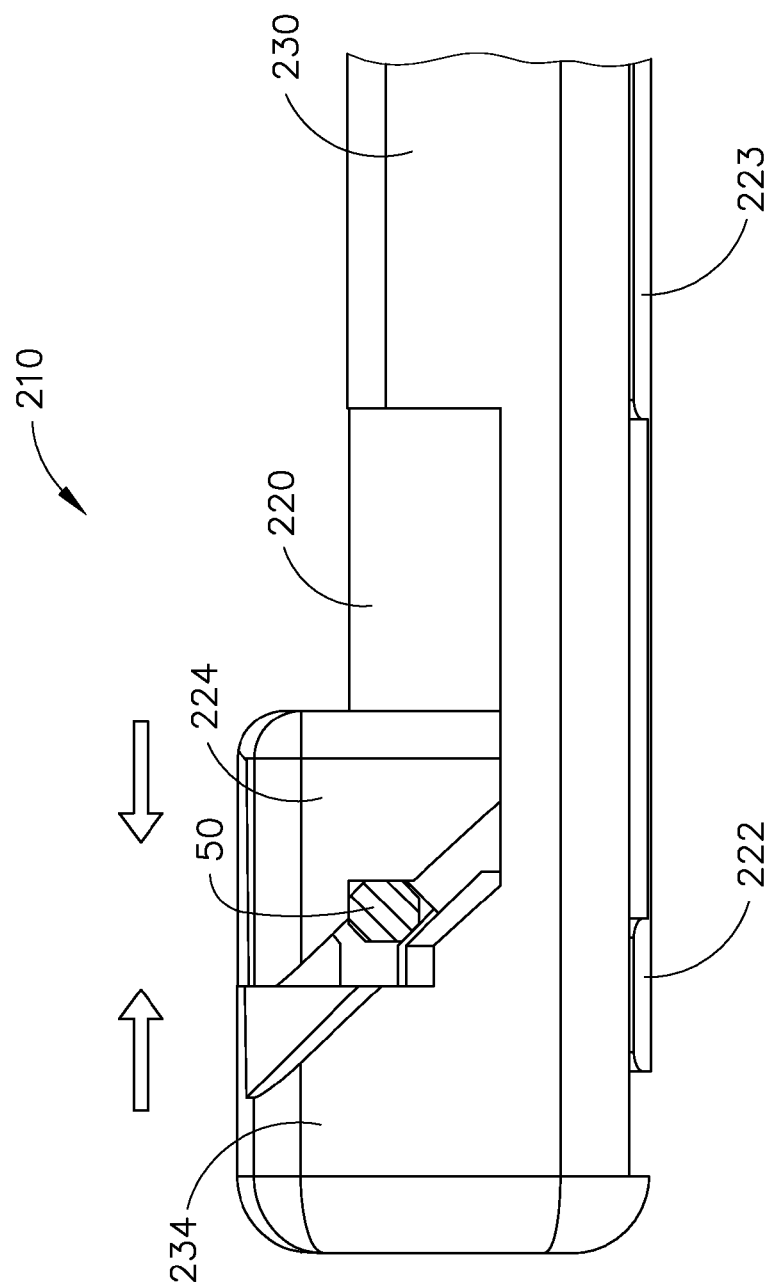
FIG. 4B depicts a partial side elevational view of the first needle grasping arm of FIG. 3, in a second operational configuration.
Figure 5:
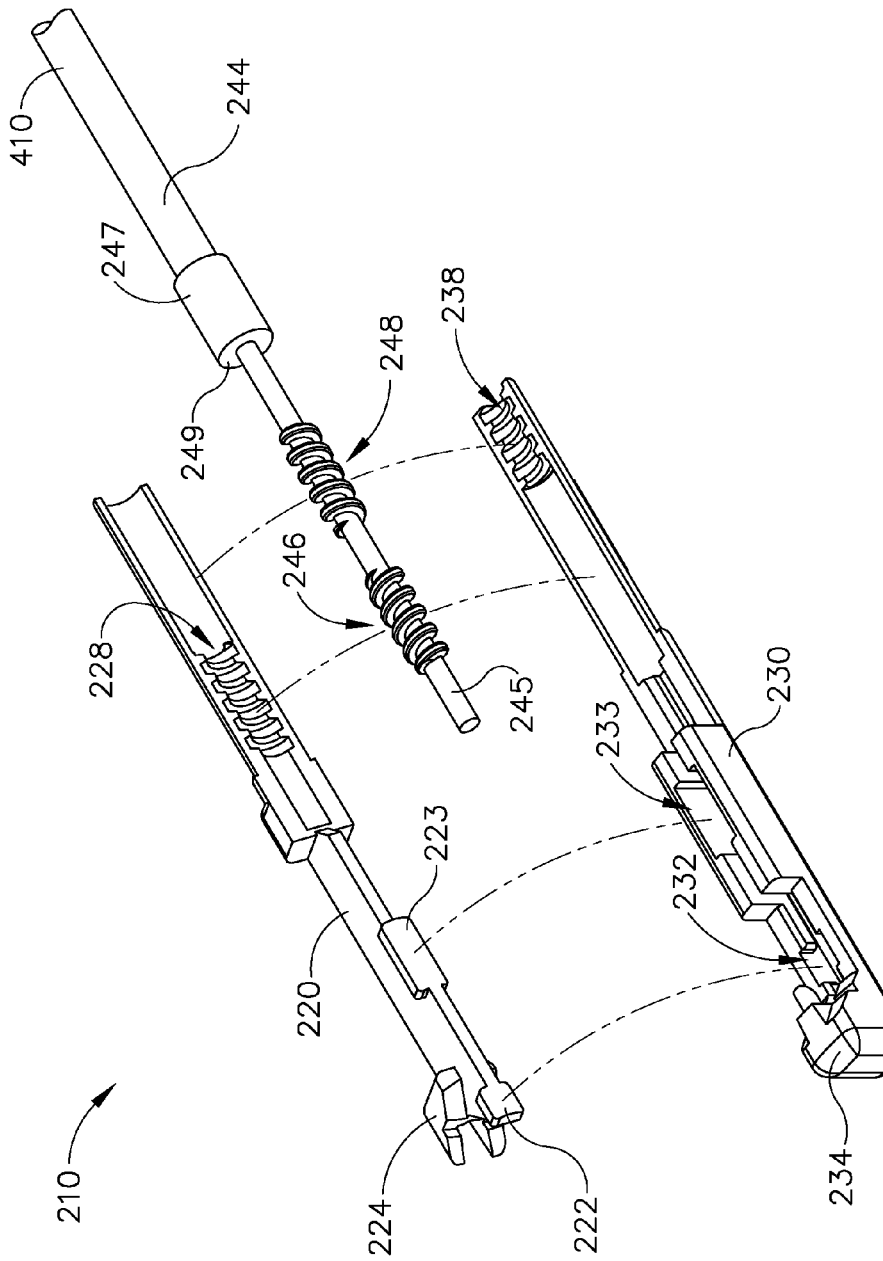
FIG. 5 depicts a partial exploded view of the first needle grasping arm of FIG. 3.

FIGS. 3-5 show first grasping arm (210) in greater detail. First grasping arm (210) comprises a first jaw (220) and a second jaw (230). Jaws (220, 230) are substantially aligned with each other and are slidable longitudinally relative to each other. As shown in FIGS. 4A-5, jaw (220) includes a pair of flanges (222, 223) that are received through corresponding openings (232, 233) of jaw (230) during assembly of arm (210). Thereafter, flanges (222, 223) prevent jaws (220, 230) from deflecting transversely away from each other. Jaws (220, 230) also include complementary needle grasping features (224, 234) that are configured to selectively grasp needle (50) as will be described in greater detail below. The proximal portion of jaw (220) includes a transversely extending fin (226). Likewise, the proximal portion of jaw (230) also includes a transversely extending fin (236). Fins (226, 236) are slidably disposed in corresponding distal slots (241, 242) of a hollow shaft (240). Hollow shaft (240) extends along the length of shaft assembly (100) and is substantially fixed within outer sheath (101). Sleeve (243) is disposed about hollow shaft (240) as shown in FIGS. 9-13 and, in this example, is substantially fixed relative to hollow shaft (240). In particular, neither sleeve (243) nor hollow shaft (240) rotate or translate relative to outer sheath (101) in this example. Hollow shaft (240) (and sleeve (243) thus provides a mechanical ground in the angular direction. It should therefore be understood that the relationship between fins (226, 236) and slots (241, 242) prevent first grasping arm (210) from rotating relative to outer sheath (101). In some other versions, however, first grasping arm (210) is rotatable relative to outer sheath (101) (e.g., by rotating hollow shaft (240) within outer sheath (101), etc.). In some such versions, hollow shaft (240) is rotatable relative to sleeve (243); while in some other versions sleeve (243) rotates with hollow shaft (240) relative to outer sheath (101). It should also be understood that, in the present example, the relationship between fins (226, 236) and slots (241, 242) still permits jaws (220, 230) to translate relative to hollow shaft (240) and outer sheath (101).

As best seen in FIGS. 4A-4B, jaws (220, 230) are simultaneously movable in opposite directions to selectively expand or reduce an opening formed by grasping features (224, 234) to receive needle (50). For instance, in FIG. 4A, jaw (220) has moved proximally toward outer sheath (101) and jaw (230) has simultaneously moved distally away from outer sheath (101) to enlarge the opening defined by grasping features (224, 234) to receive needle (50). In FIG. 4B, jaw (220) has moved distally away from outer sheath (101) and jaw (230) has simultaneously moved proximally toward outer sheath (101) to reduce the opening defined by grasping features (224, 234) to securely grasp needle (50). In some other versions, one jaw (220, 230) remains longitudinally stationary while the other jaw translates longitudinally to grasp or release needle (50) between grasping features (224, 234). However, it should be understood that in versions such as the present example where jaws (220, 230) both move simultaneously in opposite directions, such motion may further promote alignment of needle (50) within grasping features (224, 234) as compared to versions where one jaw (220, 230) always stays longitudinally fixed relative to outer sheath (101). In other words, having both grasping features (224, 234) always spaced equidistantly away from the intended path of needle (50) (regardless of whether jaws (220, 230) are open as shown in FIG. 4A or closed as shown in FIG. 4B) may better accommodate incidental deflections of needle (50) away from that intended path in either direction during use of instrument (10). Arm (210) may thus be particularly suited to accommodate instances where needle (50) has deviated away from the expected perpendicular plane of motion as described above.

FIG. 5 shows exemplary features that may be used to provide the simultaneous opposing motion of jaws (220, 230) described above. In particular, FIG. 5 shows a drive shaft (244) that includes distal end rod (245), and a first threaded section (246) and a second threaded section (248) disposed on distal end rod (245). Distal end rod (245) is separated from intermediate portion (410) of drive shaft (244) via rod connector (247). Both rod connector (247) and intermediate portion (410) of drive shaft (244) have a greater circumference than distal end rod (245), such that ledge (249) separates rod connector (247) from distal end rod (245). Drive shaft (244) is coaxially positioned within hollow shaft (240) and is rotatable within hollow shaft (240). Drive shaft (244) is rotatably driven by motor (28) in handle portion (20). The threading of first threaded section (246) is oriented opposite to the threading of second threaded section (248), such that threaded sections (246, 248) have opposite pitches. The proximal portions of jaws (220, 230) together encompass the distal portion of drive shaft (244). In particular, the proximal portion of jaw (220) includes threading (228) that meshes with first threaded section (246); while the proximal portion of jaw (230) includes threading (238) that meshes with second threaded section (248). It should therefore be understood that threading (228) has a pitch that is opposite to the pitch of threading (238). It should also be understood that, due to the relationships and orientations of threaded sections (246, 248) and threading (228, 238), drive shaft (244) will cause jaws (220, 230) to simultaneously translate away from each other (FIG. 4A) when drive shaft (244) is rotated in one direction; while drive shaft (244) will cause jaws (220, 230) to simultaneously translate toward each other (FIG. 4B) when drive shaft (244) is rotated in the other direction.

It should be understood that the opposing thread configuration described above may require relatively low torsional force to rotate drive shaft (244) to drive jaws (220, 230) toward and away from each other. It should also be understood that the opposing thread configuration described above may provide a relatively high holding force. For instance, when needle grasping features (224, 234) are driven toward each other to secure needle (50) as shown in FIG. 4B, and needle (50) is off-plane for whatever reason (e.g., incidentally oriented slightly obliquely relative to the longitudinal axis of outer sheath (101) of shaft assembly (100), etc.), the needle holding forces at grasping features (224, 234) may be self-reinforcing due to opposing forces provided through the opposing thread configuration described above, providing a mechanical advantage to urge needle (50) back into the desired planar orientation, even if tissue or some other structure is resisting such movement of needle into the desired planar orientation. Similarly, the opposing thread configuration described above may provide friction that acts as an anti-backup feature, substantially resisting inadvertent separation of grasping features (224, 234), thereby providing a very secure hold of needle (50). Other suitable components that may be used to provide opposing motion of grasping features (224, 234) (e.g., a pinion with opposing racks, etc.) will be apparent to those of ordinary skill in the art in view of the teachings herein.

As noted above, drive shaft (244) may be selectively driven in either rotational direction by motor (28), such as in response to actuation of rocker (24). Alternatively, any other motive source and/or user input feature may be used. It should also be understood that, while drive shaft (244) rotates about an axis that is parallel to the axis of outer sheath (101) of shaft assembly (100), alternative drive systems that include a rotary member may provide rotation of such a rotary member about an axis that is not parallel to the axis of outer sheath (101). For instance, a pinion based drive system may provide rotation of a drive pinion about an axis that is perpendicular to the axis of outer sheath (101). Other suitable ways in which jaws (220, 230) may be actuated will be apparent to those of ordinary skill in the art in view of the teachings herein.

B. Exemplary Second Grasping Arm

Figure 6:
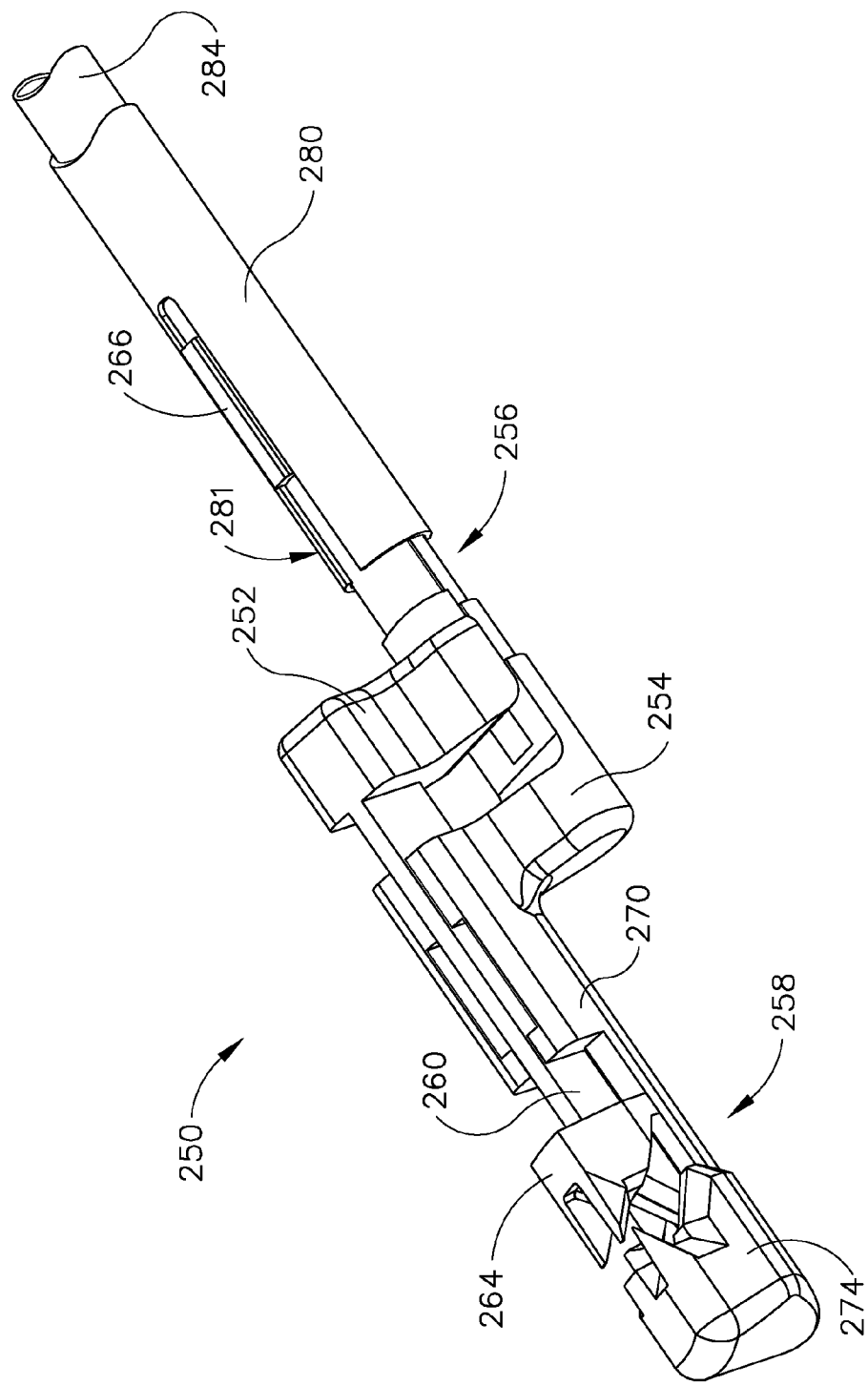
FIG. 6 depicts a first partial perspective view of a second needle grasping arm of the end effector of FIG. 2A.
Figure 7:
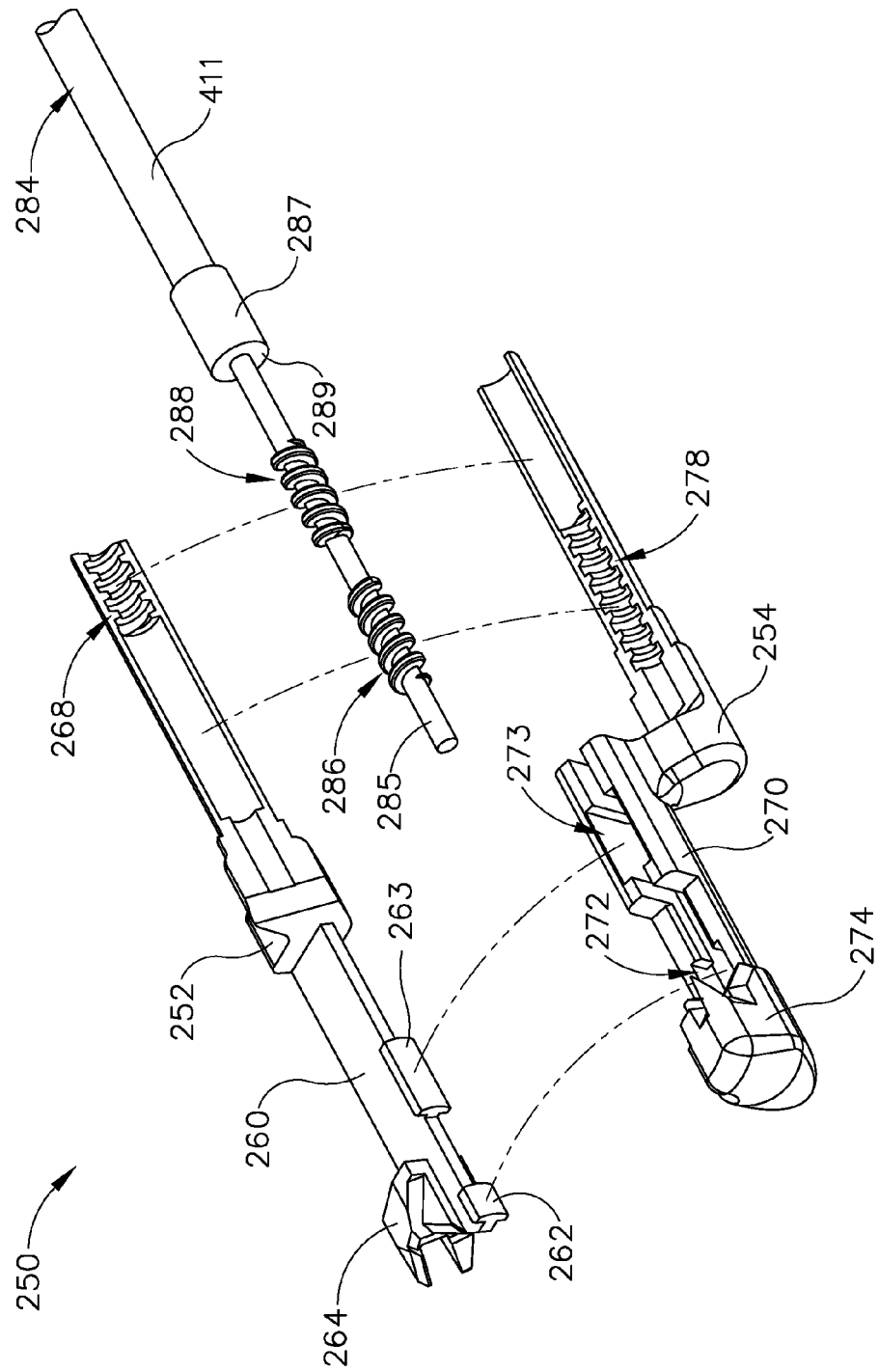
FIG. 7 depicts a partial exploded view of the second needle grasping arm of FIG. 6.
Figure 11:
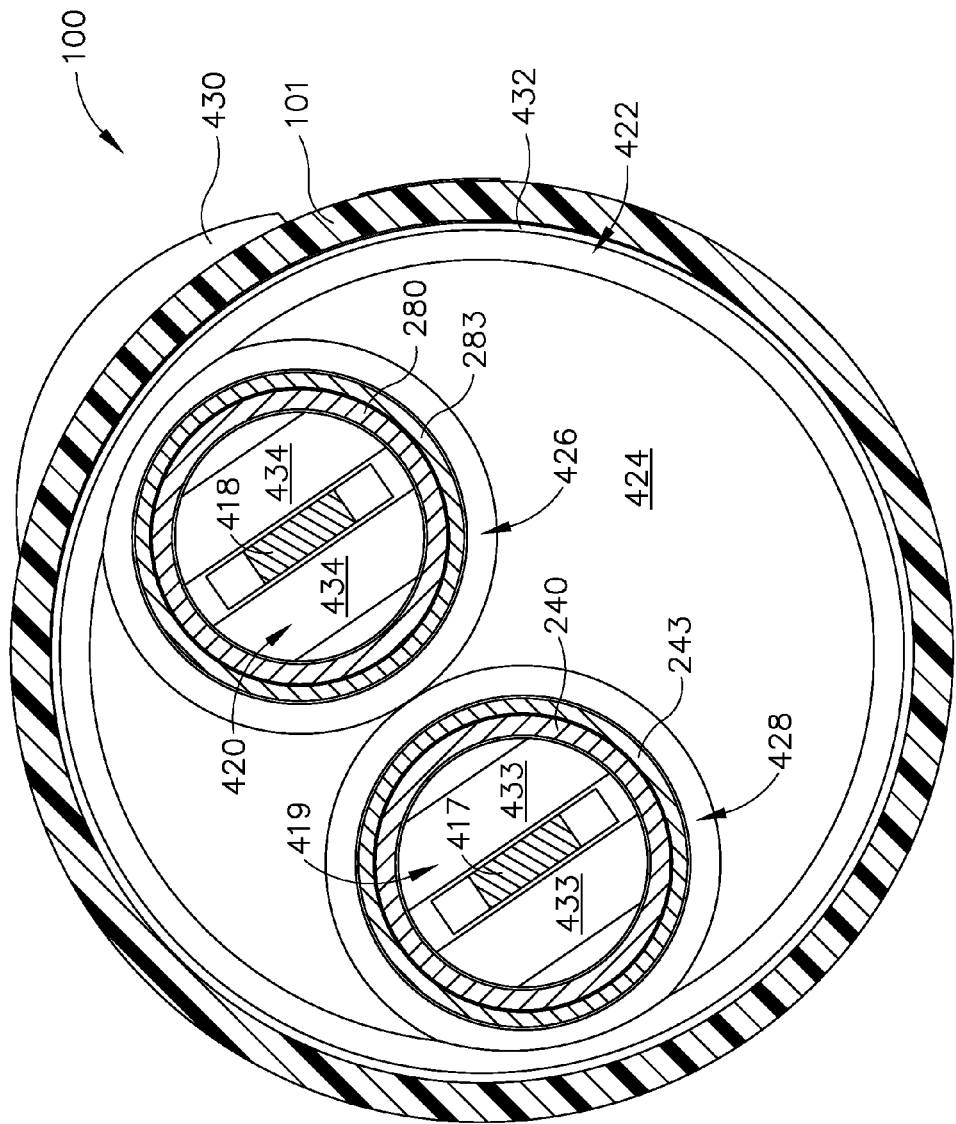
FIG. 11 depicts an end view of the suturing instrument of FIG. 1 taken along line 11-11 of FIG. 1.
Figure 14:
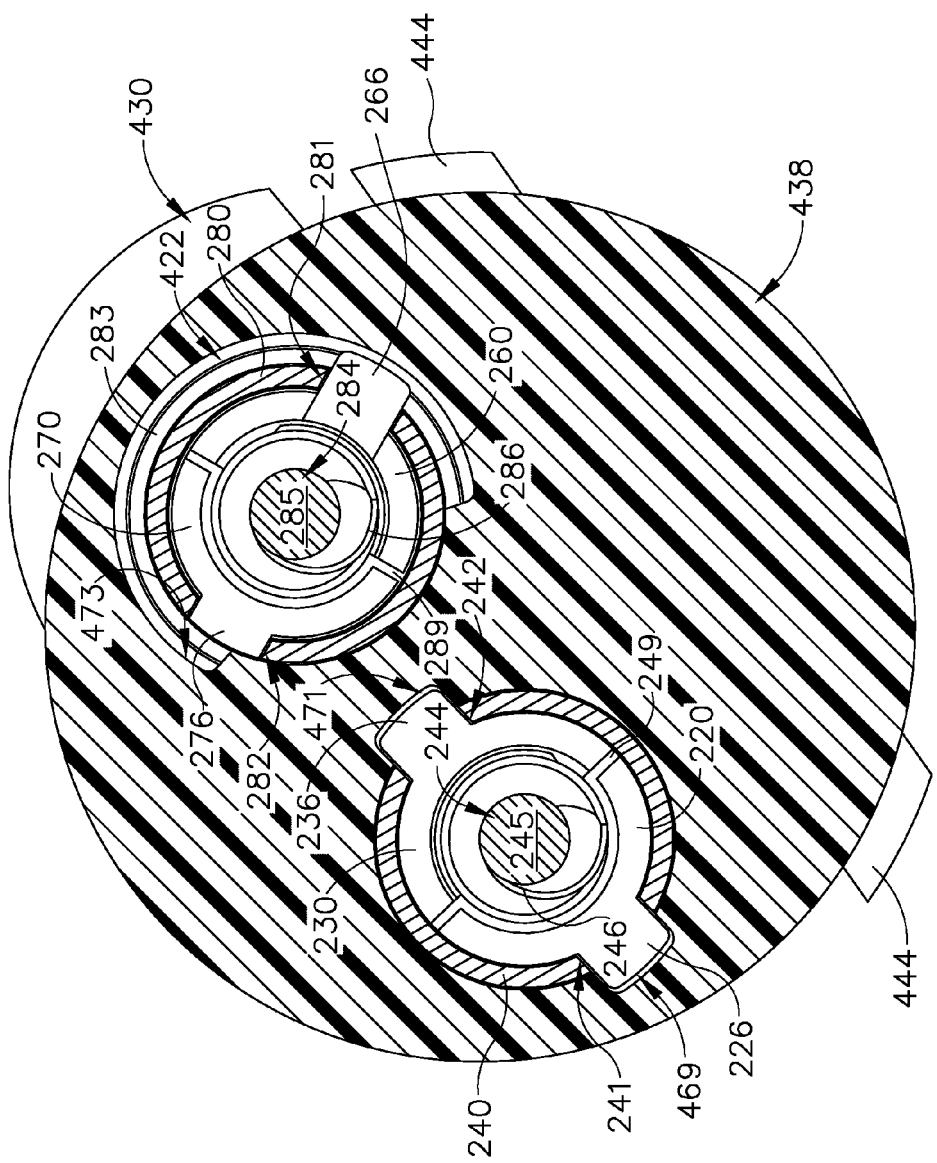
FIG. 14 depicts an end view of the shaft assembly of FIG. 9, taken along line 14-14 of FIG. 9.

FIGS. 6-7 show second grasping arm (250) in greater detail. Second grasping arm (250) comprises a first jaw (260) and a second jaw (270). Jaws (260, 270) are substantially aligned with each other and are slidable longitudinally relative to each other. As shown in FIG. 11, jaw (260) includes a pair of flanges (262, 263) that are received through corresponding openings (272, 273) of jaw (270) during assembly of arm (250). Thereafter, flanges (262, 263) prevent jaws (260, 270) from deflecting transversely away from each other. Jaws (260, 270) also include complementary needle grasping features (264, 274) that are configured to selectively grasp needle (50) as will be described in greater detail below. The proximal portion of jaw (260) includes a transversely extending fin (266). Likewise, the proximal portion of jaw (270) also includes a transversely extending fin (276), which is shown in FIG. 14. Fins (266, 276) are slidably disposed in corresponding distal slots (281, 282) (FIGS. 6 and 14) of a hollow shaft (280), which will be described in greater detail below. Referring back to FIG. 16, each jaw (260, 270) of second grasping arm (250) includes a dogleg section (252, 254). Each dogleg section (252, 254) forms a pair of right angles between a proximal portion (256) of grasping arm (250) and a distal portion (258) of grasping arm (250). The configuration of dogleg sections (252, 254) provides distal portion (258) in a parallel yet offset position relative to proximal portion (256). Thus, when grasping arm (250) is rotated about a longitudinal axis extending along the length of the proximal portion (256) of grasping arm (250), the distal portion (258) of grasping arm (250) rotates in an orbital motion about that longitudinal axis. Such motion will be described in greater detail below.

Hollow shaft (280) extends along the length of shaft assembly (100) and is partially fixed within outer sheath (101) of shaft assembly (100). Sleeve (283) is disposed about hollow shaft (280) as shown in FIGS. 9-13 and, in this example, is substantially fixed to hollow shaft (240) and partially fixed to outer sheath (101) of shaft assembly (100). In particular, hollow shaft (280) does not translate relative to outer sheath (101) in this example, though together sleeve (283) and hollow shaft (280) are rotatable relative to outer sheath (101). It should be understood that sleeve (283) may be fixed relative to hollow shaft (280) or rotatable relative to hollow shaft (280). For instance, hollow shaft (280) (and sleeve (283)) may be selectively rotated in either direction by motor (28) (e.g., in response to actuation of rocker (24), etc.). It should be understood that rotation of hollow shaft (280) relative to outer sheath (101) will provide rotation of second grasping arm (250) relative to outer sheath (101), due to the relationship between fins (266, 276) and slots (281, 282). As noted above, when second grasping arm (250) is rotated by hollow shaft (280), the distal portion (258) of grasping arm (250) rotates in an orbital motion about the longitudinal axis that is defined by both hollow shaft (280) and the proximal portion (256) of grasping arm (250). In some other versions, second grasping arm (250) is non-rotatable relative to outer sheath (101) of shaft assembly (100). It should also be understood that, in the present example, the relationship between fins (266, 276) and slots (281, 282) permits jaws (260, 270) to translate relative to hollow shaft (280) and outer sheath (101).

Similar to jaws (220, 230) of arm (210), as seen in FIGS. 4A-4B, jaws (260, 270) are simultaneously movable in opposite directions to selectively expand or reduce an opening formed by grasping features (264, 274) to receive and securely grasp needle (50).

FIG. 7 shows exemplary features that may be used to provide the simultaneous opposing motion of jaws (260, 270) described above. In particular, FIG. 7 shows a drive shaft (284) that includes distal end rod (285), and a first threaded section (286) and a second threaded section (288) disposed on distal end rod (285). Distal end rod (285) is separated from intermediate portion (411) of drive shaft (284) via rod connector (287). Both rod connector (287) and intermediate portion (411) of drive shaft (284) have a greater circumference than distal end rod (285), such that ledge (289) separates rod connector (287) from distal end rod (285). Drive shaft (284) is coaxially positioned within hollow shaft (280) and is rotatable within hollow shaft (280). Drive shaft (284) is rotatably driven by motor (28) in handle portion (20). The threading of first threaded section (286) is oriented opposite to the threading of second threaded section (288), such that threaded sections (286, 288) have opposite pitches. The proximal portions of jaws (260, 270) together encompass the distal portion of drive shaft (284). In particular, the proximal portion of jaw (260) includes threading (268) that meshes with first threaded section (286); while the proximal portion of jaw (270) includes threading (278) that meshes with second threaded section (288). It should therefore be understood that threading (268) has a pitch that is opposite to the pitch of threading (278). It should also be understood that, due to the relationships and orientations of threaded sections (286, 288) and threading (268, 278), drive shaft (284) will cause jaws (260, 270) to simultaneously translate away from each other when drive shaft (284) is rotated in one direction; while drive shaft (284) will cause jaws (260, 270) to simultaneously translate toward each other when drive shaft (284) is rotated in the other direction.

In some settings, the rotational position of hollow shaft (280) is fixed relative to outer sheath (101) when drive shaft (284) is rotated relative to outer sheath (101). Thus, hollow shaft (280) substantially holds the rotational position of jaws (260, 270) when drive shaft (284) is rotated. In some other settings, hollow shaft (280) and drive shaft (284) are rotated simultaneously relative to outer sheath (101). In some such instances, hollow shaft (280) and drive shaft (284) are rotated in the same direction and at the same speed, such that drive shaft (284) and jaws (260, 270) are rotated in the same direction and at the same speed. Thus, the longitudinal positioning of jaws (260, 270) remains fixed during such rotation. As another merely illustrative variation, hollow shaft (280) and drive shaft (284) may be rotated simultaneously relative to outer sheath (101), but at different speeds and/or in different directions. Such a scheme provides a rotation differential between jaws (260, 270) and drive shaft (284), such that jaws (260, 270) may open or close while second grasping arm (250) is simultaneously being rotated relative to outer sheath (101).

It should be understood that the opposing thread configuration described above may require relatively low torsional force to rotate drive shaft (284) to drive jaws (260, 270) toward and away from each other. It should also be understood that the opposing thread configuration described above may provide a relatively high holding force. For instance, when needle grasping features (264, 274) are driven toward each other to secure needle (50), and needle (50) is off-plane for whatever reason (e.g., incidentally oriented slightly obliquely relative to the longitudinal axis of outer sheath (101) of shaft assembly (100), etc.), the needle holding forces at grasping features (264, 274) may be self-reinforcing due to opposing forces provided through the opposing thread configuration described above, providing a mechanical advantage to urge needle (50) back into the desired planar orientation, even if tissue or some other structure is resisting such movement of needle into the desired planar orientation. Similarly, the opposing thread configuration described above may provide friction that acts as an anti-backup feature, substantially resisting inadvertent separation of grasping features (264, 274), thereby providing a very secure hold of needle (50). Other suitable components that may be used to provide opposing motion of grasping features (264, 274) (e.g., a pinion with opposing racks, etc.) will be apparent to those of ordinary skill in the art in view of the teachings herein.

As noted above, drive shaft (284) may be selectively driven in either rotational direction by motor (28), such as in response to actuation of rocker (24). Hollow shaft (280) may also be driven by motor (28). Alternatively, any other motive source and/or user input feature may be used. It should also be understood that, while drive shaft (284) rotates about an axis that is parallel to the axis of outer sheath (101) of shaft assembly (100), alternative drive systems that include a rotary member may provide rotation of such a rotary member about an axis that is not parallel to the axis of outer sheath (101). For instance, a pinion based drive system may provide rotation of a drive pinion about an axis that is perpendicular to the axis of outer sheath (101). Other suitable ways in which one or more components of second grasping arm (250) may be actuated will be apparent to those of ordinary skill in the art in view of the teachings herein.

III. Exemplary Method of Operation

Figure 8B:
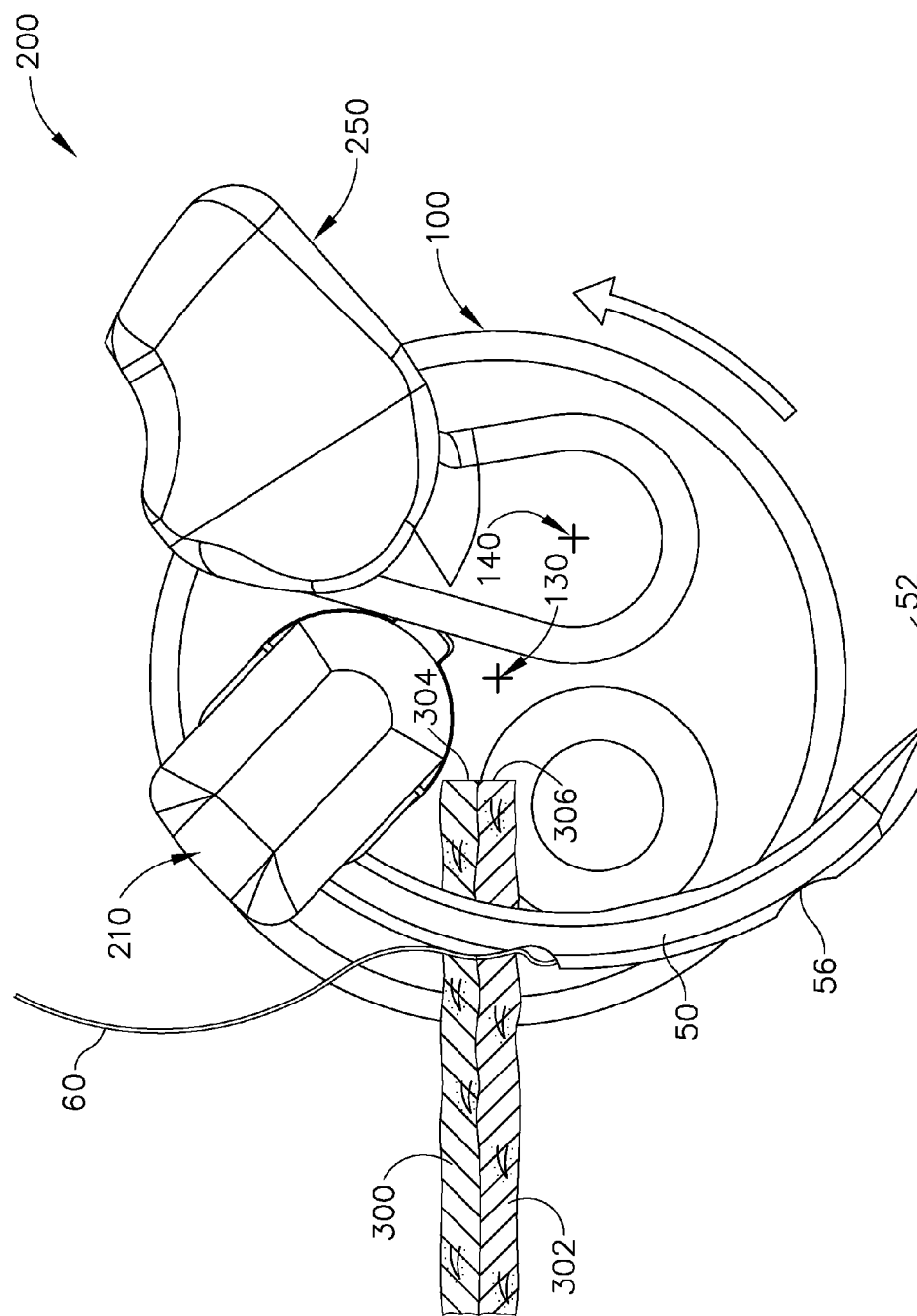
FIG. 8B depicts an end view of the end effector and needle of FIG. 2A, during an exemplary second stage of operation.

FIGS. 8A-8H depict a merely exemplary method for using surgical instrument (10). In particular, FIG. 8A shows end effector (200) positioned adjacent to apposed layers (300, 302) of tissue. End effector (200) is positioned such that the longitudinal axis (130) of outer sheath (101) of shaft assembly (100) is substantially parallel to the outer edges (304, 306) of tissue layers (300, 302). In this sense, "substantially parallel" simply means that end effector (200) is oriented in relation to tissue layers (300, 302) in a manner sufficient to enable needle (50) to be passed through tissue layers (300, 302). It should therefore be understood that longitudinal axis (130) need not necessarily be truly parallel with outer edges (304, 306), though longitudinal axis (130) may in fact be truly parallel with outer edges (304, 306) in some instances. It should also be understood that instrument (10) and needle (50) may be used to secure tissue together in an edge-to-edge arrangement rather than securing apposed layers (300, 302) as shown. Other suitable settings in which instrument (10) and needle (50) may be used will be apparent to those of ordinary skill in the art in view of the teachings herein. It should also be understood that the curved configuration of needle (50) may provide a more intuitive operation for the surgeon than a straight needle would, such as by providing better predictability for where sharp tip (52) will come through tissue.

As shown in FIG. 8A, first grasping arm (210) is securely holding needle (50), with sharp tip (52) exposed. In particular, grasping portions (224, 234) of jaws (220, 230) hold needle (50) at grasping region (56). Needle (50) is oriented along a plane that is substantially transverse to longitudinal axis (130). Once end effector (200) has been positioned as shown in FIG. 8A, the entire instrument (10) is rotated about longitudinal axis (130) to drive sharp tip (52) through tissue layers (300, 302), as shown in FIG. 8B. In the example shown, the rotational direction for instrument (10) is counterclockwise viewed from the distal end toward the proximal end, though it should be understood that instrument (10) may be rotated clockwise instead (e.g., depending on the orientation of sharp tip (52)). During the transition from the position of FIG. 8A to the position of FIG. 8B, the rotational position of grasping arms (210, 250) relative to outer sheath (101) remains fixed, such that grasping arms (210, 250) rotate unitarily with outer sheath (101) about longitudinal axis (130). The longitudinal position of jaws (220, 230, 260, 270) also remains fixed during this transition. As can also be seen in FIG. 8B, needle (50) has started to pull suture (60) through tissue layers (300, 302) at this stage. It should be understood that, in the stages shown in FIGS. 8A-8B, grasping arms (210, 250) and needle (50) are in the same rotational positions relative to outer sheath (101) as shown in FIG. 2A. It should also be noted that the configuration of end effector (200) and needle (50) may provide the surgeon with enhanced visibility of sharp tip (52) exiting tissue layers (300, 302) during the transition from FIG. 8A to FIG. 8B, particularly with arm (250) being rotated out of the way at this stage.

Figure 8C:
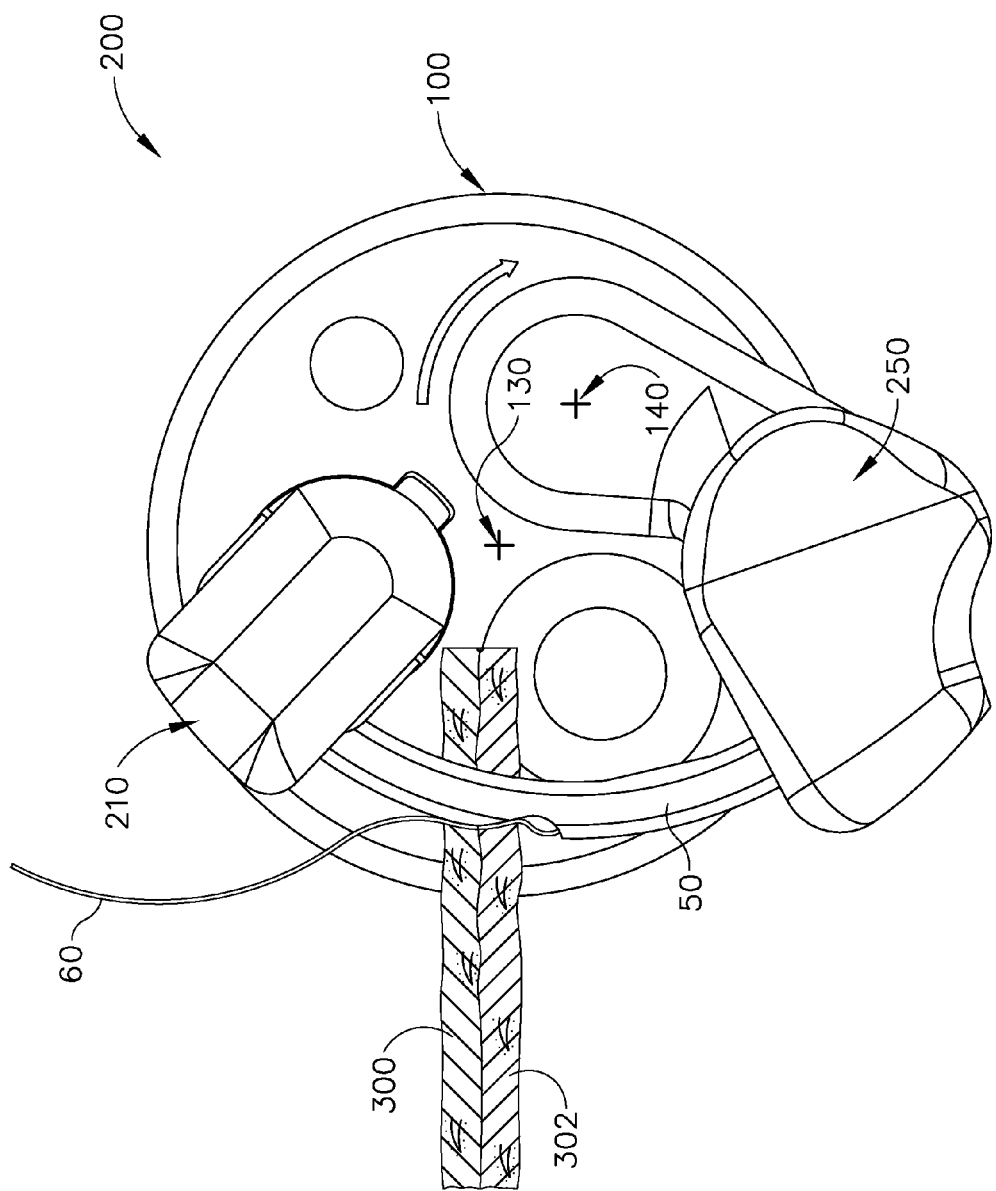
FIG. 8C depicts an end view of the end effector and needle of FIG. 2A, during an exemplary third stage of operation.

After needle (50) has been driven at least partially through tissue layers (300, 302), second grasping arm (250) is rotated about its own axis (140) toward needle (50) as shown in FIG. 8C. Such rotation is provided by rotating hollow shaft (280) relative to outer sheath (101). The rotational position of outer sheath (101) relative to axis (130) remains fixed during the transition from the configuration shown in FIG. 8B to the configuration shown in FIG. 8C. It should be understood that, in the stage shown in FIG. 8C, grasping arms (210, 250) and needle (50) are in the same rotational positions relative to outer sheath (101) as shown in FIG. 2B.

In some versions, jaws (260, 270) are already opened (in a manner similar to that shown in FIG. 4A for jaws (220, 230)) by the time second grasping arm (250) starts rotating from the position shown in FIG. 8B to the position shown in FIG. 8C. In some other versions, jaws (260, 270) are actively opened during the transition from the position shown in FIG. 8B to the position shown in FIG. 8C, such that jaws (260, 270) are fully open by the time second grasping arm (250) reaches the position shown in FIG. 8C. Once second grasping arm (250) reaches the position shown in FIG. 8C, jaws (260, 270) close (in a manner similar to that shown in FIG. 4B for jaws (220, 230)) to grasp needle (50) at grasping region (58) with grasping features (264, 274). In addition, jaws (220, 230) open (as shown in FIG. 4A) to release needle (50) from grasping features (224, 234) at grasping region (56). In some versions, jaws (260, 270) close to grasp needle (50) at substantially the same time as jaws (220, 230) open to release needle (50). In some other versions, jaws (220, 230) do not open to release needle (50) until jaws (260, 270) have closed to grasp needle (50). Various suitable timing schemes and ways in which such schemes may be carried out will be apparent to those of ordinary skill in the art in view of the teachings herein.

Figure 8D:
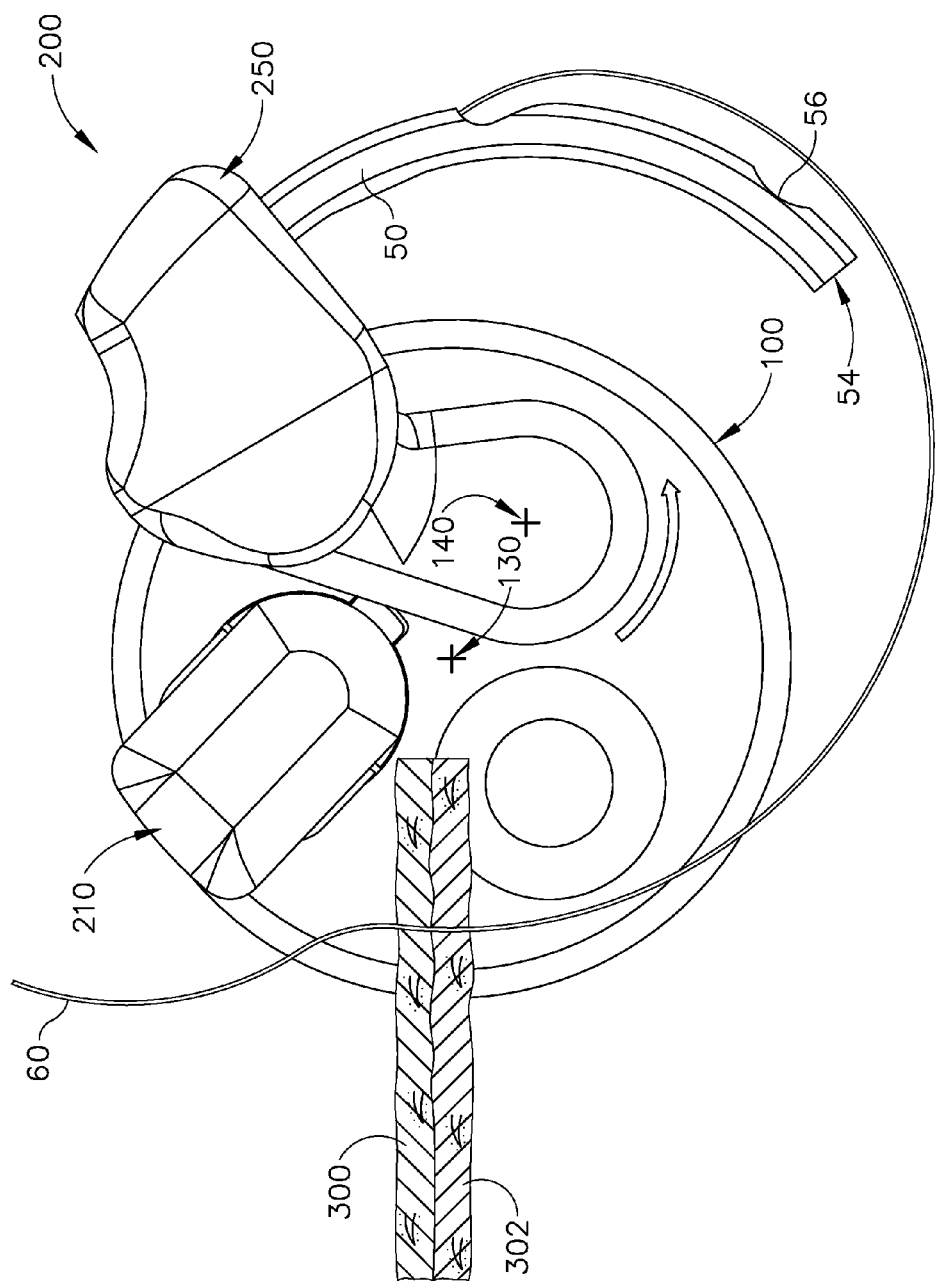
FIG. 8D depicts an end view of the end effector and needle of FIG. 2A, during an exemplary fourth stage of operation.

Once control of needle (50) has been effectively passed from grasping arm (210) to grasping arm (250), grasping arm (250) is rotated about axis (140) to the position shown in FIG. 8D. Such rotation is provided by once again rotating hollow shaft (280) relative to outer sheath (101). The rotational position of outer sheath (101) relative to axis (130) continues to be fixed during the transition from the configuration shown in FIG. 8C to the configuration shown in FIG. 8D. It should be understood that, in the stage shown in FIG. 8D, grasping arms (210, 250) and needle (50) are in the same rotational positions relative to outer sheath (101) as shown in FIG. 2C. As can also be seen in FIG. 8D, grasping arm (250) pulls suture (60) through tissue layers (300, 302) during the transition from FIG. 8C to FIG. 8D.

Figure 8E:
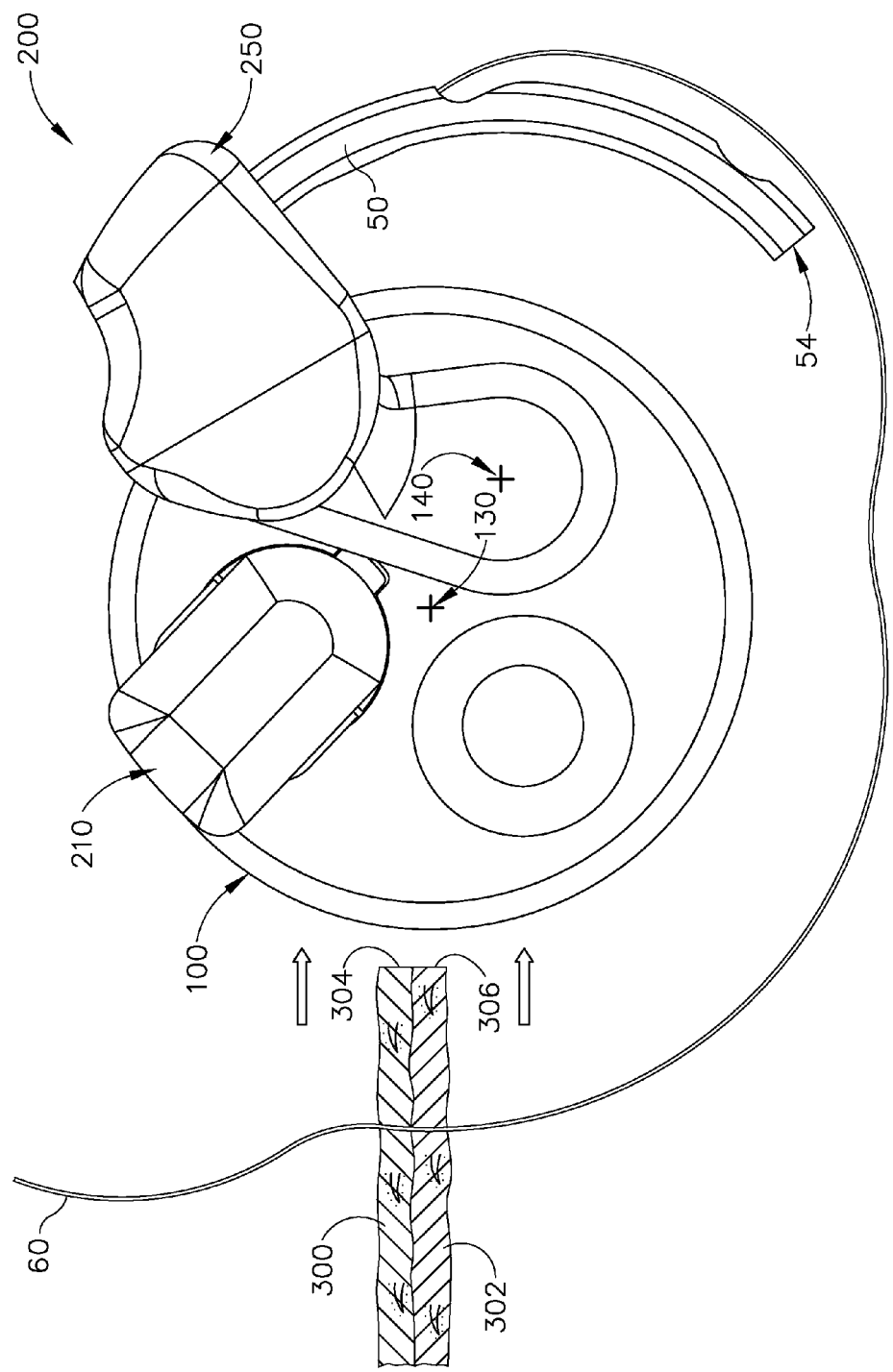
FIG. 8E depicts an end view of the end effector and needle of FIG. 2A, during an exemplary fifth stage of operation.

After reaching the configuration shown in FIG. 8D, the surgeon pulls the entire end effector (200) away from tissue layers (300, 302), along a path that is substantially transverse to axis (130), as shown in FIG. 8E. It should be understood that this path may be oblique relative to axis (130) and/or edges (304, 306), helical, and/or of any other suitable configuration. It should also be understood that neither arm (210, 250) is rotated relative to outer sheath (101) in the present example during the transition from the position shown in FIG. 8D to the position shown in FIG. 8E. Thus, in the stage shown in FIG. 8E, grasping arms (210, 250) and needle (50) are still in the same rotational positions relative to outer sheath (101) as shown in FIG. 2C. In moving instrument (10) away from tissue layers (300, 302) during the transition to the position shown in FIG. 8E, suture (60) is pulled further through tissue layers (300, 302).

Figure 8F:
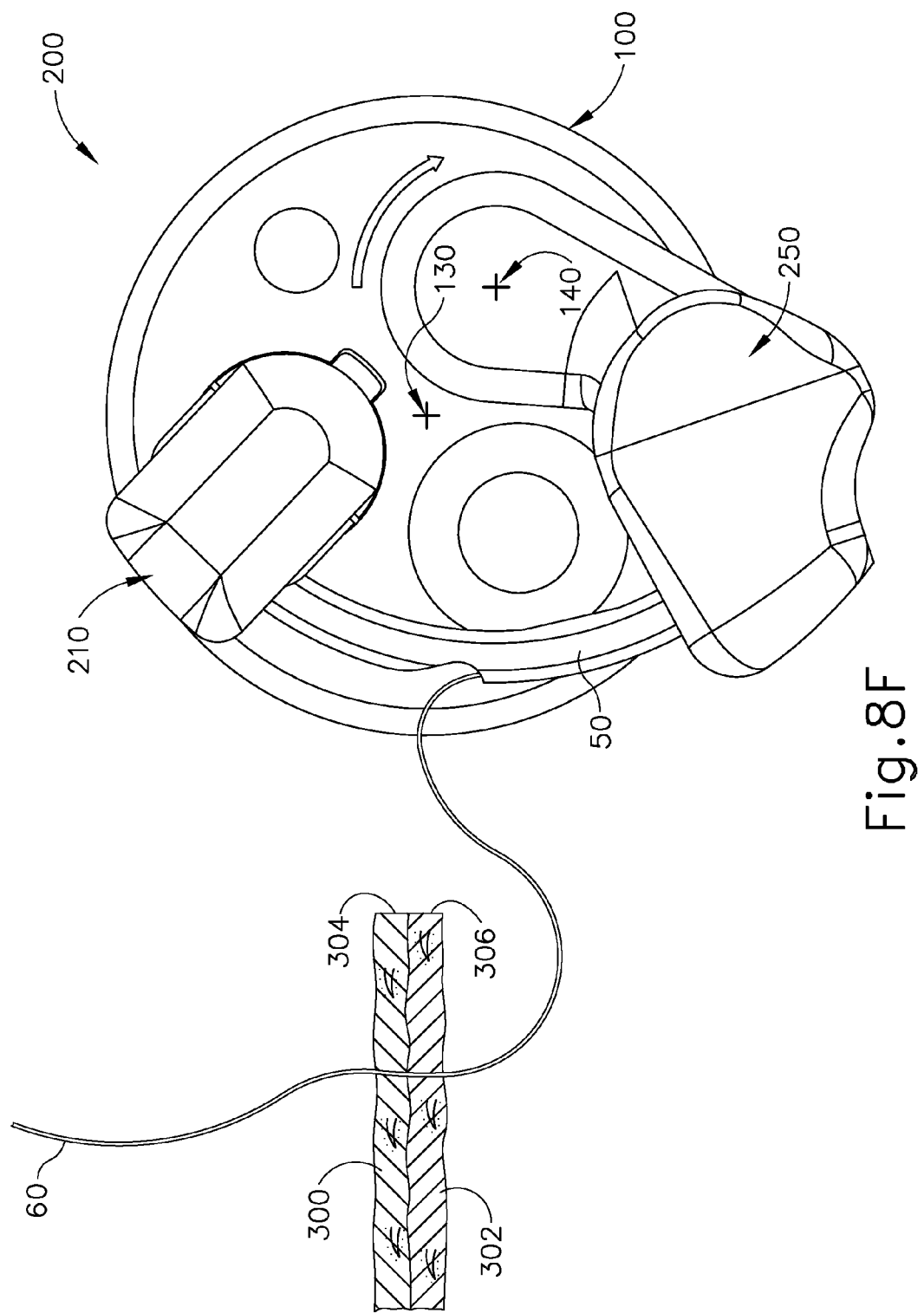
FIG. 8F depicts an end view of the end effector and needle of FIG. 2A, during an exemplary sixth stage of operation.

With end effector (200) positioned sufficiently away from tissue layers (300, 302), second grasping arm (250) is rotated about axis (140) to the position shown in FIG. 8F. The rotational position of outer sheath (101) relative to axis (130) remains fixed during the transition from the configuration shown in FIG. 8E to the configuration shown in FIG. 8F. It should be understood that, in the stage shown in FIG. 8F, grasping arms (210, 250) and needle (50) are in the same rotational positions relative to outer sheath (101) as shown in FIG. 2B. End effector (200) is positioned far enough away from tissue layers (300, 302) during the transition from the position shown in FIG. 8E to the position shown in FIG. 8F such that blunt end (54) of needle (50) does not touch tissue layers (300, 302). The rotation of second grasping arm (250) to the position shown in FIG. 8F places grasping region (58) of needle (50) back between grasping portions (224, 234) of jaws (220, 230).

In some versions, jaws (220, 230) are already opened (as shown in FIG. 4A) by the time second grasping arm (250) starts rotating from the position shown in FIG. 8E to the position shown in FIG. 8F. In some other versions, jaws (220, 230) are actively opened during the transition from the position shown in FIG. 8E to the position shown in FIG. 8F, such that jaws (220, 230) are fully open by the time second grasping arm (250) reaches the position shown in FIG. 8F. Once second grasping arm (250) reaches the position shown in FIG. 8F, jaws (220, 230) close (as shown in FIG. 4B) to grasp needle (50) at grasping region (56) with grasping portions (224, 234). In addition, jaws (260, 270) open to release needle (50) from grasping portions (264, 274) at grasping region (58). In some versions, jaws (220, 230) close to grasp needle (50) at substantially the same time as jaws (260, 270) open to release needle (50). In some other versions, jaws (260, 270) do not open to release needle (50) until jaws (220, 240) have closed to grasp needle (50). Various suitable timing schemes and ways in which such schemes may be carried out will be apparent to those of ordinary skill in the art in view of the teachings herein.

Figure 8G:
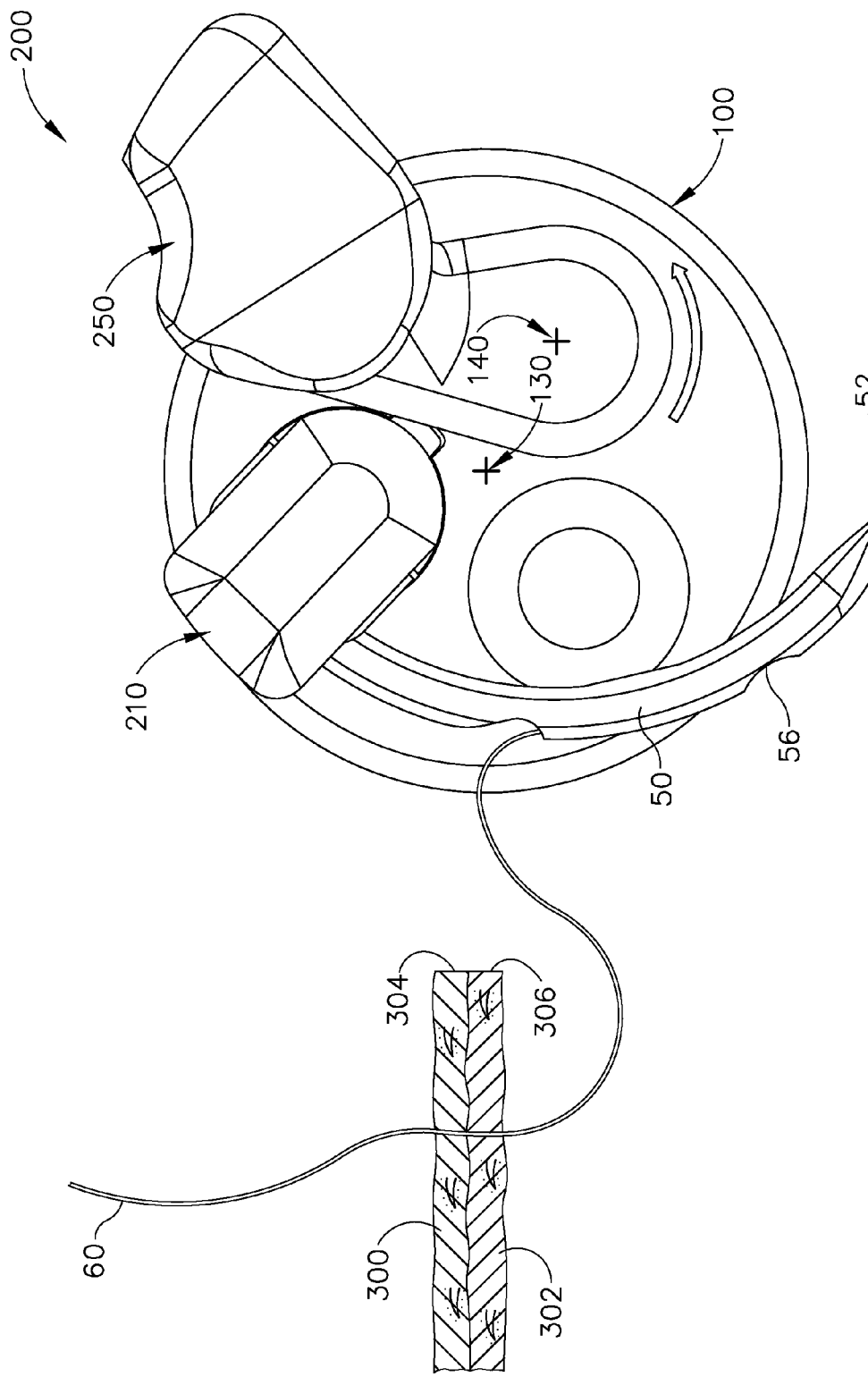
FIG. 8G depicts an end view of the end effector and needle of FIG. 2A, during an exemplary seventh stage of operation.

Once control of needle (50) has been effectively passed from grasping arm (250) back to grasping arm (210), grasping arm (250) is rotated about axis (140) to the position shown in FIG. 8G. Such rotation is provided by once again rotating hollow shaft (280) relative to outer sheath (101). The rotational position of outer sheath (101) relative to axis (130) continues to be fixed during the transition from the position shown in FIG. 8F to the position shown in FIG. 8G. It should be understood that, in the stage shown in FIG. 8G, grasping arms (210, 250) and needle (50) are in the same rotational positions relative to outer sheath (101) as shown in FIG. 2A.

Figure 8H:
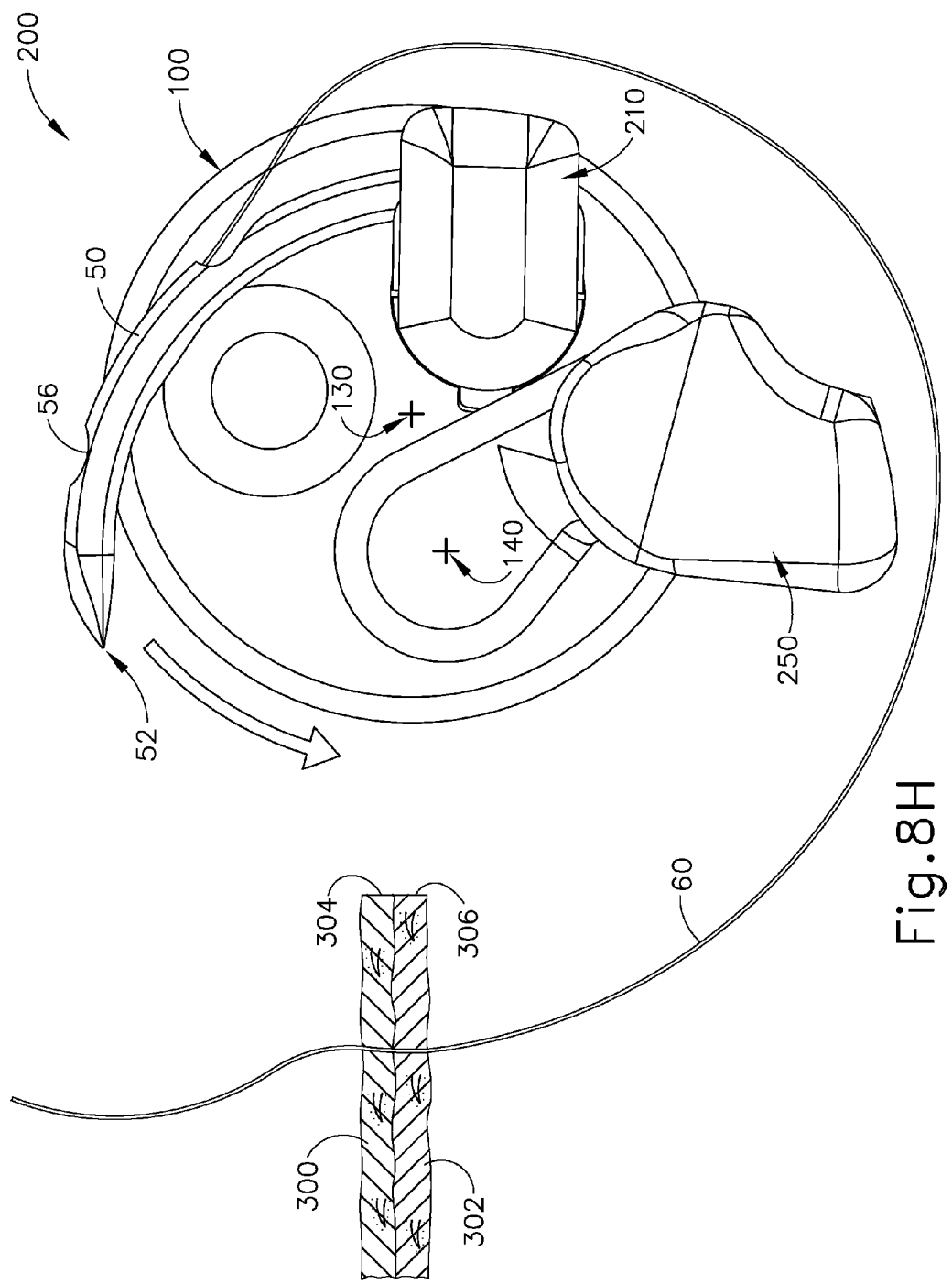
FIG. 8H depicts an end view of the end effector and needle of FIG. 2A, during an exemplary eighth stage of operation.

Once grasping arm (250) has been rotated away from needle (50) as shown in FIG. 8G, the entire instrument (10) is once again rotated about longitudinal axis (130) to position sharp tip (52) above tissue layers (300, 302), as shown in FIG. 8H. In the example shown, the rotational direction for instrument (10) is again counterclockwise viewed from the distal end toward the proximal end, though it should be understood that instrument (10) may be rotated clockwise instead (e.g., depending on the orientation of sharp tip (52)). During this transition, the rotational position of grasping arms (210, 250) relative to outer sheath (101) remains fixed, such that grasping arms (210, 250) rotate unitarily with outer sheath (101) about longitudinal axis (130). The longitudinal position of jaws (220, 230, 260, 270) also remains fixed during this transition. In the stage shown in FIG. 8H, grasping arms (210, 250) and needle (50) remain in the same rotational positions relative to outer sheath (101) as shown in FIG. 2A.

Having reached the configuration shown in FIG. 8H, end effector (200) may be moved back toward tissue layers (300, 302), such as along a path transverse to axis (130), to again reach the position shown in FIG. 8A. The above described cycle may then be repeated as many times as desired until an appropriate number of stitches have been made through tissue layers (300, 302). The free end of suture (50) may then be knotted, clipped, or otherwise secured.

It should be understood that instrument (10) may be advanced distally or proximally along axis (130) in each stitching cycle, each stitching cycle being represented by the succession of stages depicted in FIGS. 8A-8H. For instance, instrument (10) may be advanced distally or proximally along axis (130) during the transition from the position shown in 8E to the position shown in 8F. As another merely illustrative example, instrument (10) may be advanced distally or proximally along axis (130) during the transition from the position shown in 8G to the position shown in 8H. Other suitable stages at which instrument (10) may be advanced distally or proximally will be apparent to those of ordinary skill in the art in view of the teachings herein. It should be understood that the distance of each incremental distal or proximal movement of instrument (10) during successive stitching cycles may be selected based on a desired stitch density along the length of the tissue being sutured. It should also be understood that, once stitching is complete, suture (60) may define a generally helical path through tissue layers (300, 302). Other suitable ways in which instrument (10) may be used will be apparent to those of ordinary skill in the art in view of the teachings herein.

As should be apparent to those of ordinary skill in the art, needle (50) of the present example orbits about axis (140), which is offset from axis (130) of outer sheath (101) in the present example. This may enable needle (50) to travel about an arc having a radius that is greater than the radius of a trocar through which outer sheath (101) is inserted. In other words, the circumferential path of needle (50) need not be limited to the circumference of the trocar through which outer sheath (101) is inserted when the orbital axis of needle (50) is offset from axis (130) of outer sheath (101). Thus, the configuration of end effector (200) in the present example may permit a larger radius needle to be used, and larger stitches to be made, than what would be permitted if the orbital motion of needle (50) were centered about axis (130) of outer sheath (101). In some other versions, needle (50) does move in an orbital fashion about axis (130) of outer sheath (101).

While terms such as "clockwise" and "counterclockwise" have been used to describe directions of rotational movement during exemplary uses of end effectors (200), it should be understood that these specific rotational directions are being provided only in reference to the examples depicted in the drawings. It is contemplated that rotational movement may be provided in directions opposite to those used above. Therefore, use of the terms "clockwise" and "counterclockwise" in any examples described herein should not be viewed as limiting in any way.

IV. Exemplary Shaft Assembly

FIGS. 9-13 show varying views of exemplary internal components of shaft assembly (100), including pairs of parallel concentric shafts within outer sheath (101) of shaft assembly (100). FIG. 9 shows a view of instrument (10) in which outer sheath (101) has been removed for the purpose of more easily viewing underlying components. Proximal end (402) of shaft assembly (100) of instrument (10) is magnified in FIG. 13, as described further below. Distal end (404) of shaft assembly (100) is magnified as FIG. 12, also described further below. FIG. 9 shows instrument (10) as including sleeves (243, 283), which are respectively disposed about hollow shafts (240, 280), which are respectively disposed about drive shafts (244, 284), as described above. FIG. 9 shows first exposed portion (406) underneath sleeve (283) and a removed portion of underlying hollow shaft (280) toward distal end (404) of instrument (10). The components described below for sleeve (283) are generally similar to the components underlying sleeve (243). First exposed portion (406) shows a proximal end of underlying drive shaft (284) having proximal end connector (408). Proximal end connector (408) has a wider circumference than an intermediate, adjacent portion (410) of drive shaft (284), and is separated from portion (410) by a ledge (412).

Figure 13:
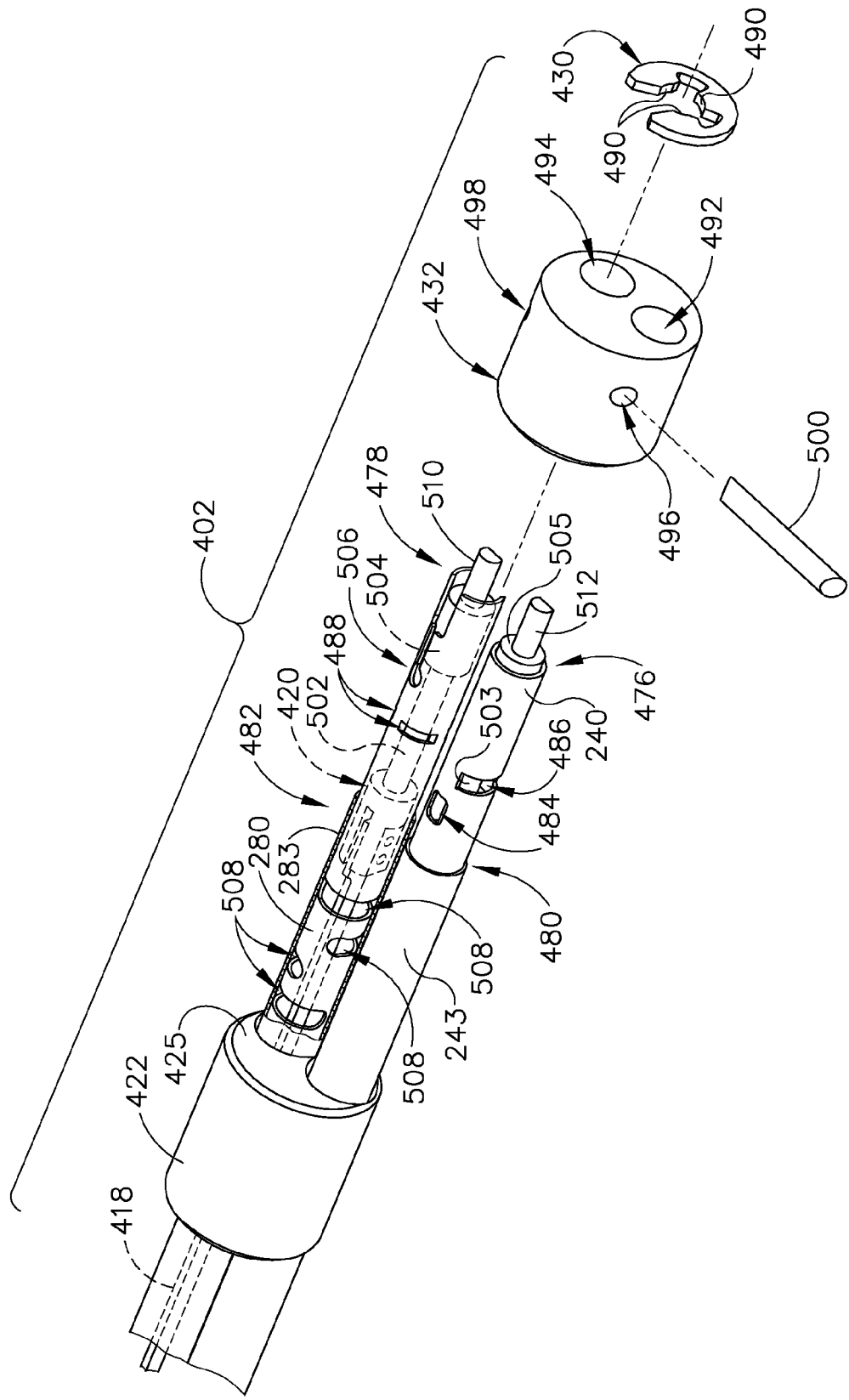
FIG. 13 depicts an exploded perspective view of a proximal end of the shaft assembly of FIG. 9 with phantom line views of an inner beam and an outer bearing shaft with a solid line view inner bearing shaft of one of a pair of parallel concentric shafts shown, the other of the pair of concentric shafts being shown in a solid line view.

FIG. 9 shows second exposed portion (414) between proximal and distal ends of instrument (10) and third exposed portion (416) at proximal end (402) of shaft assembly (100). Second exposed portion (414) shows underlying and exposed beam (418). A distal end of beam (418) connects to proximal end connector (408) of drive shaft (284). A proximal end of beam (418) connects to beam end piece (420), which is wider than beam (418), and which is shown in FIG. 13 as described in greater detail below. End piece (420), beam (418), proximal end connector (408), and drive shaft (284) are unitarily coupled together, such that when beam (418) is rotated via beam end piece (420), drive shaft (284) unitarily rotates as described above with respect to FIG. 7. FIG. 11 shows beam (417), which is coupled at a distal end to a proximal end connector (not shown) of drive shaft (244) that is similar to proximal end connector (408) described above. A proximal end of beam (417) connects to beam end piece (419), which is wider than beam (417). End piece (419), beam (417), the proximal end connector at the distal end of beam (517), and drive shaft (244) are unitarily coupled together, such that when beam (417) is rotated via beam end piece (419), drive shaft (244) unitarily rotates as described above with respect to FIG. 5.

Figure 10:
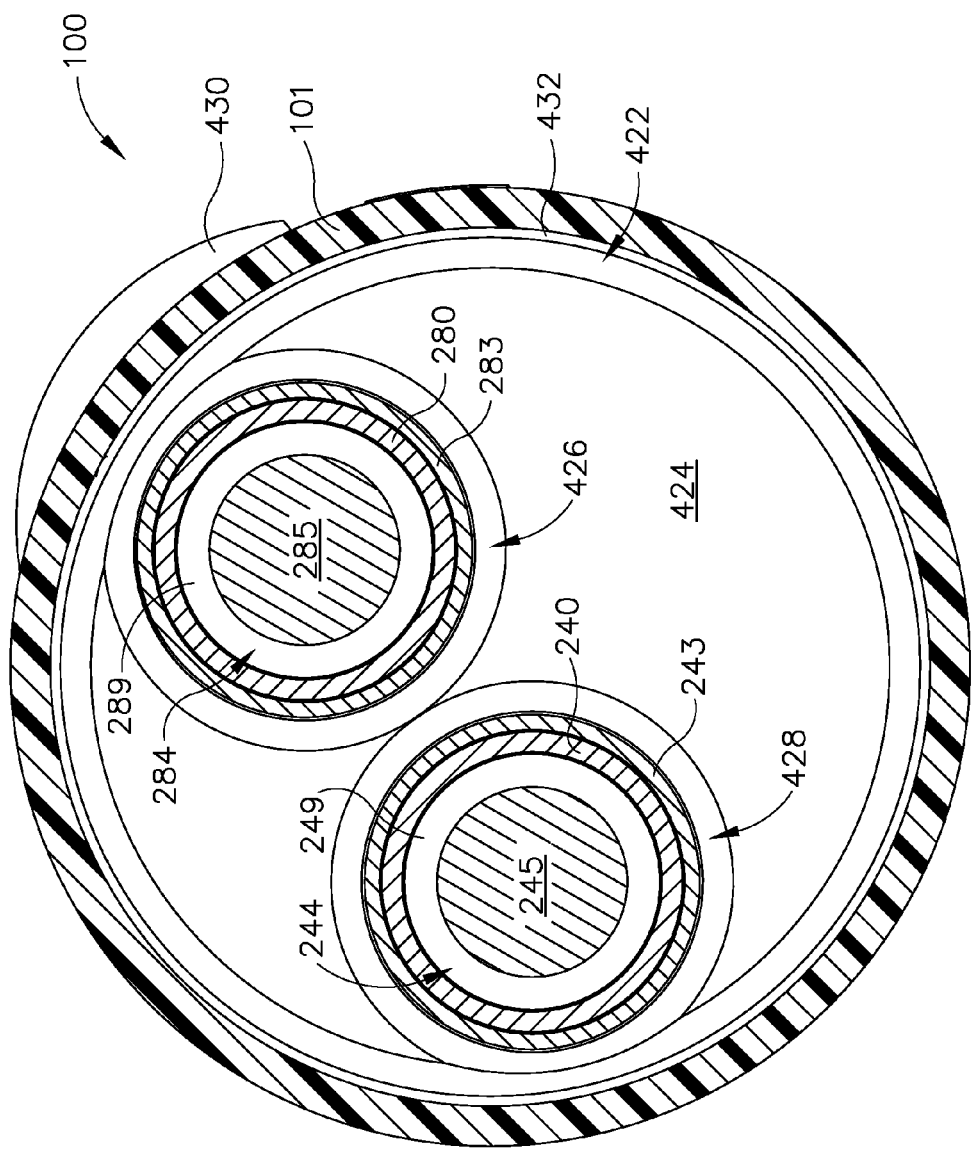
FIG. 10 depicts an end view of the suturing instrument of FIG. 1 taken along line 10-10 of FIG. 1.

Separate, discrete spacer bushings (422) are spaced between proximal end (402) and distal end (404) of shaft assembly (100) of instrument (10). Each spacer bushing (422) includes a pair of apertures (426, 428), as best seen in FIG. 10. Apertures (426, 428) are disposed between distal end (424) and a proximal end (425), shown in FIG. 13. Each aperture is sized to receive one of the pair of sleeves (243, 283). Spacer bushings (422) maintain sleeves (243, 283) in a parallel relationship along the length of shaft assembly (100).

FIG. 10 shows a cross-sectional end view of shaft assembly (100) taken along line 10-10 shown in FIG. 1. As shown in FIG. 10, distal end (424) of spacer bushing (422) defines the pair of apertures (426, 428). Aperture (426) is disposed about sleeve (283), which is disposed about hollow shaft (280). Hollow shaft (280) is disposed about drive shaft (284), as described above. Aperture (428) is disposed about sleeve (243), which is disposed about hollow shaft (240). Hollow shaft (240) is disposed about drive shaft (244), as described above.

FIG. 11 shows a cross-sectional end view of shaft assembly (100) taken along line 11-11 shown in FIG. 1. FIG. 11 shows the same view as FIG. 10 except for the parts about which hollow shafts (240, 280) are disposed. At this section of shaft assembly (100), hollow shafts (240, 280) are disposed about beams (417, 418). The end view shows distal end (433, 434) of beam end piece (419, 420), where beam end piece (419) is similar to beam end piece (420) described above. As best seen in FIG. 9, both beam end pieces (419, 420) are disposed within proximal cap (432) of shaft assembly (100).

Figure 12:
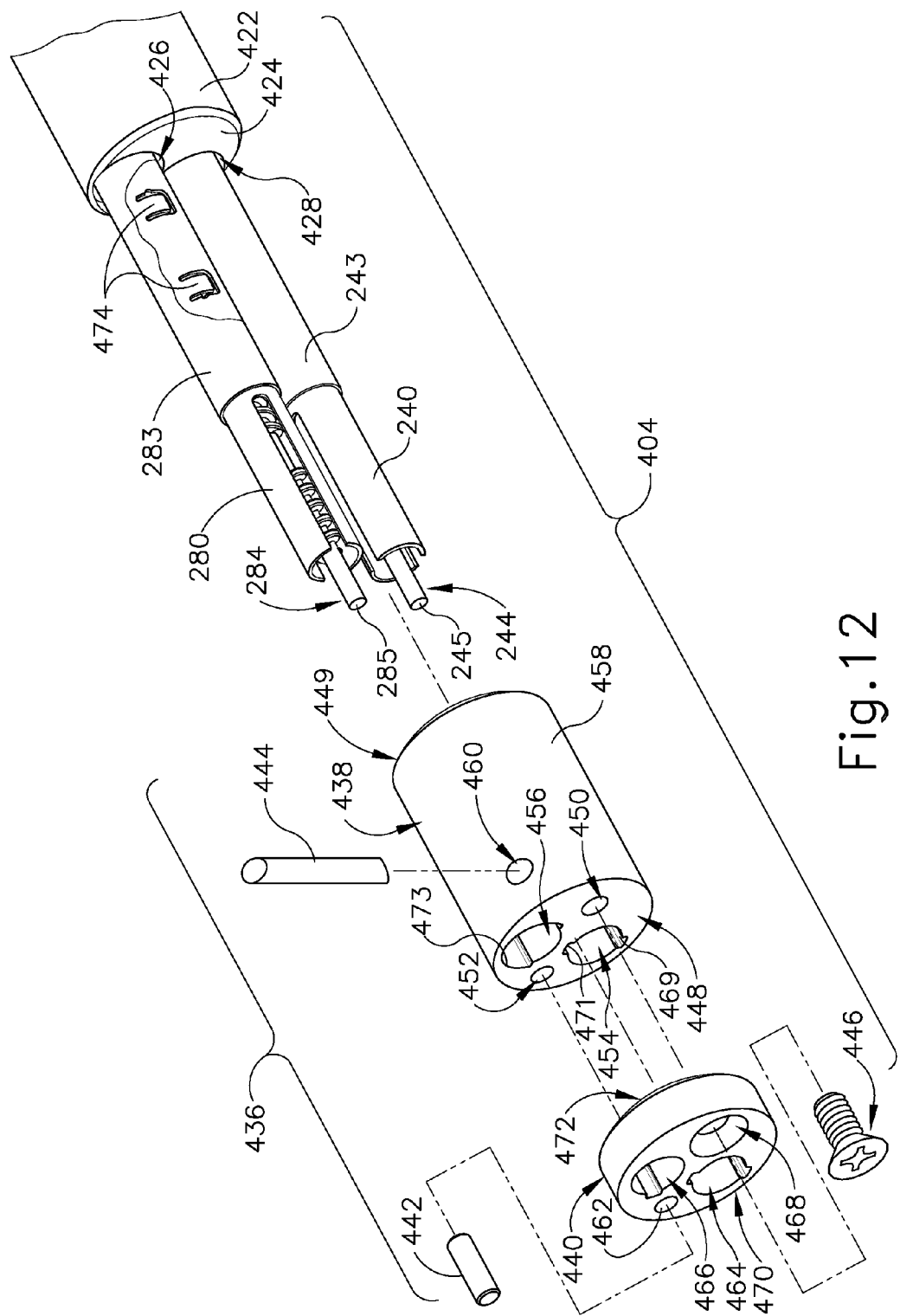
FIG. 12 depicts an exploded and fragmented perspective view of a distal end of the shaft assembly of FIG. 9.

FIG. 12 shows an exploded view of distal end (404), which connects to end effector (200) as described above. Distal cap assembly (436) includes distal cap (438), cap lock (440), first pin (442), second pin (444), and screw (446). Distal cap (438) has distal end (448) and proximal end (449), and four apertures (450, 452, 454, 456) disposed and extending substantially between ends (448, 449). Sidewall (458) is disposed between proximal end (449) and distal end (448), and has aperture (460). A channel extends between apertures (450) and (460) and is sized to receive pin (444), which secures outer sheath (101) with distal cap (438). The outer ends of pin (444) are curved to complement the outer curvature of outer sheath (101), to present a flush outer surface.

Cap lock (440) includes four apertures (462, 464, 466, 468) disposed and extending substantially between distal end (470) and proximal end (472). Aperture (468) in the present example is countersunk to enable a flush surface presentation by distal end (470) and screw (446). Aperture (462) of cap lock (440) is alignable with aperture (452) of distal cap (438). Both apertures (462) and (452) are sized to receive pin (442), which acts to connect cap lock (440) to distal cap (438). In this position, aperture (468) of cap lock (440) is aligned with aperture (450) of distal cap (438). Screw (446) is threadably receivable within apertures (468) and (450) to further secure cap lock (440) to distal cap (438). In the secured position, apertures (464, 454) are aligned, as are apertures (466, 456). Aligned apertures (464, 454) are sized to receive sleeve (243) and the components disposed within sleeve (243), as described above. Aligned apertures (466, 456) are sized to receive sleeve (283) and the components disposed within sleeve (283), as described above. Any of apertures (464, 466, 454, 456) may include one or more additional keyways extending between proximal and distal ends of respective cap lock (440) or distal cap (438), the keyways extending beyond a circumference of the respective aperture into the surface of an interior wall defining the respective aperture. The keyways allow for capture (to prevent rotation) and/or translation of fins or other components extending from hollow shafts (240, 280), for instance.

In particular, FIG. 14 shows a cross-sectional end view in which fins (226, 236) of jaws (220, 230) of arm (210) (FIG. 3) are received in respective keyways (469, 471) of aperture (454) of distal cap (438). Each keyway (469, 471) is sized and shaped to receive a respective fin (226, 236) and to prevent rotation of arm (210). Aperture (456) of distal cap (438) includes an arcuate keyway (473), which is formed by first inner wall (475) defining aperture (456). Arcuate keyway (473) is shaped to receive fin (266) of jaw (260) of arm (250) (FIG. 6). Fin (276) of jaw (270) of arm (250) is sized to extend no farther and to be movably flush against second inner wall (477), which has a smaller radius from a center of aperture (456) than first inner wall (476). Fin (266) of jaw (260) of arm (250) is sized to extend past fin (276) and to extend no further than first inner wall (475). Arcuate keyway (473) thus permits fin (266) to rotate within aperture (456), thus allowing arm (250) to rotate within distal cap (438). For example, the transition between FIGS. 8B to 8C show arm (250) rotationally moving in a clockwise direction relative to shaft assembly (100), and the transition between FIGS. 8C to 8D show arm (250) rotationally moving in a counter-clockwise direction relative to shaft assembly (100).

Hollow shaft (280) is shown in an exposed portion to underlying sleeve (283) and to include torsionally compliant members such as U-shaped, torsional cutouts (474). Such torsional cutouts may also be formed in hollow shaft (240) within sleeve (243). Torsional cutouts (474) assist with compensation of needle tolerances and with maintaining a holding force on the above-described clamping system of needle (50) within one or both of arms (210, 250). As jaws of one or both of arms (210, 250) contact needle (50) as described above, the rotation drive of drive shaft (244, 284) continues to rotate past a point of contact to allow for a sufficient grip of the jaws against needle (50) while substantially reducing snapping or buckling from this grip. In particular, torsional cutouts (474) accommodate overdrive of drive shaft (244, 284) by allowing hollow shafts (240, 280) to deform slightly without snapping or undesirably buckling.

FIG. 13 shows a partially exploded, partially phantom view of proximal end (402), which connects to handle portion (20), as described below. Proximal ends (476, 478) of respective hollow shafts (240, 280) extend beyond proximal ends (480, 482) of sleeves (243, 283). The extending portions of hollow shafts (240, 280) may include one or more torsional cutouts (508), which are similar in effect to torsional cutouts (474) shown in FIG. 12 and described above. The extending portion of hollow shaft (240) includes notch (484) configured to receive a boss (not shown) from handle portion (20) to fix shaft assembly (100) to handle portion (20) and to prevent rotational and/or translational movement of hollow shaft (240) relative to handle portion (20). Alternatively, hollow shaft (240) could be rotatable relative to handle portion (20) if desired.

The extending portions of hollow shafts (240, 280) include circumferentially extending and/or discretely spaced cutouts such as cutouts (486, 488). In the present example, discretely spaced cutouts (488) are spaced about hollow shaft (280) and are sized and shaped to receive interior prongs (490) defined in an interior portion of e-clip (430) to secure e-clip (430) to hollow shaft (280). An outer portion of e-clip (430) is disposed in cutout (486). E-clip (430) thus prevents hollow shafts (240, 280) from translating relative to each other. However, cutout (486) is configured to permit e-clip (430) and hollow shaft (280) to rotate relative to hollow shaft (240), as hollow shaft (240) remains fixed relative to handle assembly (20). Proximal cap (432) is shown as exploded from the assembled components of distal end (402). A pair of apertures (492, 494) on proximal cap (432) extend between proximal and distal ends of proximal cap (432) and are spaced and sized to receive respective sleeves (243, 283) and portions of hollow shafts (240, 280) distal of cutout (484). A pair of apertures (496, 498) disposed on a sidewall between distal and proximal ends of proximal cap (432) define a channel. The channel of proximal cap (432) is sized and shaped to receive cap pin (500), which secures outer sheath (101) with proximal cap (432). The outer ends of pin (500) are curved to complement the outer curvature of outer sheath (101), to present a flush outer surface.

Phantom lines in FIG. 13 show beam (418) extending to proximal end (402) of shaft assembly (100) of instrument (10) and ending at connected beam end piece (420) via a protrusion and notch press fit, though other suitable types of connections are within the scope of the present disclosure. A proximal end shaft (502) proximally extends unitarily from beam end piece (420). A proximal end piece (504) is unitarily disposed about proximal end shaft (502) to abut against the inner diameter of hollow shaft (280). Drive member (510) is rotatably disposed at proximal end (478) of hollow shaft (280), and is unitarily coupled with proximal end piece (504). Drive member (510), proximal end piece (504), proximal end shaft (502), beam end piece (420), beam (418), and drive shaft (284) all rotate together unitarily. Drive member (510) couples with a transmission assembly (1000) in handle portion (20), as will be described in greater detail below, to rotate drive shaft (284).

A similar structure and components may be found within hollow shaft (240). While not depicted in FIG. 13, it should be understood that beam (417) and beam end piece (419) described above are positioned within hollow shaft (240) in a longitudinal region corresponding to the longitudinal region of hollow shaft (280) in which beam (418) and beam end piece (420) are positioned. A proximal end shaft (503) proximally extends unitarily from beam end piece (419). A proximal end piece (505) is unitarily disposed about proximal end shaft (503) to abut against the inner diameter of hollow shaft (240). Drive member (512) is rotatably disposed at proximal end (476) of hollow shaft (240), and is unitarily coupled with proximal end piece (505). Drive member (512), proximal end piece (505), proximal end shaft (503), beam end piece (419), beam (417), and drive shaft (244) all rotate together unitarily. Drive member (512)

couples with transmission assembly (1000) in handle portion (20), as will be described in greater detail below, to rotate drive shaft (244).

Hollow shaft (280) in the present example differs from hollow shaft (240) in that hollow shaft (280) is rotatable relative to handle portion (20). Furthermore, proximal end (402) of hollow shaft (280) includes a longitudinally extending cutout portion (506) extending from proximal end (478) of hollow shaft (280) toward cutout (488). Cutout portion (506) includes a first rectangular portion adjacent to proximal end (478), a second, narrower rectangular portion distal to the first rectangular portion, and a third circular cutout portion distal to the second rectangular portion. Cutout portion (506) couples with transmission assembly (1000) in handle portion (20), as will be described in greater detail below, to rotate hollow shaft (280). While certain shapes have been described for the cutouts and apertures herein, other shapes and sizes as apparent to one of ordinary skill in the art in view of the teachings herein are within the scope of this disclosure. Hollow shaft (280) also includes additional circumferentially and longitudinally spaced torsional cutouts (508) between beam end piece (420) and the proximal-most spacer bushing (422), as shown in FIG. 13.

Shaft assembly (100) may include additional added and/or integrated controls to provide for additional functionality. For example, functionality may be provided to supply a sufficiently strong yet resilient needle capable of being stowed within outer sheath (101) when not in use (e.g., during insertion of shaft assembly (100) into a trocar). Additionally or alternatively, functionality may be provided to allow for articulation of end effector (200) when in use during a procedure to articulate away from a longitudinal axis of shaft assembly (100). Further, shaft assembly (100) may be a modular component that is connectable to handle portion (20) via sheaths (240, 280), sleeves (243, 283), and proximal end shaft (502). Thus, shaft assembly (100) may disconnect at a distal surface of handle portion (20) to provide for reusable configurations. It should also be understood that, while shaft assembly (100) of the present example includes a first pair of shafts (280, 284) and a second pair of shafts (240, 244), other variations may include additional shafts and/or additional shaft pairs. Such additional shafts and/or additional shaft pairs may replace, supplement, or vary the functionality of at least part of either or both shaft pairs (240, 244, 280, 284). In addition or in the alternative, additional shafts and/or additional shaft pairs may provide their own functionality. Other variations of shaft assembly (100) will be apparent to those of ordinary skill in the art in view of the teachings herein.

V. Exemplary Handle with Motor and Transmission Assembly

Figure 15:
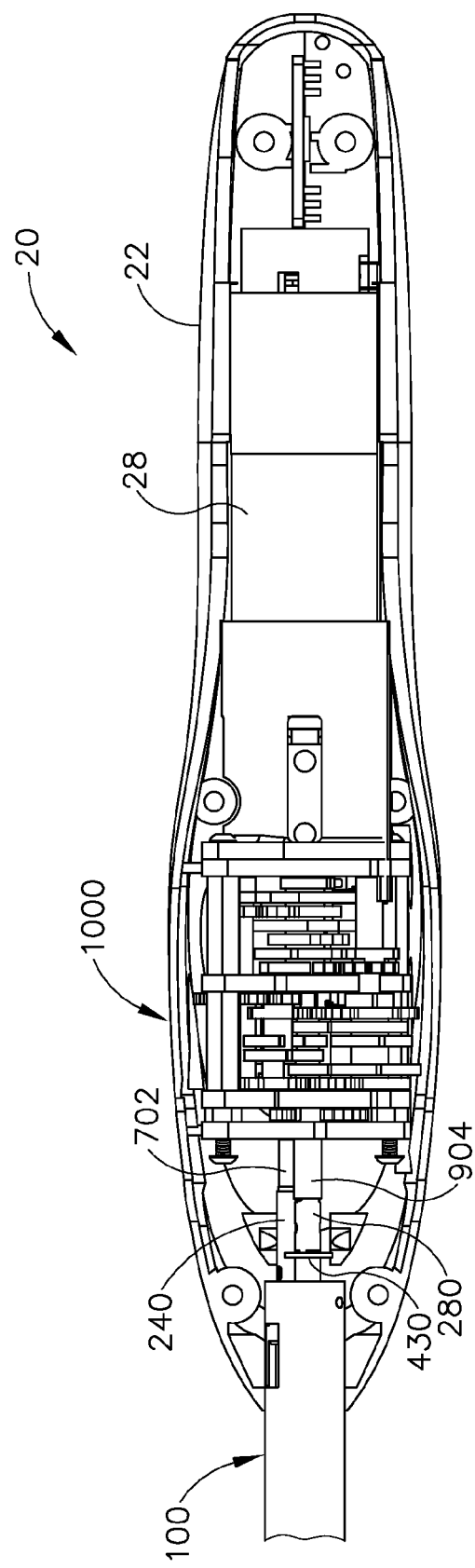
FIG. 15 depicts a top plan view of the handle assembly of the suturing instrument of FIG. 1, with a top housing piece removed to reveal exemplary drive assembly components.

FIGS. 15-56 depict various exemplary components that may be used to drive shaft assembly (100) and end effector (200). In particular, FIG. 15 shows handle portion (20) with a bottom portion of grip (22) removed to reveal motor (28) and a transmission assembly (1000). Motor (28) of the present example comprises a conventional electric motor, though it should be understood that motor (28) may comprise any other suitable source of rotary power, including but not limited to a pneumatic motor, a manually rotatable knob, a manually rotatable crank, a torsion spring, etc. In addition, while motor (28) of the present example is powered by an integral power source (26) (e.g., 3 volt rechargeable lithium ion battery located within handle portion (20), etc.), it should be understood that motor (28) may be powered by any other suitable type of source, including but not limited to a cable leading to an external power source, etc. It should also be understood that a control module (not shown), such as a microcontroller, etc., may be located in handle portion (20) to control motor (28) in accordance with a predefined control logic/sequence and/or based on user input. Motor (28) is coupled to a single input shaft (600) of transmission assembly (1000). As will be described in greater detail below, transmission assembly (1000) is configured to convert rotation of input shaft (600) into a complex sequence of holding and/or rotation of three separate output shafts (700, 800, 900). While output shafts (700, 800, 900) are configured to drive end effector (200) described above in the present example, it should be understood that output shafts (700, 800, 900) may alternatively drive various other kinds of end effectors as will be apparent to those of ordinary skill in the art in view of the teachings herein.

Output shaft (700) is coupled to drive member (512), which is integrally coupled with drive shaft (244) and is thereby operable to rotate drive shaft (244) as described above. In particular, output shaft (700) is coupled with drive member (512) by a sleeve (702), which is disposed about the distal end of output shaft (700) and about the proximal end of drive member (512) as shown in FIG. 15. Output shaft (700) and drive member (512) each have a similar cross section resembling a circle with a chord section removed to present a flat region. The inner bore of sleeve (702) includes a complementary profile to engage these flat regions, such that output shaft (700), sleeve (702), and drive member (512) rotate together unitarily. By way of example only, output shaft (700) and/or drive member (512) may be further secured to sleeve (702) by a press-fit, using an adhesive, by a set screw, and/or in any other suitable fashion. As another merely illustrative example, output shaft (700) and/or drive member (512) may be may be permitted to slide longitudinally relative to sleeve (702) to some degree (e.g., to accommodate longitudinal displacement produced by deformations resulting from intentional overdrive, etc.). Various other suitable ways in which output shaft (700) may be coupled with drive member (512) will be apparent to those of ordinary skill in the art in view of the teachings herein.

Figure 18:
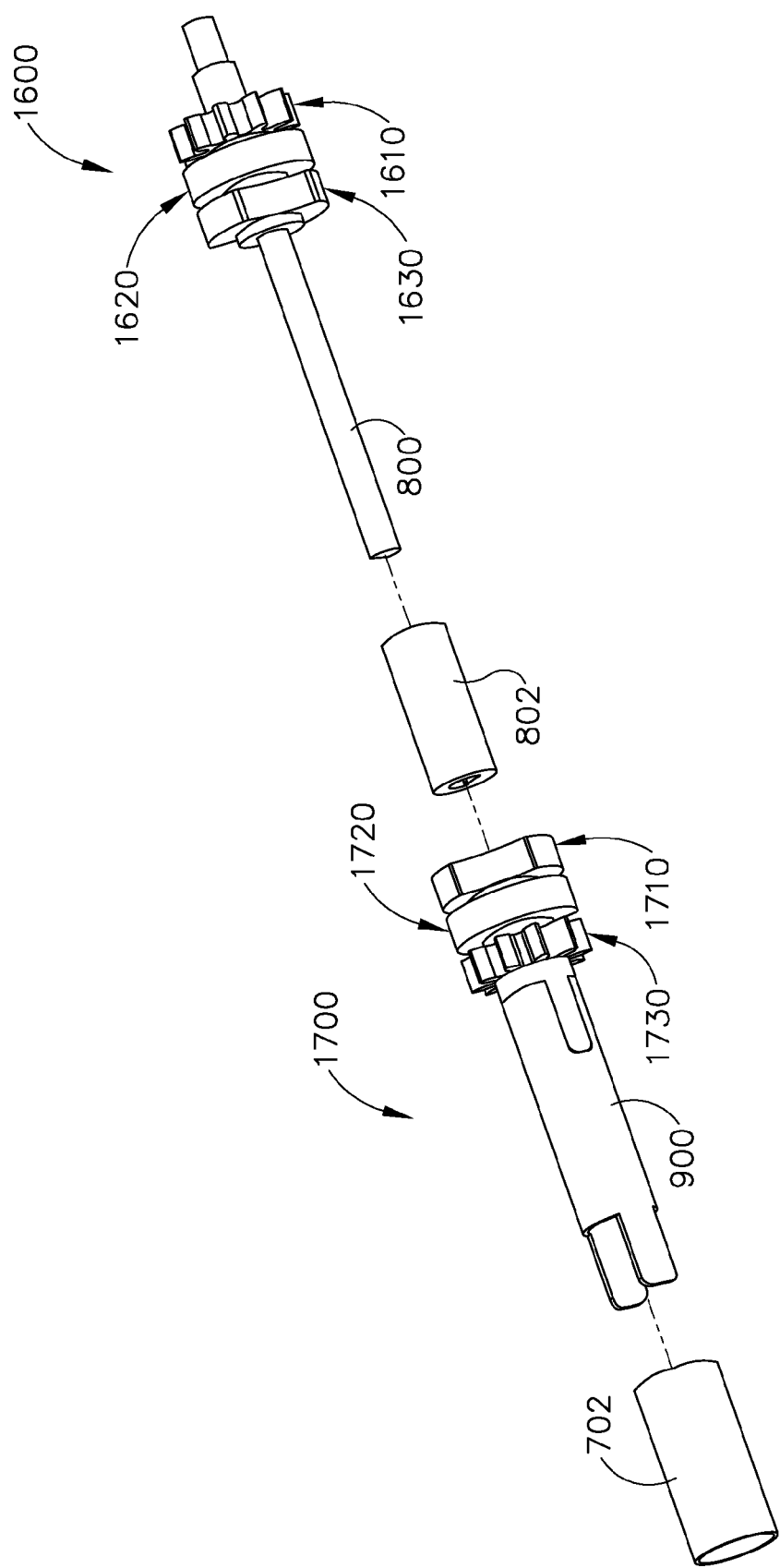
FIG. 18 depicts an exploded perspective view of a sub-assembly from the transmission assembly of FIG. 16.
Figure 19:
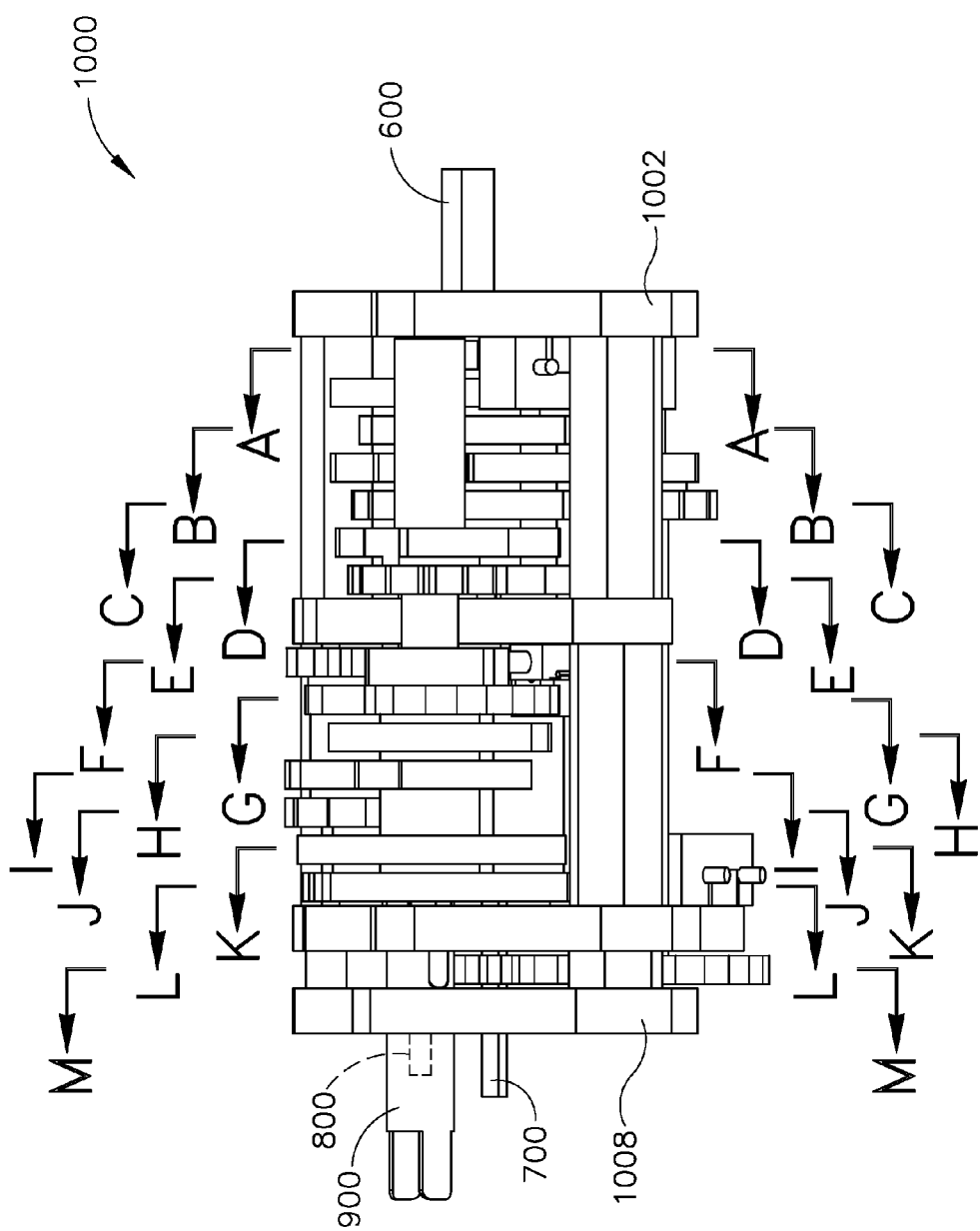
FIG. 19 depicts a side elevational view of the transmission assembly of FIG. 16.

Output shaft (800) is coupled to drive member (510), which is integrally coupled with drive shaft (284) and is thereby operable to rotate drive shaft (284) as described above. In particular, output shaft (800) is coupled with drive member (510) by a sleeve (802), which is disposed within output shaft (900), about the distal end of output shaft (800) and about the proximal end of drive member (510) as shown in FIG. 18. Output shaft (800) and drive member (510) each have a similar cross section resembling a circle with a chord section removed to present a flat region. The inner bore of sleeve (802) includes a complementary profile to engage these flat regions, such that output shaft (800), sleeve (802), and drive member (510) rotate together unitarily. By way of example only, output shaft (800) and/or drive member (510) may be further secured to sleeve (802) by a press-fit, using an adhesive, by a set screw, and/or in any other suitable fashion. As another merely illustrative example, output shaft (800) and/or drive member (510) may be may be permitted to slide longitudinally relative to sleeve (802) to some degree (e.g., to accommodate longitudinal displacement produced by deformations resulting from intentional overdrive, etc.). Various other suitable ways in which output shaft (800) may be coupled with drive member (510) will be apparent to those of ordinary skill in the art in view of the teachings herein.

Figure 16:
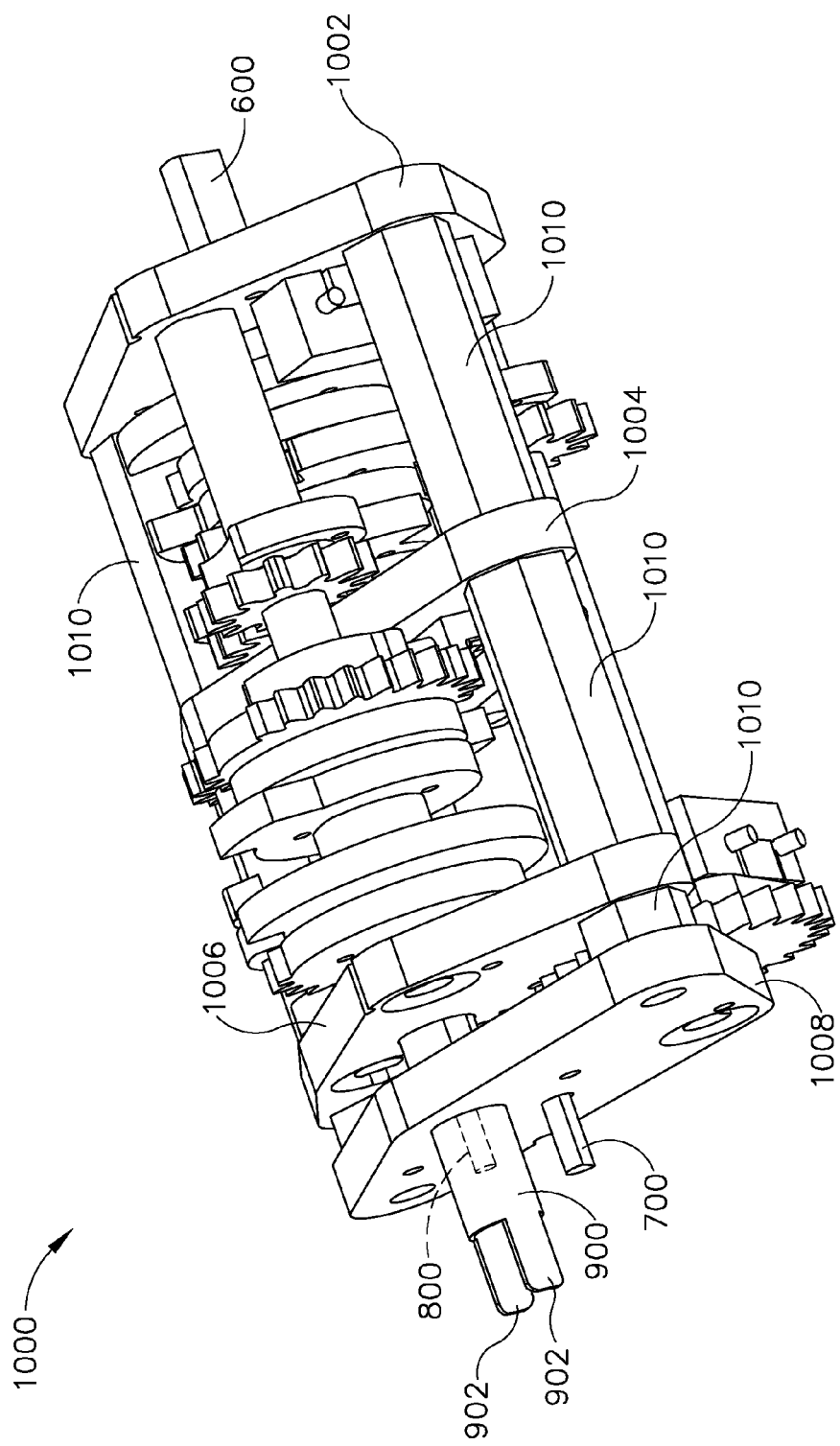
FIG. 16 depicts a perspective view of the transmission assembly from the drive assembly of FIG. 15.
Figure 17:
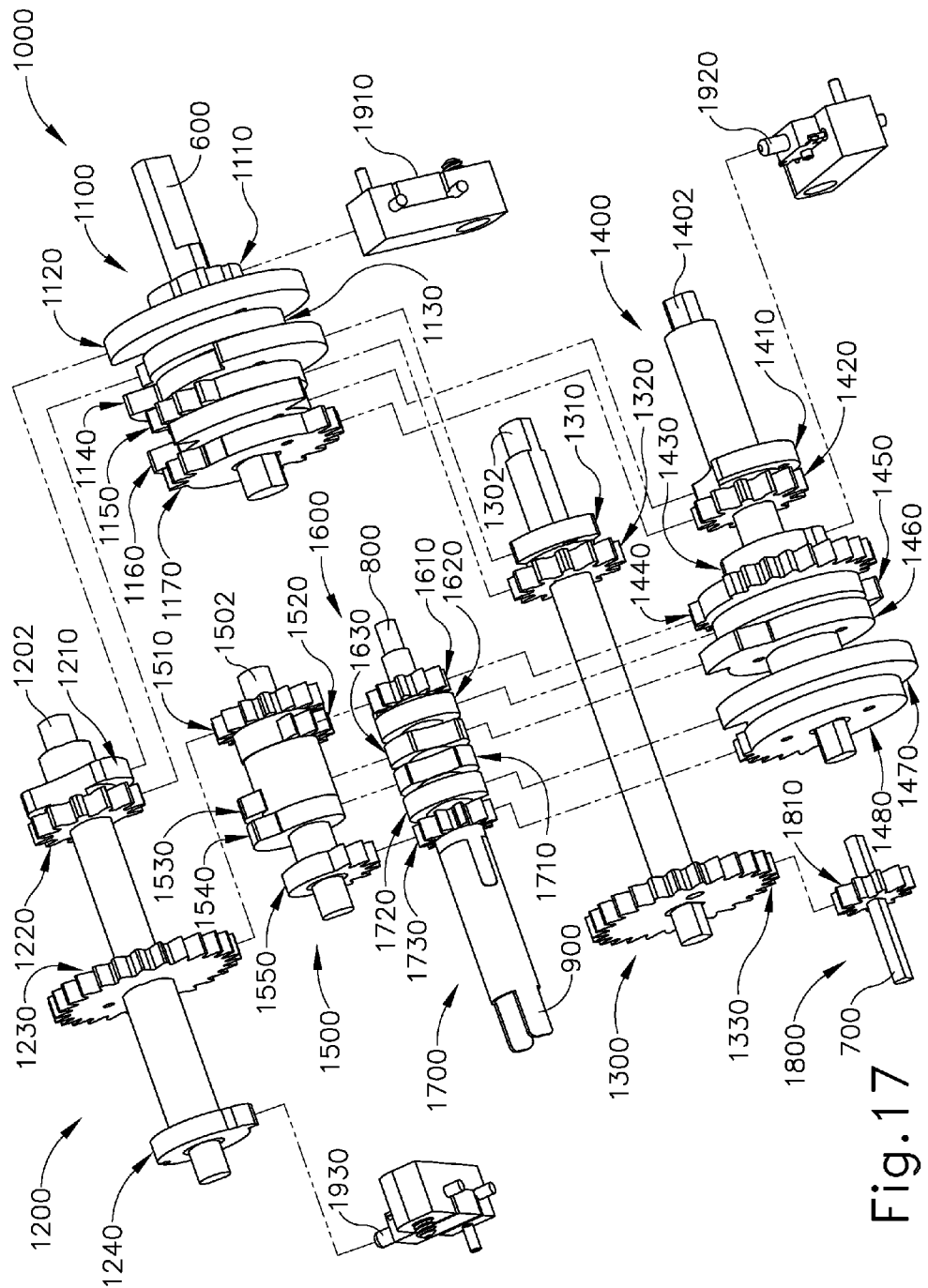
FIG. 17 depicts an exploded perspective view of the transmission assembly of FIG. 16.

Output shaft (900) is coupled to hollow shaft (280) at cutout portion (506) and is thereby operable to rotate hollow shaft (280). In particular, output shaft (900) has a pair of distally extending arms (902) as shown in FIGS. 16-18. Arms (902) are received in the first rectangular portions of cutout portion (506) formed at proximal end (478) of hollow shaft (280). As shown in FIG. 15, a sleeve (904) is positioned about this coupling between arms (902) and cutout portion (506) to substantially prevent arms (902) from deflecting outwardly and out of engagement with cutout portion (506) of hollow shaft (280). Sleeve (802) described above (as coupling output shaft (800) with drive member (510)) extends into the longitudinal region associated with the coupling between output shaft (900) and hollow shaft, such that sleeve (802) substantially prevent arms (902) from deflecting inwardly and out of engagement with cutout portion (506) of hollow shaft (280). By way of example only, output shaft (900) and/or hollow shaft (280) may be further secured to sleeve (904) by a press-fit, using an adhesive, by a set screw, and/or in any other suitable fashion. As another merely illustrative example, output shaft (900) and/or hollow shaft (280) may be may be permitted to slide longitudinally relative to sleeve (904) to some degree (e.g., to accommodate longitudinal displacement produced by deformations resulting from intentional overdrive, etc.). Various other suitable ways in which output shaft (900) may be coupled with hollow shaft (280) will be apparent to those of ordinary skill in the art in view of the teachings herein. It should also be understood that output shaft (800) and sleeve (802) are operable to rotate freely within output shaft (900) in the present example.

As best seen in FIG. 17, transmission assembly (1000) of the present example comprises a plurality of shaft assemblies (1100, 1200, 1300, 1400, 1500, 1600, 1700, 1800). FIG. 17 also shows a plurality of limit switches (1910, 1920, 1930) that are in communication with transmission assembly as will be described in greater detail below. Referring back to FIG. 16, transmission assembly (1000) also includes frame plates (1002, 1004, 1006, 1008) and spacer posts (1010). Frame plates (1002, 1004, 1006, 1008) are configured to support and maintain the proper orientation and spacing of shaft assemblies (1100, 1200, 1300, 1400, 1500, 1600, 1700, 1800). Spacer posts (1010) are configured to secure and maintain the proper positioning of frame plates (1002, 1004, 1006, 1008). Frame plates (1002, 1004, 1006, 1008) and spacer posts (1010) may be formed of metal and/or any other suitable material(s). Other suitable alternatives and variations for frame plates (1002, 1004, 1006, 1008) and spacer posts (1010) will be apparent to those of ordinary skill in the art in view of the teachings herein.

A. Exemplary Shaft Assembly Features

The following describes exemplary features of shaft assemblies (1100, 1200, 1300, 1400, 1500, 1600, 1700, 1800). It should be understood, though, that shaft assemblies (1100, 1200, 1300, 1400, 1500, 1600, 1700, 1800) could instead be configured in numerous other ways. Other suitable features and configurations will be apparent to those of ordinary skill in the art in view of the teachings herein.

Figure 20A:
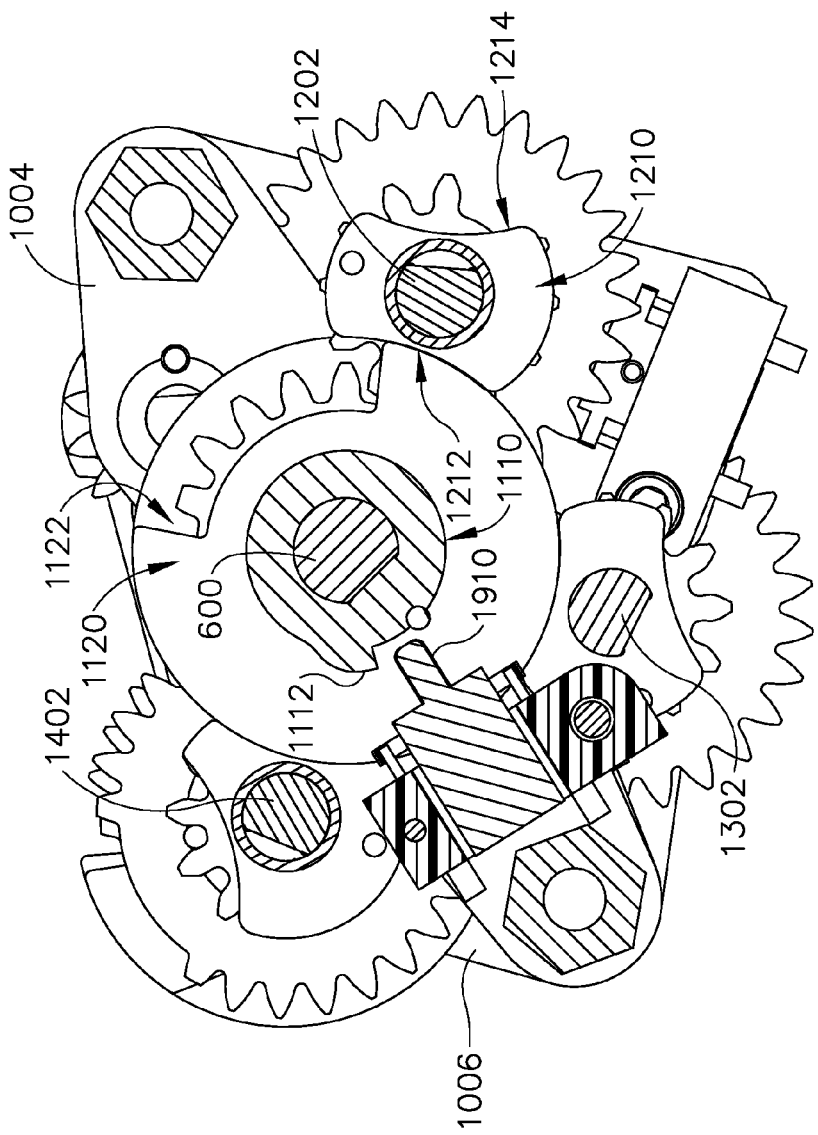
FIG. 20A depicts a cross-sectional view of the transmission assembly of FIG. 16, taken along line A-A of FIG. 19, with the transmission assembly at a first stage of operation.
Figure 20B:
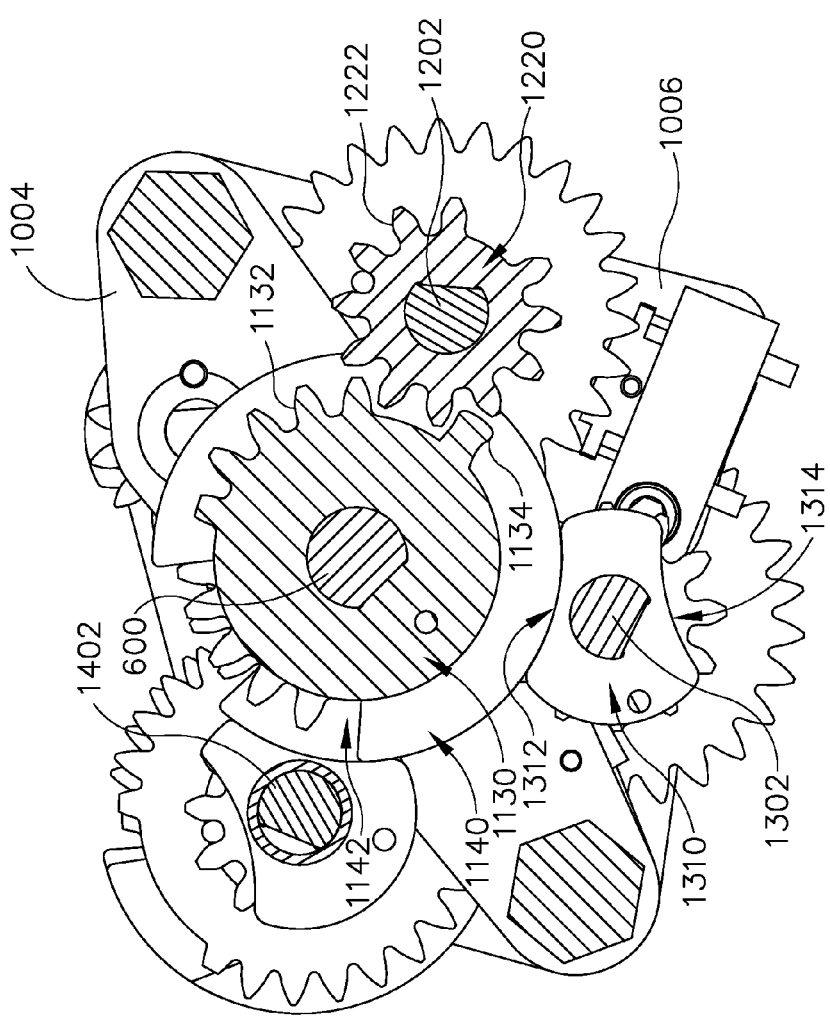
FIG. 20B depicts a cross-sectional view of the transmission assembly of FIG. 16, taken along line B-B of FIG. 19, with the transmission assembly at the first stage of operation.
Figure 20C:
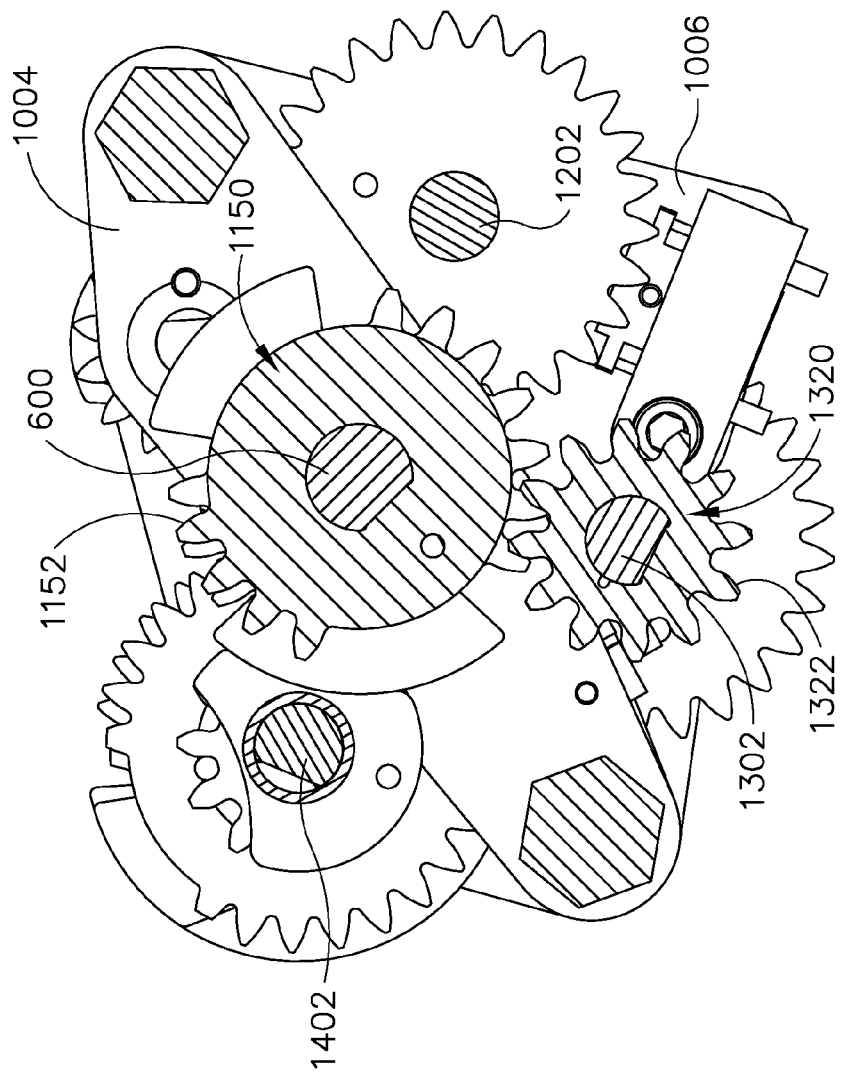
FIG. 20C depicts a cross-sectional view of the transmission assembly of FIG. 16, taken along line C-C of FIG. 19, with the transmission assembly at the first stage of operation.
Figure 20D:
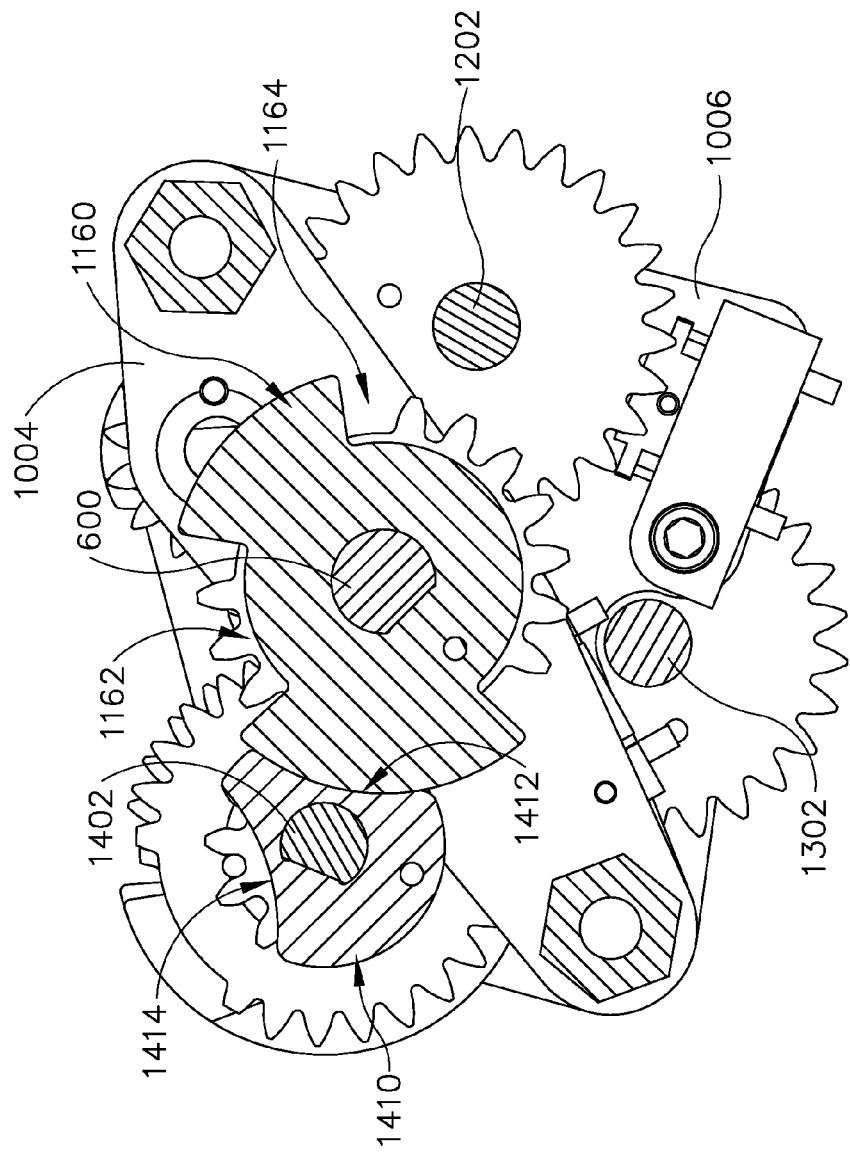
FIG. 20D depicts a cross-sectional view of the transmission assembly of FIG. 16, taken along line D-D of FIG. 19, with the transmission assembly at the first stage of operation.
Figure 20E:
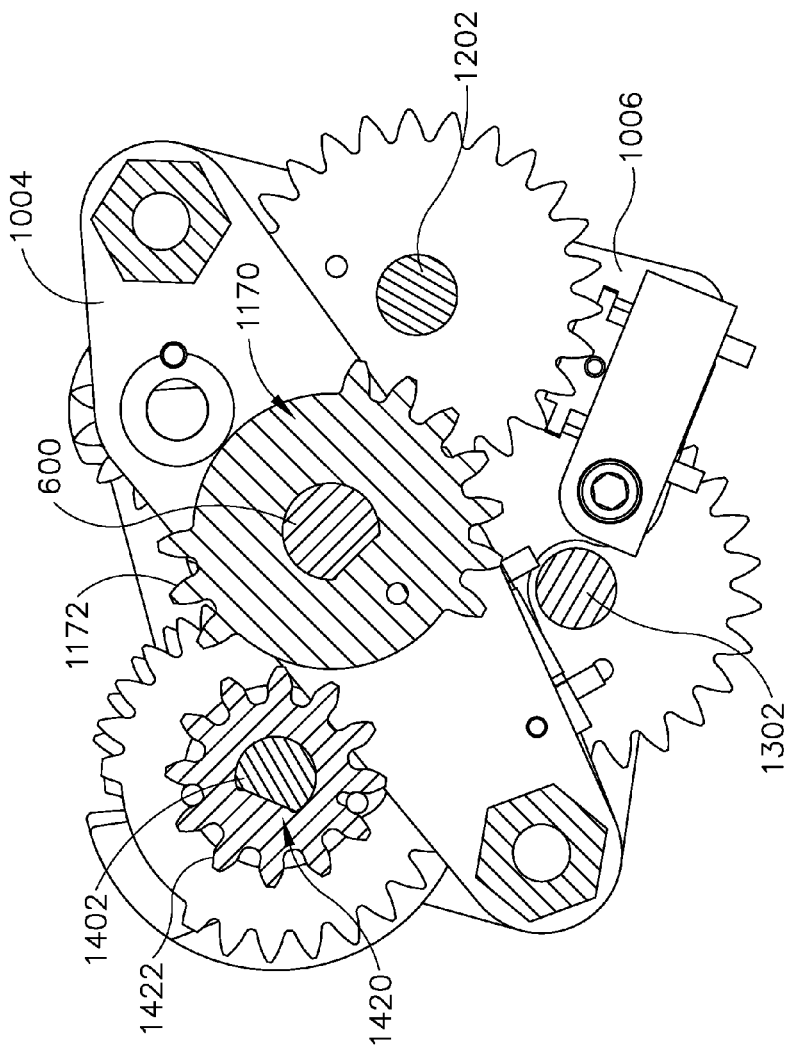
FIG. 20E depicts a cross-sectional view of the transmission assembly of FIG. 16, taken along line E-E of FIG. 19, with the transmission assembly at the first stage of operation.

Referring again to FIG. 17, shaft assembly (1100) comprises input shaft (600), a first rotary cam (1110), a second rotary cam (1120), a first sector gear (1130), a third rotary cam (1140), a second sector gear (1150), a fourth rotary cam (1160), and a third sector gear (1170). Cams (1110, 1120, 1140, 1160) and gears (1130, 1150, 1170) are all positioned between frame plate (1002) and frame plate (1004); and all rotate unitarily with input shaft (600). As best seen in FIG. 20A, first rotary cam (1110) includes a protrusion (1112) extending outwardly. Protrusion (1112) selectively engages limit switch (1910) during operation of transmission assembly (1000) as will be described in greater detail below. Limit switch (1910) is in communication with a control module (not shown) and provides a signal to the control module when protrusion (1112) engages limit switch (1910). As also seen in FIG. 20A, second rotary cam (1120) includes a recessed region (1122) spanning an acute angular range of the outer perimeter of second rotary cam (1120). As best seen in FIG. 20B, first sector gear (1130) includes a set of teeth (1132) spanning an acute angular range of the outer perimeter of first sector gear (1130); and a separate single tooth (1134) angularly spaced from teeth (1132). As also seen in FIG. 20B, third rotary cam (1140) includes a recessed region (1142) spanning an acute angular range of the outer perimeter of third rotary cam (1140). As best seen in FIG. 20C, second sector gear (1150) includes a set of teeth (1152) spanning an acute angular range of the outer perimeter of second sector gear (1150). As best seen in FIG. 20D, fourth rotary cam (1160) includes a first recessed region (1162) spanning an acute angular range of the outer perimeter of fourth rotary cam (1160); and a second recessed region (1164) spanning an obtuse angular range of the outer perimeter of fourth rotary cam (1160). As best seen in FIG. 20E, third sector gear (1170) includes a first set of teeth (1172) spanning an acute angular range of the outer perimeter of third sector gear (1170); and a separate second set of teeth (1174) spanning an obtuse angular range of the outer perimeter of third sector gear (1170). As will be described in greater detail below, features of shaft assembly (1100) directly engage features of shaft assemblies (1200, 1300, 1400) during operation of transmission assembly (1000).

Figure 20F:
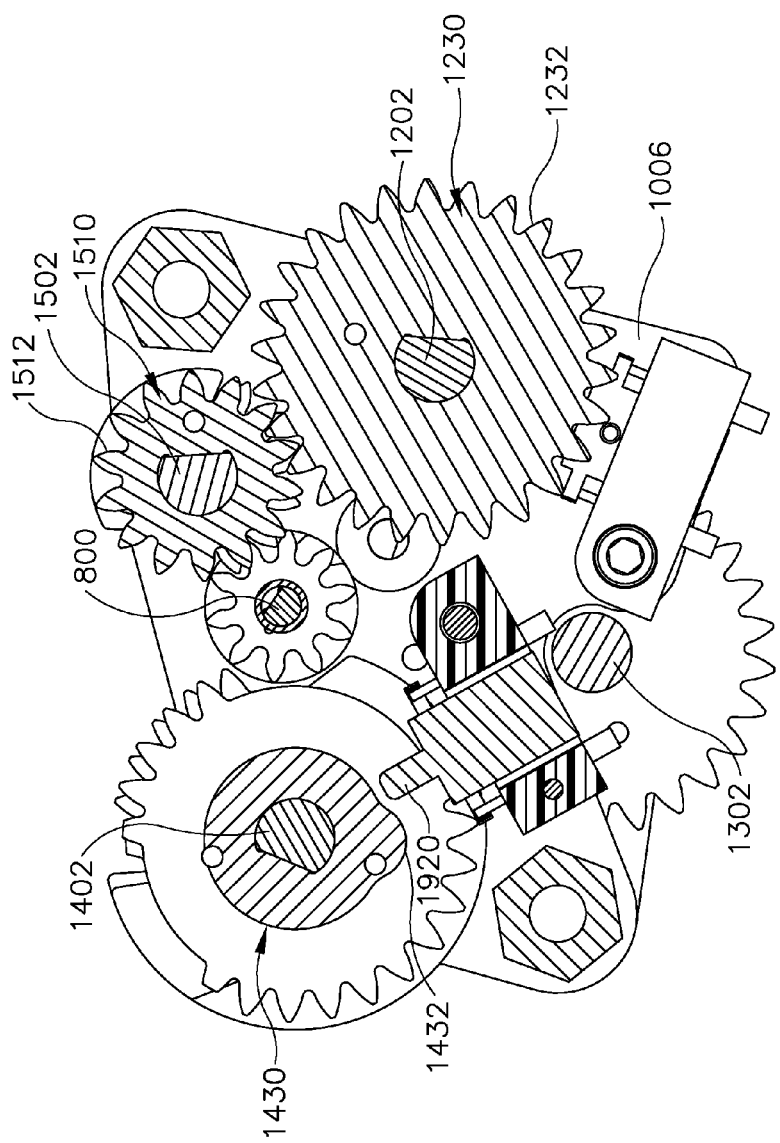
FIG. 20F depicts a cross-sectional view of the transmission assembly of FIG. 16, taken along line F-F of FIG. 19, with the transmission assembly at the first stage of operation.
Figure 20G:
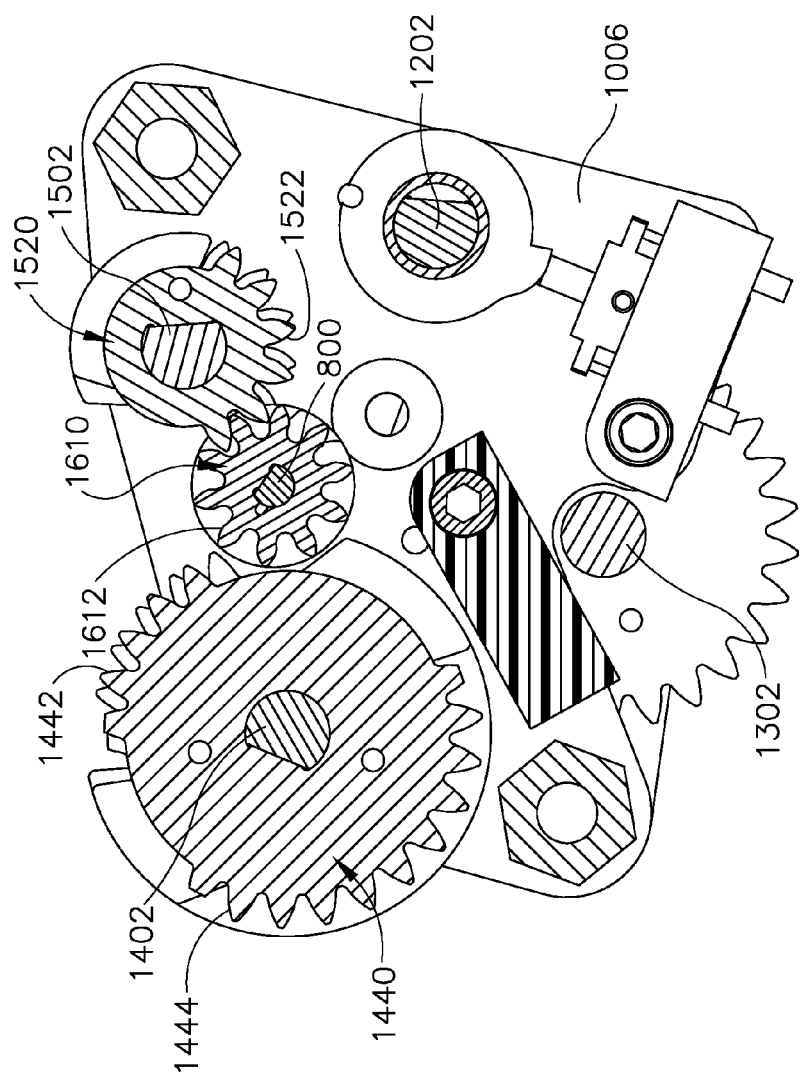
FIG. 20G depicts a cross-sectional view of the transmission assembly of FIG. 16, taken along line G-G of FIG. 19, with the transmission assembly at the first stage of operation.
Figure 20H:
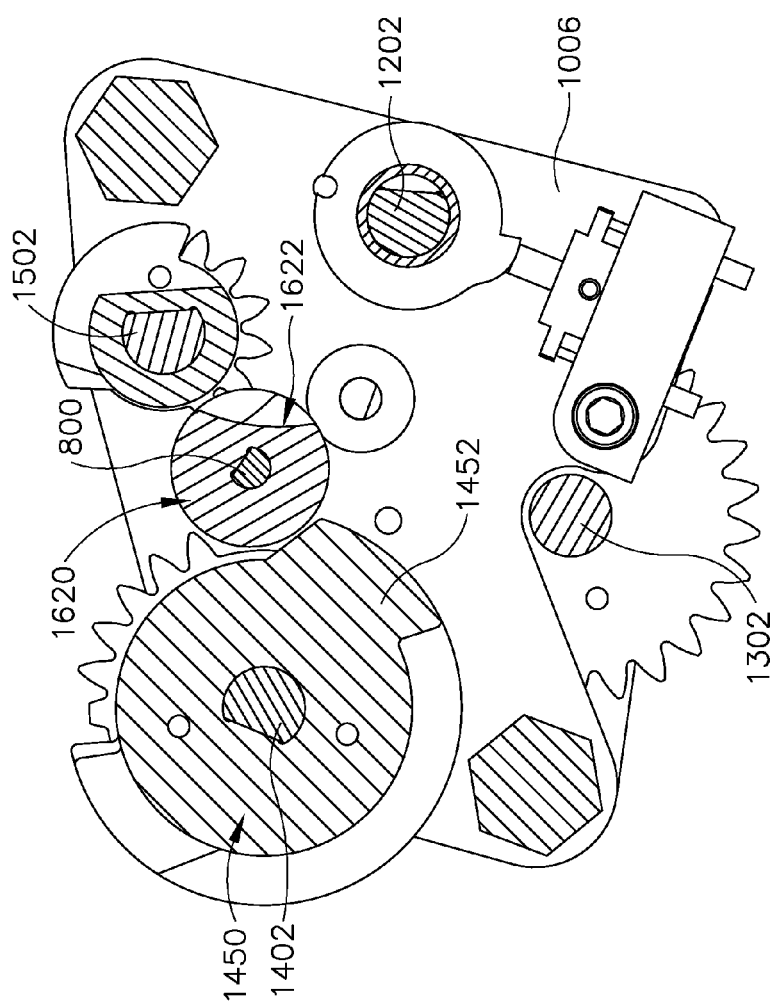
FIG. 20H depicts a cross-sectional view of the transmission assembly of FIG. 16, taken along line H-H of FIG. 19, with the transmission assembly at the first stage of operation.
Figure 20I:
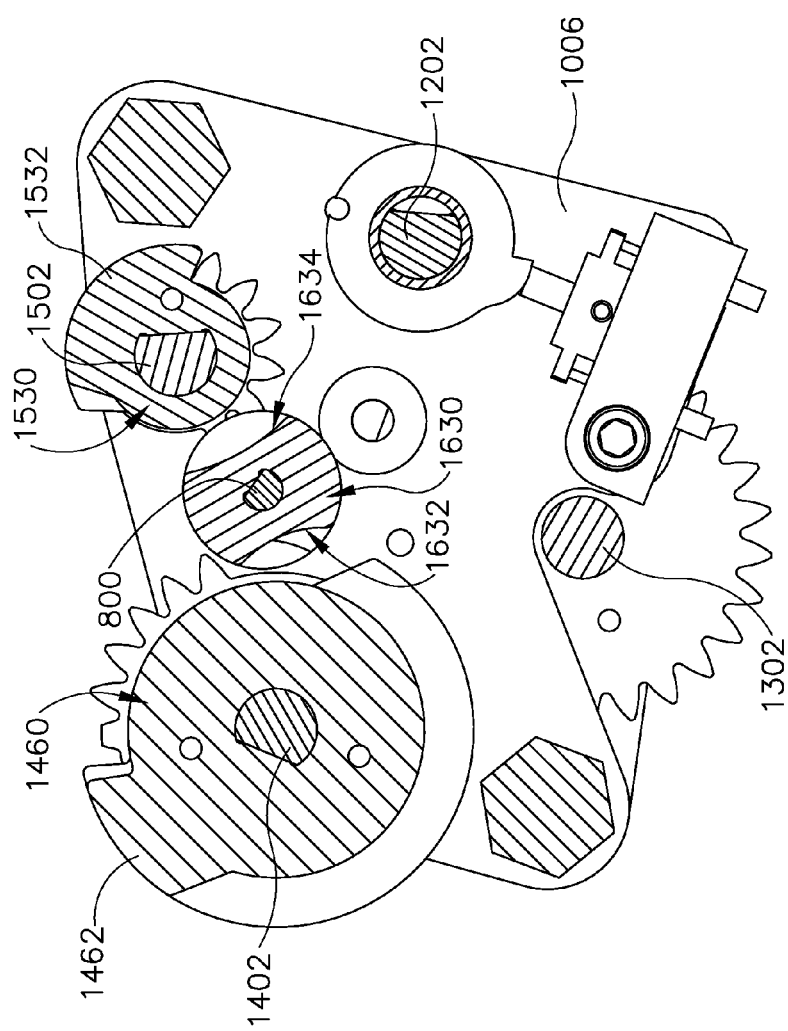
FIG. 20I depicts a cross-sectional view of the transmission assembly of FIG. 16, taken along line I-I of FIG. 19, with the transmission assembly at the first stage of operation.
Figure 20J:
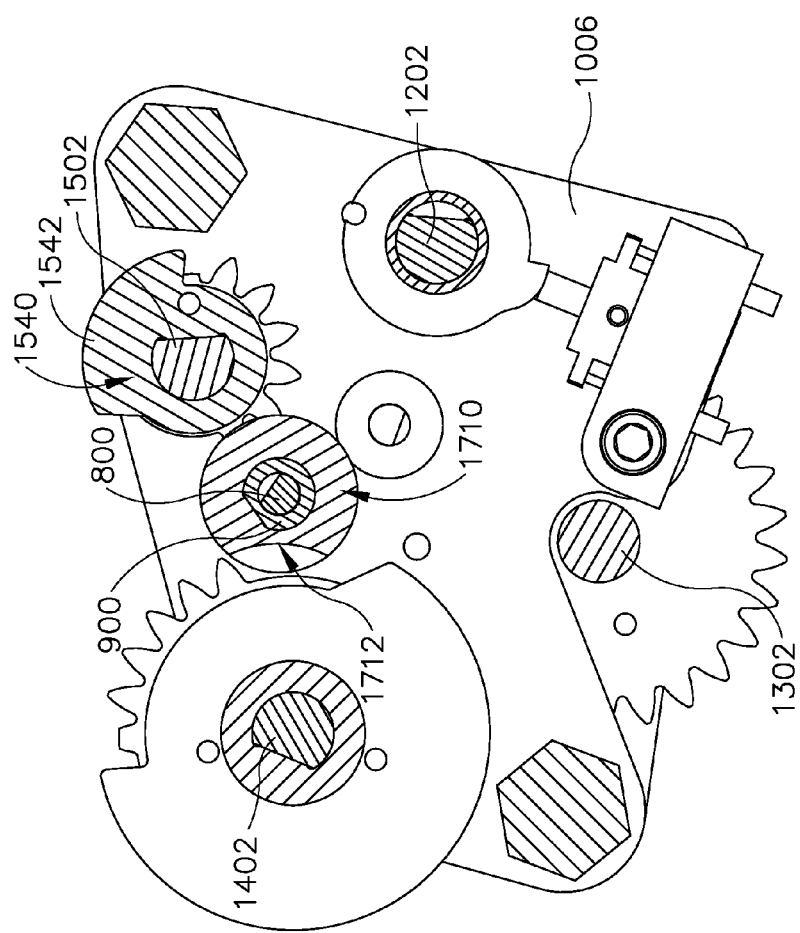
FIG. 20J depicts a cross-sectional view of the transmission assembly of FIG. 16, taken along line J-J of FIG. 19, with the transmission assembly at the first stage of operation.
Figure 20K:
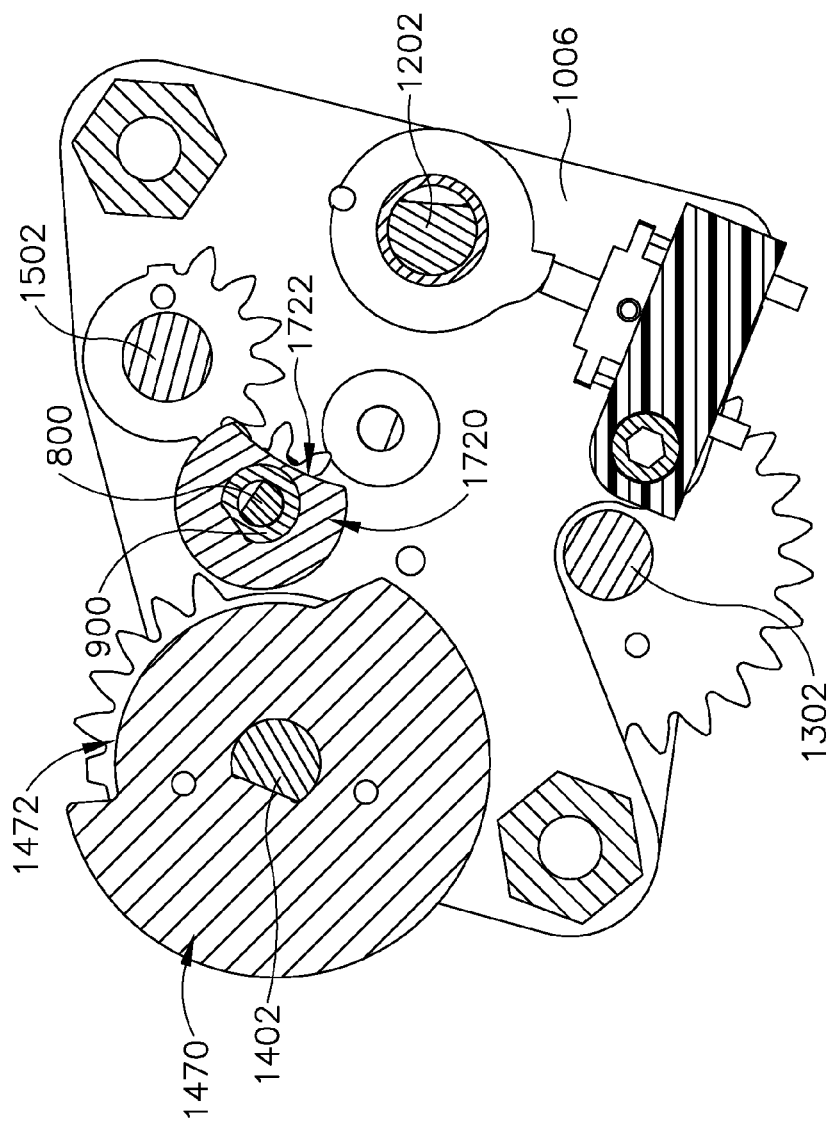
FIG. 20K depicts a cross-sectional view of the transmission assembly of FIG. 16, taken along line K-K of FIG. 19, with the transmission assembly at the first stage of operation.
Figure 20L:
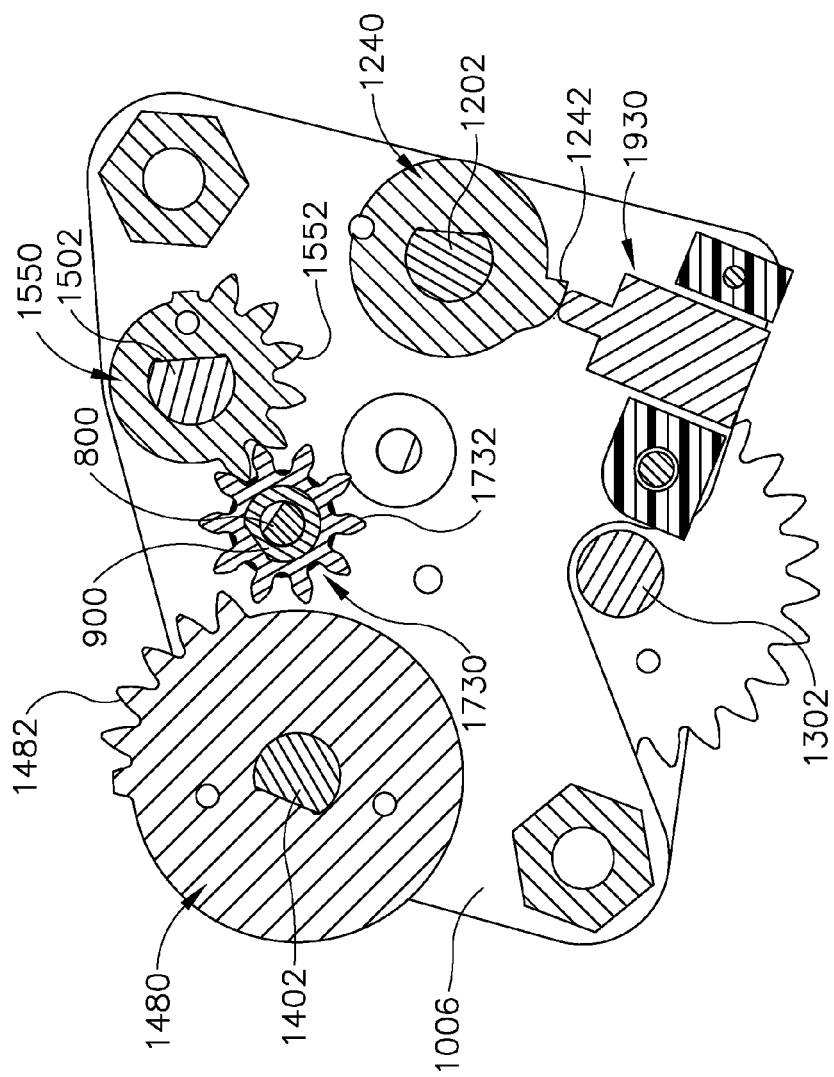
FIG. 20L depicts a cross-sectional view of the transmission assembly of FIG. 16, taken along line L-L of FIG. 19, with the transmission assembly at the first stage of operation.

Shaft assembly (1200) comprises an idler shaft (1202), a first rotary cam (1210), a sector gear (1220), a spur gear (1230), and a second rotary cam (1240). First rotary cam (1210) and sector gear (1220) are positioned between frame plate (1002) and frame plate (1004). Spur gear (1230) and second rotary cam (1240) are positioned between frame plate (1004) and frame plate (1006). Gears (1220, 1230) and cam (1240) all rotate unitarily with idler shaft (1202). As best seen in FIG. 20A, first rotary cam (1210) includes a first arcuate recess (1212) and a second arcuate recess (1214). As best seen in FIG. 20B, sector gear (1220) includes a set of teeth (1222) spanning a reflexive angular range of the outer perimeter of sector gear (1220). As best seen in FIG. 20F, spur gear (1230) includes a set of teeth (1232) spanning the full angular range of the outer perimeter of spur gear (1220). As best seen in FIG. 20L, second rotary cam (1240) includes an outwardly extending protrusion (1242), which selectively engages limit switch (1930) during operation of transmission assembly (1000). Limit switch (1930) is in communication with a control module (not shown) and provides a signal to the control module when protrusion (1242) engages limit switch (1930). As will be described in greater detail below, features of shaft assembly (1200) directly engage features of shaft assemblies (1100, 1500) during operation of transmission assembly (1000).

Figure 20M:
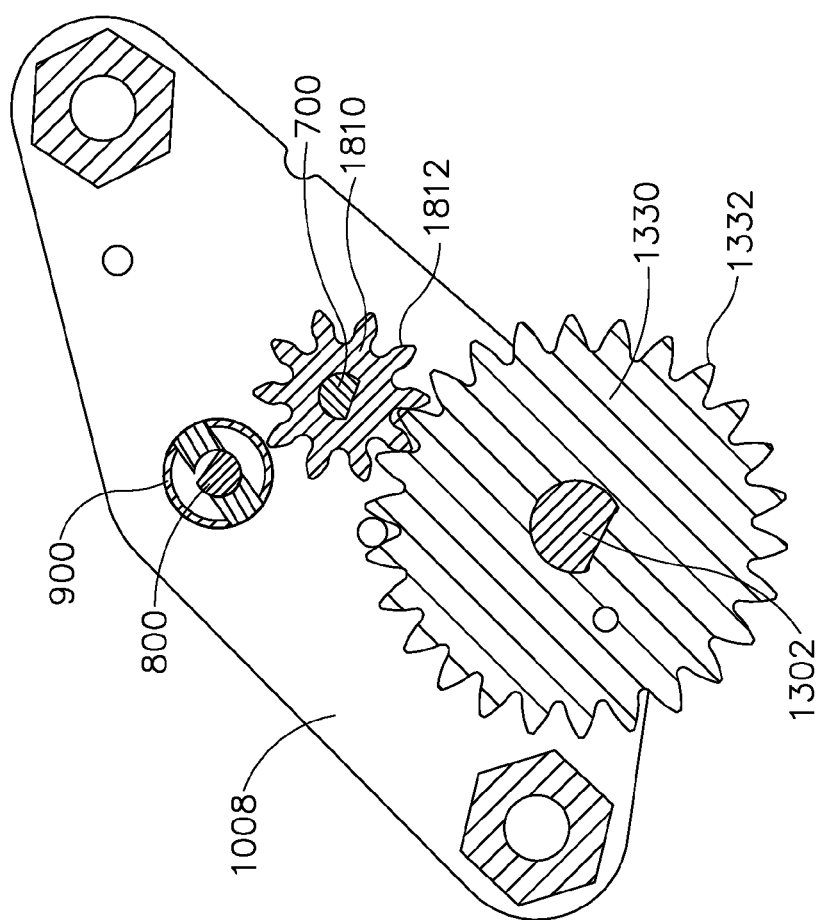
FIG. 20M depicts a cross-sectional view of the transmission assembly of FIG. 16, taken along line M-M of FIG. 19, with the transmission assembly at the first stage of operation.

Shaft assembly (1300) comprises an idler shaft (1302), a first rotary cam (1310), a first spur gear (1320), and a second spur gear (1330). First rotary cam (1310) and first spur gear (1320) are positioned between frame plate (1002) and frame plate (1004). Second spur gear (1330) is positioned between frame plate (1006) and frame plate (1008). Cam (1310) and gears (1320, 1330) all rotate unitarily with idler shaft (1302). As best seen in FIG. 20B, first rotary cam (1310) includes a first arcuate recess (1312) and a second arcuate recess (1314). As best seen in FIG. 20C, first spur gear (1320) includes a set of teeth (1322) spanning the full angular range of the outer perimeter of first spur gear (1320). As best seen in FIG. 20M, second spur gear (1330) includes a set of teeth (1332) spanning the full angular range of the outer perimeter of second spur gear (1330). As will be described in greater detail below, features of shaft assembly (1300) directly engage features of shaft assemblies (1100, 1800) during operation of transmission assembly (1000).

Shaft assembly (1400) comprises an idler shaft (1402), a first rotary cam (1410), a spur gear (1420), a second rotary cam (1430), a first sector gear (1440), a third rotary cam (1450), a fourth rotary cam (1460), a fifth rotary cam (1470), and a second sector gear (1480). First rotary cam (1410) and spur gear (1420) are positioned between frame plate (1002) and frame plate (1004). Cams (1430, 1450, 1460, 1470) and gears (1440, 1480) are positioned between frame plate (1004) and frame plate (1006). Cams (1410, 1430, 1450, 1460, 1470) and gears (1420, 1440, 1480) all rotate unitarily with idler shaft (1402). As best seen in FIG. 20D, first rotary cam (1410) includes a first arcuate recess (1412) and a second arcuate recess (1414). As best seen in FIG. 20E, spur gear (1420) includes a set of teeth (1422) spanning the full angular range of the outer perimeter of spur gear (1420). As best seen in FIG. 20F, second rotary cam (1430) includes an outwardly extending protrusion (1432), which selectively engages limit switch (1920) during operation of transmission assembly (1000). Limit switch (1920) is in communication with a control module (not shown) and provides a signal to the control module when protrusion (1432) engages limit switch (1920). As best seen in FIG. 20G, first sector gear (1440) includes a first set of teeth (1442) spanning an acute angular range of the outer perimeter of first sector gear (1440); and a separate second set of teeth (1444) spanning an obtuse angular range of the outer perimeter of first sector gear. As best seen in FIG. 20H, third rotary cam (1450) includes an outwardly extending protrusion (1452). Similarly, as best seen in FIG. 20I, fourth rotary cam (1460) includes an outwardly extending protrusion (1462). As best seen in FIG. 20K, fifth rotary cam (1470) includes a recess (1472) spanning an obtuse angular range of the outer perimeter of fifth rotary cam (1470). As best seen in FIG. 20L, second sector gear (1480) includes a set of teeth (1482) spanning an acute angular range of the outer perimeter of second sector gear (1480). As will be described in greater detail below, features of shaft assembly (1400) directly engage features of shaft assemblies (1100, 1600, 1700) during operation of transmission assembly (1000).

Shaft assembly (1500) comprises an idler shaft (1502), a spur gear (1510), a first sector gear (1520), a first rotary cam (1530), a second rotary cam (1540), and a second sector gear (1550). Gears (1510, 1520, 165) and cams (1530, 1540) are all positioned between frame plate (1004) and frame plate (1006); and all rotate unitarily with idler shaft (1502). As best seen in FIG. 20F, spur gear (1510) includes a set of teeth (1512) spanning the full angular range of the outer perimeter of spur gear (1510). As best seen in FIG. 20G, first sector gear (1520) includes a set of teeth (1522) spanning an obtuse angular range of the outer perimeter of first sector gear (1520). As best seen in FIG. 20I, first rotary cam (1530) includes a protrusion (1532) spanning an obtuse angular range of the outer perimeter of first rotary cam (1530). As best seen in FIG. 20J, second rotary cam (1540) also includes a protrusion (1542) spanning an obtuse angular range of the outer perimeter of second rotary cam (1540). As best seen in FIG. 20L, second sector gear (1550) includes a set of teeth (1552) spanning an obtuse angular range of the outer perimeter of second sector gear (1550). As will be described in greater detail below, features of shaft assembly (1500) directly engage features of shaft assemblies (1200, 1600, 1700) during operation of transmission assembly (1000).

As best seen in FIG. 18, shaft assembly (1600) comprises output shaft (800), spur gear (1610), a first rotary cam (1620), and a second rotary cam (1630). Gear (1610) and cams (1620, 1630) are all positioned between frame plate (1004) and frame plate (1006); and all rotate unitarily with output shaft (800). As best seen in FIG. 20G, spur gear (1610) includes a set of teeth (1612) spanning the full angular range of the outer perimeter of spur gear (1610). As best seen in FIG. 20H, first rotary cam (1620) includes an arcuate recess (1622). As best seen in FIG. 20I, second rotary cam (1630) includes a first arcuate recess (1632) and a second arcuate recess (1634). It should be understood that shaft assembly (1600) and shaft assembly (1700) are positioned along a common axis; and that output shaft (800) extends longitudinally through a portion of shaft assembly (1700). It should also be understood that output shaft (800) (and the rest of shaft assembly (1600)) is rotatable relative to shaft assembly (1700). As will be described in greater detail below, features of shaft assembly (1600) directly engage features of shaft assemblies (1400, 1500) during operation of transmission assembly (1000).

Shaft assembly (1700) comprises output shaft (900), a first rotary cam (1710), a second rotary cam (1720), and a spur gear (1730). Cams (1710, 1720) and gear (1730) are all positioned between frame plate (1004) and frame plate (1006); and all rotate unitarily with output shaft (900). It should be understood that output shaft (900) includes a neck-down region (906) where its outer diameter is reduced to fit within cams (1710, 1720) and gear (1730). As best seen in FIG. 20J, first rotary cam (1710) includes an arcuate recess (1712). As best seen in FIG. 20K, second rotary cam (1720) also includes an arcuate recess (1722). As best seen in FIG. 20L, spur gear (1730) includes a set of teeth (1732) spanning the full angular range of the outer perimeter of spur gear (1730). As will be described in greater detail below, features of shaft assembly (1700) directly engage features of shaft assemblies (1400, 1500) during operation of transmission assembly (1000).

Shaft assembly (1800) comprises output shaft (700) and a spur gear (1810). Spur gear (1810) is positioned between frame plate (1006) and frame plate (1008); and rotates unitarily with output shaft (7000). Spur gear (1810) includes a set of teeth (1812) spanning the full angular range of the outer perimeter of spur gear (1810). As will be described in greater detail below, features of shaft assembly (1800) directly engage features of shaft assembly (1800) during operation of transmission assembly (1000).

B. Exemplary Operation of Transmission Assembly

The following describes exemplary interactions between features of shaft assemblies (1100, 1200, 1300, 1400, 1500, 1600, 1700, 1800) and resulting operations of transmission assembly (1000). It should be understood, though, that shaft assemblies (1100, 1200, 1300, 1400, 1500, 1600, 1700, 1800) could instead interact in various other ways; and that transmission assembly (1000) could operate in other ways. Other suitable types of interactions and operations will be apparent to those of ordinary skill in the art in view of the teachings herein.

1. Driving Needle Through Tissue

As described above, during operation of surgical instrument (10) as shown in FIGS. 8A-8B, end effector (200) is rotated about axis (130) to drive needle (50) through tissue layers (300, 302) while arm (210) grasps needle (50). The components of transmission assembly (1000) are configured as shown in FIGS. 20A-20M during this operation of end effector (200). In particular, motor (28) is inactive at this state, such that input shaft (600) and the rest of shaft assembly (1100) remain stationary. As shown in FIG. 20A, second rotary cam (1120) of shaft assembly (1100) is engaged with first arcuate recess (1214) of first rotary cam (1210), thereby holding shaft assembly (1200) stationary. As best seen in FIG. 20B, third rotary cam (1140) of shaft assembly (1100) is engaged with first arcuate recess (1312) of first rotary cam (1312), thereby holding shaft assembly (1300) stationary. As best seen in FIG. 20D, fourth rotary cam (1160) of shaft assembly (1100) is engaged with first arcuate recess (1412) of first rotary cam (1410), thereby holding shaft assembly (1400) stationary. As shown in FIG. 20F, teeth (1232) of spur gear (1230) are engaged with teeth (1512) of spur gear (1510), thereby holding shaft assembly (1500) stationary. FIG. 20G shows teeth (1522) of first sector gear (1520) engaged with teeth (1612) of spur gear (1610), thereby holding output shaft (800) and the rest of shaft assembly (1600) stationary. Since output shaft (800) and drive shaft (284) are configured to rotate together unitarily as described above, it should be understood that drive shaft (284) is held stationary at this stage.

Continuing with the operational stages of end effector (200) depicted in FIGS. 8A-8B, FIG. 20L shows teeth (1552) of second sector gear (1550) engaged with teeth (1732) of spur gear (1730), thereby holding output shaft (900) and the rest of shaft assembly (1700) stationary. Since output shaft (900) and hollow shaft (280) are configured to rotate together unitarily as described above, it should be understood that hollow shaft (280) is held stationary at this stage. Since hollow shaft (280) and drive shaft (284) are both held stationary at this stage, it should be understood that the relative positioning of jaws (260, 270) is positively fixed at this stage. In particular, jaws (260, 270) are fixed in an open position at this stage in the present example. As shown in FIG. 20M, teeth (1332) of second spur gear (1330) engage teeth (1812) of spur gear (1810), thereby holding output shaft (700) stationary. Since output shaft (700) and drive shaft (244) are configured to rotate together unitarily as described above, it should be understood that drive shaft (244) is held stationary at this stage. As also described above, hollow shaft (240) is always held stationary throughout operation of suturing instrument (10) due to engagement between a boss of handle portion (20) and a notch (484) formed in the proximal end of hollow shaft (240). Since hollow shaft (240) and drive shaft (244) are both held stationary at this stage, it should be understood that the relative positioning of jaws (220, 230) is positively fixed at this stage. In particular, jaws (220, 230) are fixed in a closed position at this stage in the present example, firmly grasping needle (50).

Figure 21:
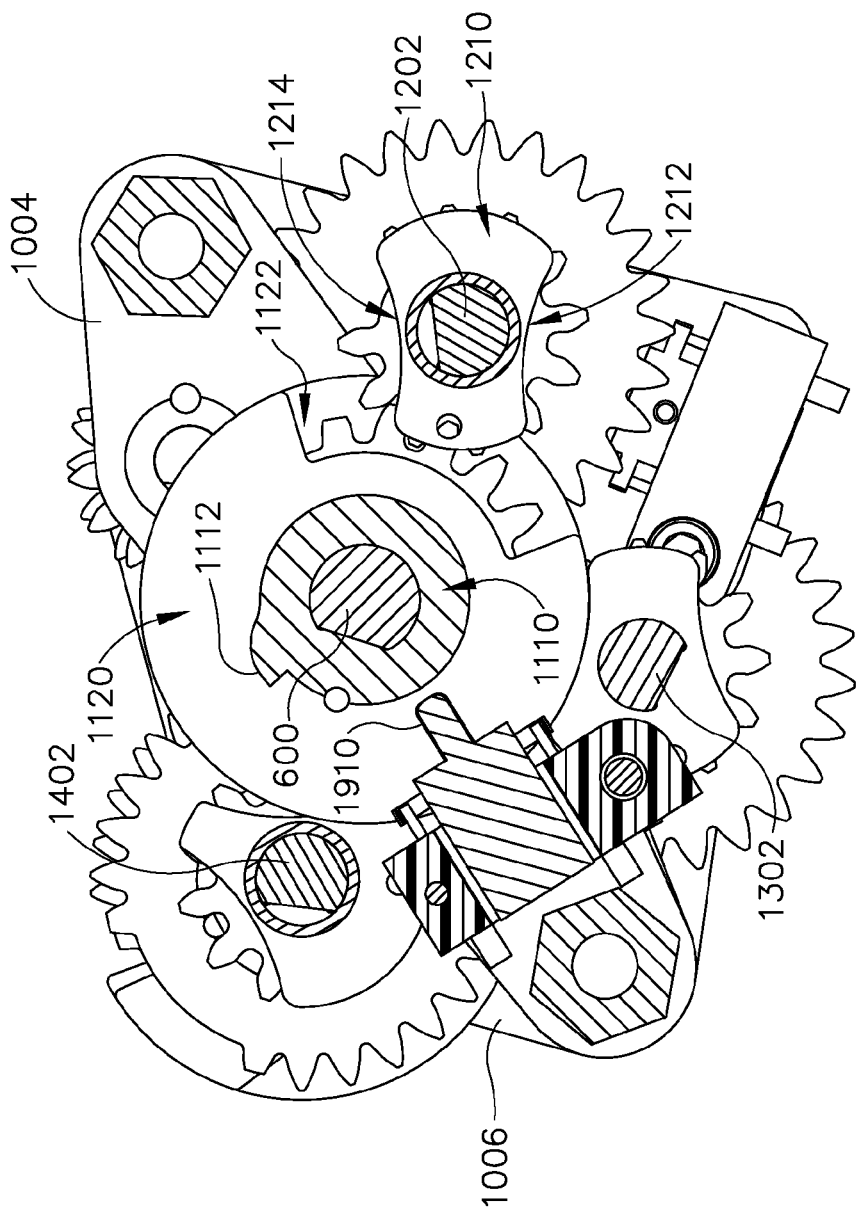
FIG. 21 depicts a cross-sectional view of the transmission assembly of FIG. 16, taken along line A-A of FIG. 19, with the transmission assembly at a second stage of operation.
Figure 22:
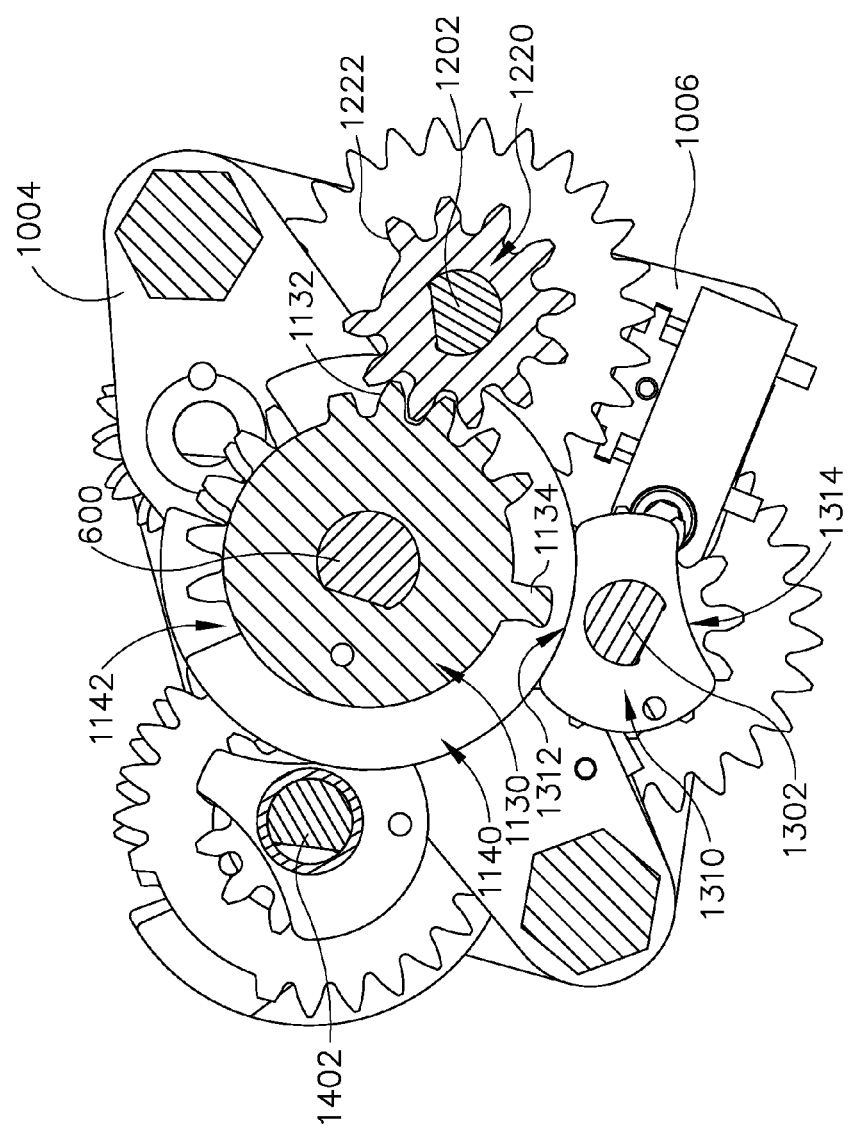
FIG. 22 depicts a cross-sectional view of the transmission assembly of FIG. 16, taken along line B-B of FIG. 19, with the transmission assembly at the second stage of operation.

2. Positioning Needle Receiving Arm for Receipt of Needle by Needle Receiving Arm Next, arm (250) is rotated about axis (140) from the position shown in FIG. 8B to the position shown in FIG. 8C, to position needle (50) between jaws (260, 270). The components of transmission assembly (1000) are actuated from the configuration shown in FIGS. 20A-20M to the configuration shown in FIGS. 21-31 to provide this motion of arm (250). In particular, motor (28) is activated to rotate input shaft (600) and the rest of shaft assembly (1100) clockwise (in the depicted views shown in FIGS. 21-31). As best seen in FIG. 21, this movement disengages second rotary cam (1120) from arcuate recess (1214) of first rotary cam (1210), such that recessed region (1122) of second rotary cam (1120) provides clearance for first rotary cam (1210) and the rest of shaft assembly (1200) to rotate as will be described below. However, as best seen in FIG. 22, third rotary cam (1140) remains engaged with first arcuate recess (1312) of first rotary cam (1312), thereby continuing to hold shaft assembly (1300) stationary at this stage. It should be understood that, due to the coupling between shaft assembly (1300) and output shaft (700) as described above, the relative positioning of jaws (220, 230) remains positively fixed at this stage, with jaws (220, 230) continuing to firmly grasp needle (50).

Figure 23:
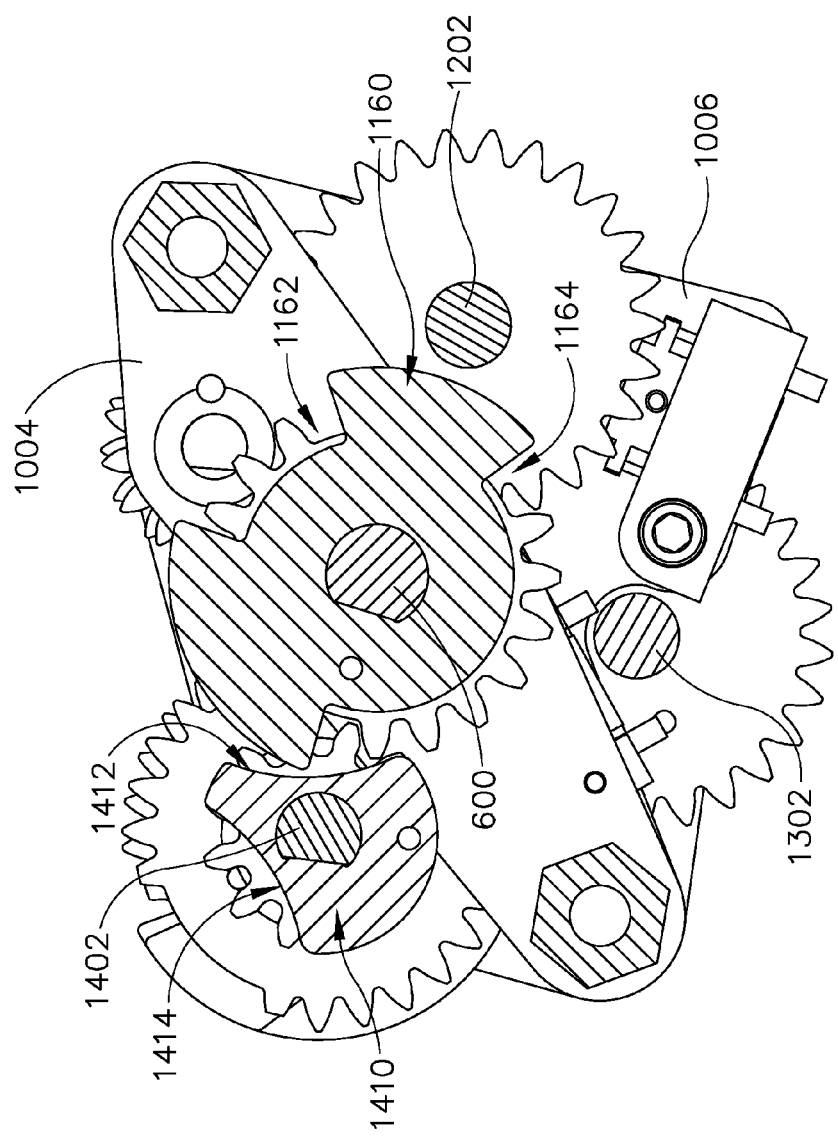
FIG. 23 depicts a cross-sectional view of the transmission assembly of FIG. 16, taken along line D-D of FIG. 19, with the transmission assembly at the second stage of operation.
Figure 24:
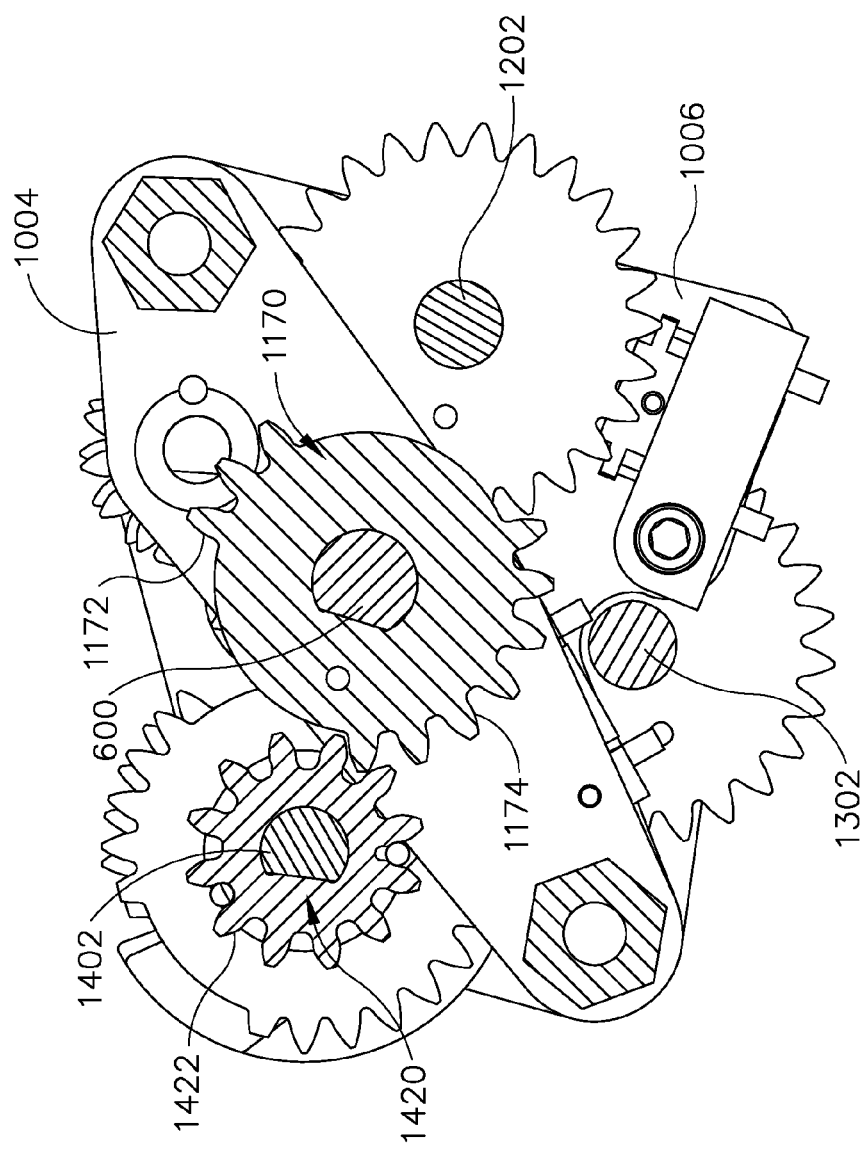
FIG. 24 depicts a cross-sectional view of the transmission assembly of FIG. 16, taken along line E-E of FIG. 19, with the transmission assembly at the second stage of operation.

As can also be seen from a comparison between FIG. 20B and FIG. 22, engagement between teeth (1132) of first sector gear (1130) and teeth (1222) of sector gear (1220) provides counterclockwise rotation of sector gear (1220) and the rest of shaft assembly (1200) when sector gear (1130) and the rest of shaft assembly (1100) are rotated clockwise by motor (28). As best seen in FIG. 23, fourth rotary cam (1160) of shaft assembly (1100) is rotated out of engagement with first arcuate recess (1412) of first rotary cam (1410), thereby providing clearance for first rotary cam (1410) and the rest of shaft assembly (1400) to rotate as will be described below. As best seen in FIG. 24, teeth (1174) of sector gear (1170) are now positioned to engage teeth (1422) of spur gear (1420), such that subsequent clockwise rotation of shaft assembly (1100) will rotate shaft assembly (1400) counterclockwise. As best seen by comparing FIG. 20F and FIG. 25, the above-described counterclockwise rotation of shaft assembly (1200) causes shaft assembly (1500) to rotate clockwise, due to engagement between teeth (1232) of spur gear (1230) and teeth (1512) of spur gear (1500).

Figure 25:
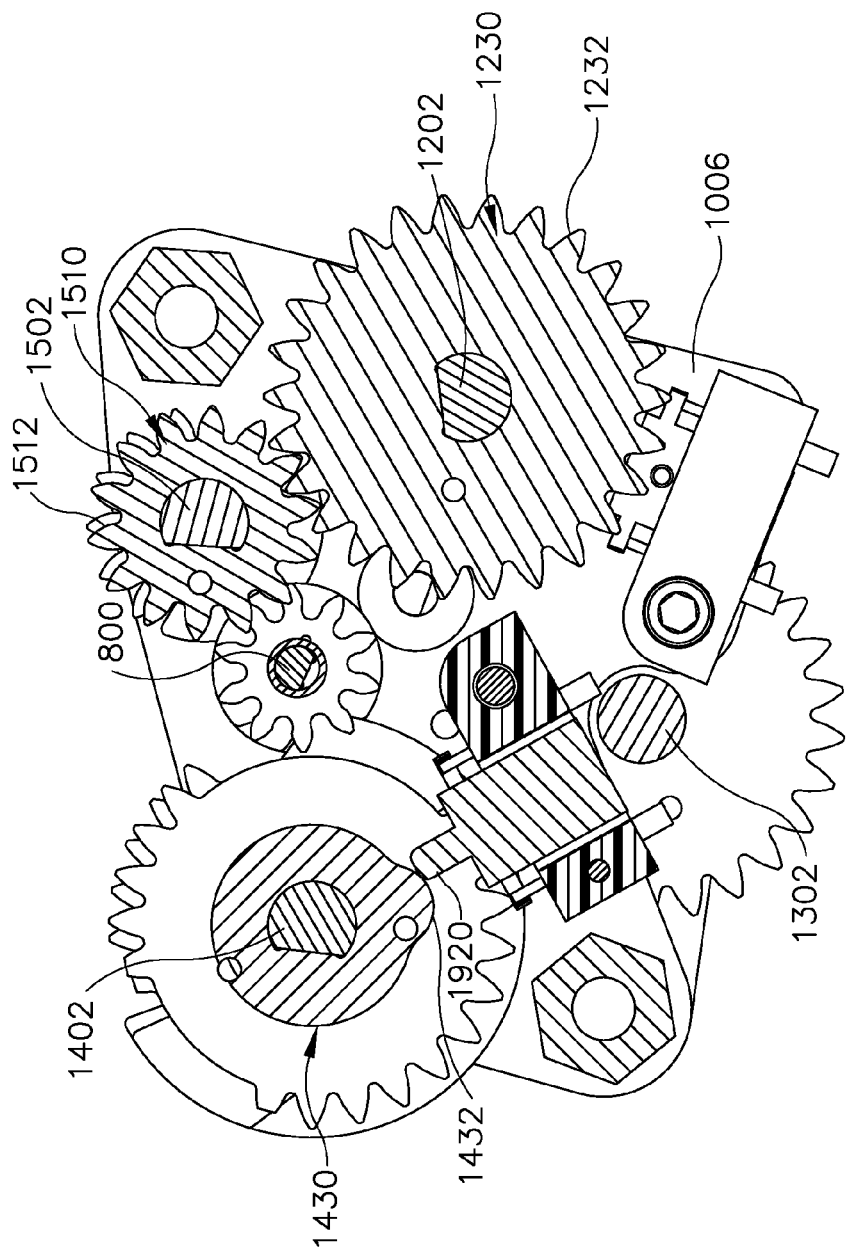
FIG. 25 depicts a cross-sectional view of the transmission assembly of FIG. 16, taken along line F-F of FIG. 19, with the transmission assembly at the second stage of operation.

As also seen in FIG. 25, protrusion (1432) of second rotary cam (1430) is positioned to engage limit switch (1920), to thereby send a signal to a control module indicating that end effector (200) has reached the configuration and position shown in FIG. 8C. This may trigger a variety of responses. For instance, this may automatically stop motor (28) to stop rotation of components of transmission assembly (1000), requiring the surgeon to engage rocker (24) or release and re-engage rocker (24) to continue operation of suturing instrument (10). In addition or in the alternative, triggering of limit switch (1920) may provide a form of audio feedback (e.g., beep or other audible tone, etc.) and/or visual feedback (e.g., illumination or blinking of an LED, etc.) to the surgeon indicating that end effector (200) has reached this operational stage. Other suitable responses that may be triggered by activation of limit switch (1920) will be apparent to those of ordinary skill in the art in view of the teachings herein. It should also be understood that, in some versions, limit switch (1920) is not activated until some other operational stage is reached (e.g., right after the stage depicted in FIGS. 21-31).

Figure 26:
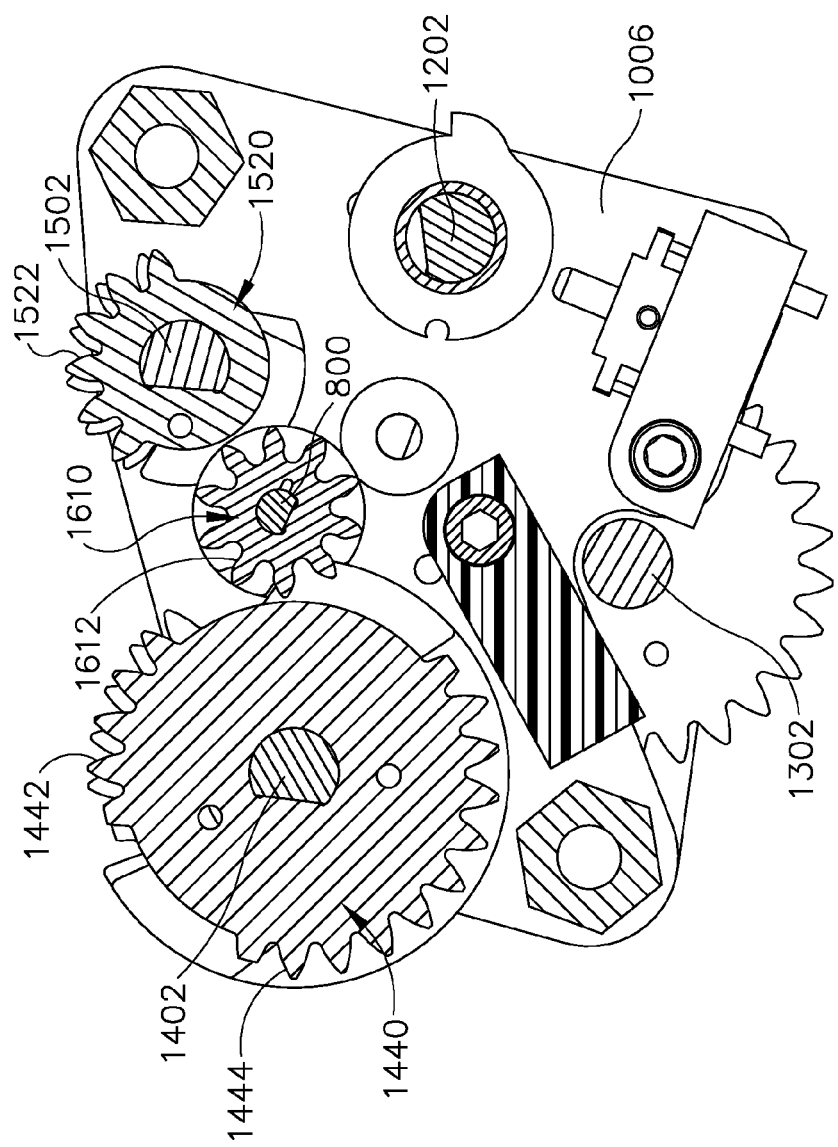
FIG. 26 depicts a cross-sectional view of the transmission assembly of FIG. 16, taken along line G-G of FIG. 19, with the transmission assembly at the second stage of operation.
Figure 27:
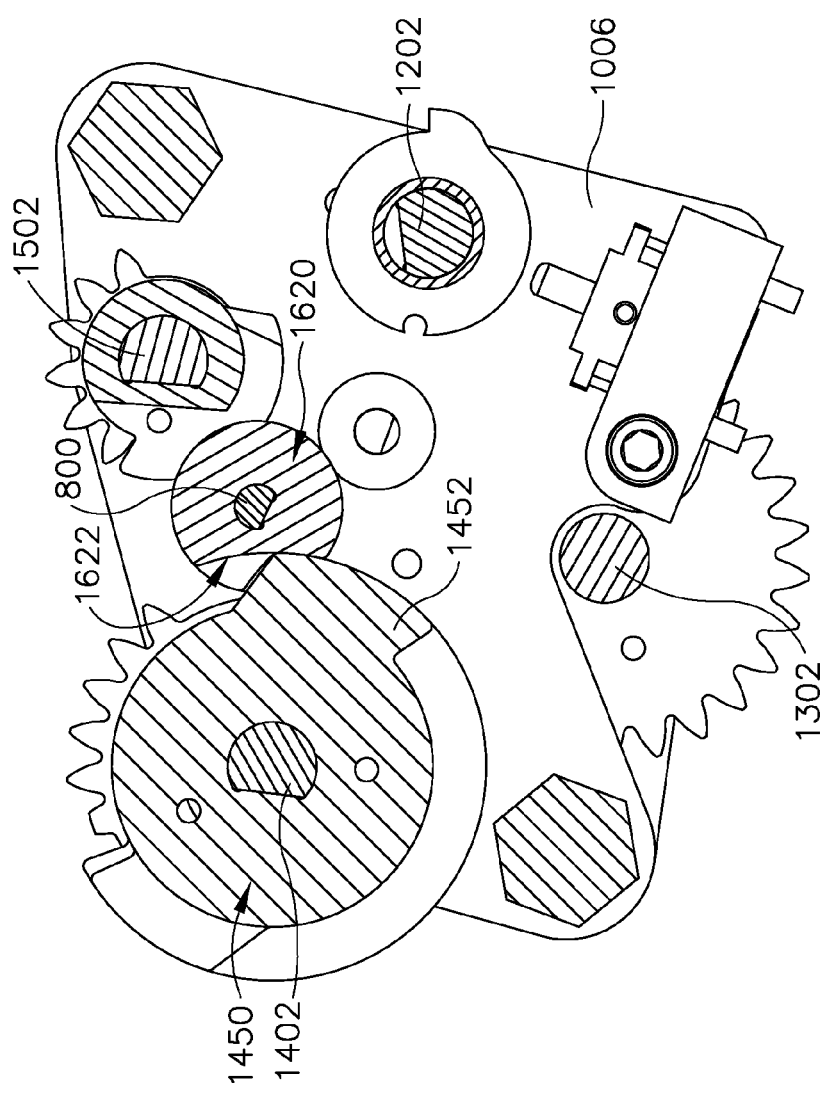
FIG. 27 depicts a cross-sectional view of the transmission assembly of FIG. 16, taken along line H-H of FIG. 19, with the transmission assembly at the second stage of operation.
Figure 28:
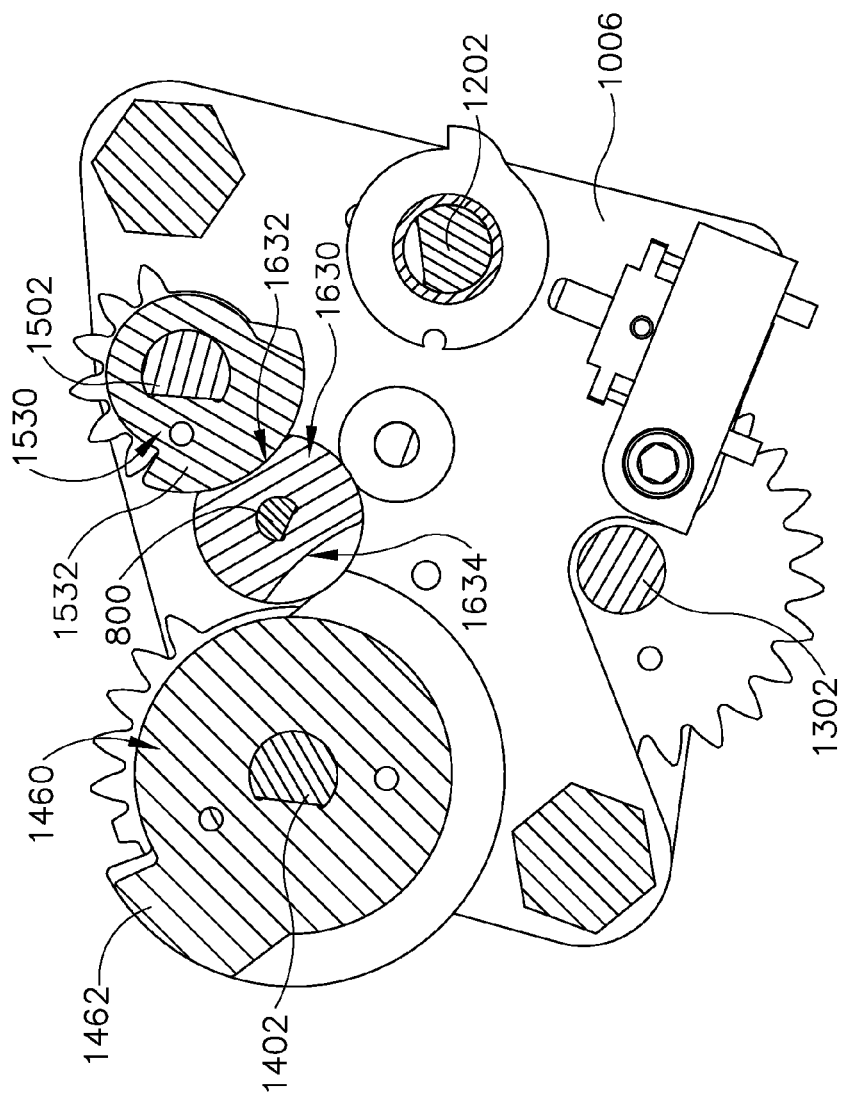
FIG. 28 depicts a cross-sectional view of the transmission assembly of FIG. 16, taken along line I-I of FIG. 19, with the transmission assembly at the second stage of operation.
Figure 29:
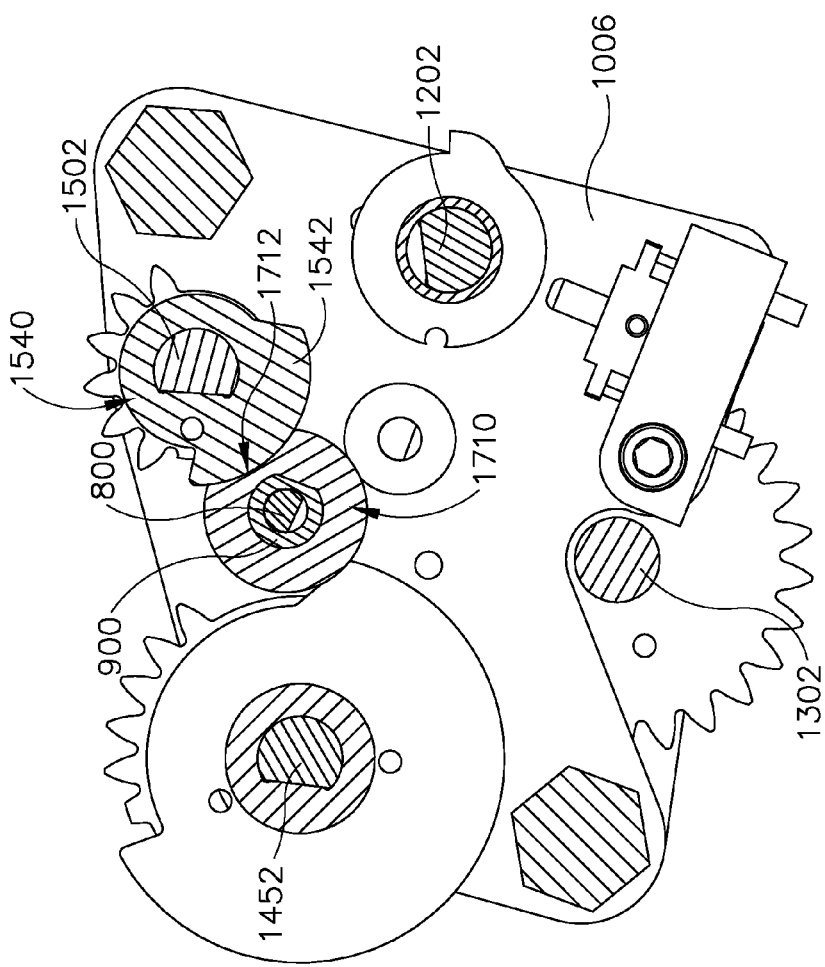
FIG. 29 depicts a cross-sectional view of the transmission assembly of FIG. 16, taken along line J-J of FIG. 19, with the transmission assembly at the second stage of operation.
Figure 30:
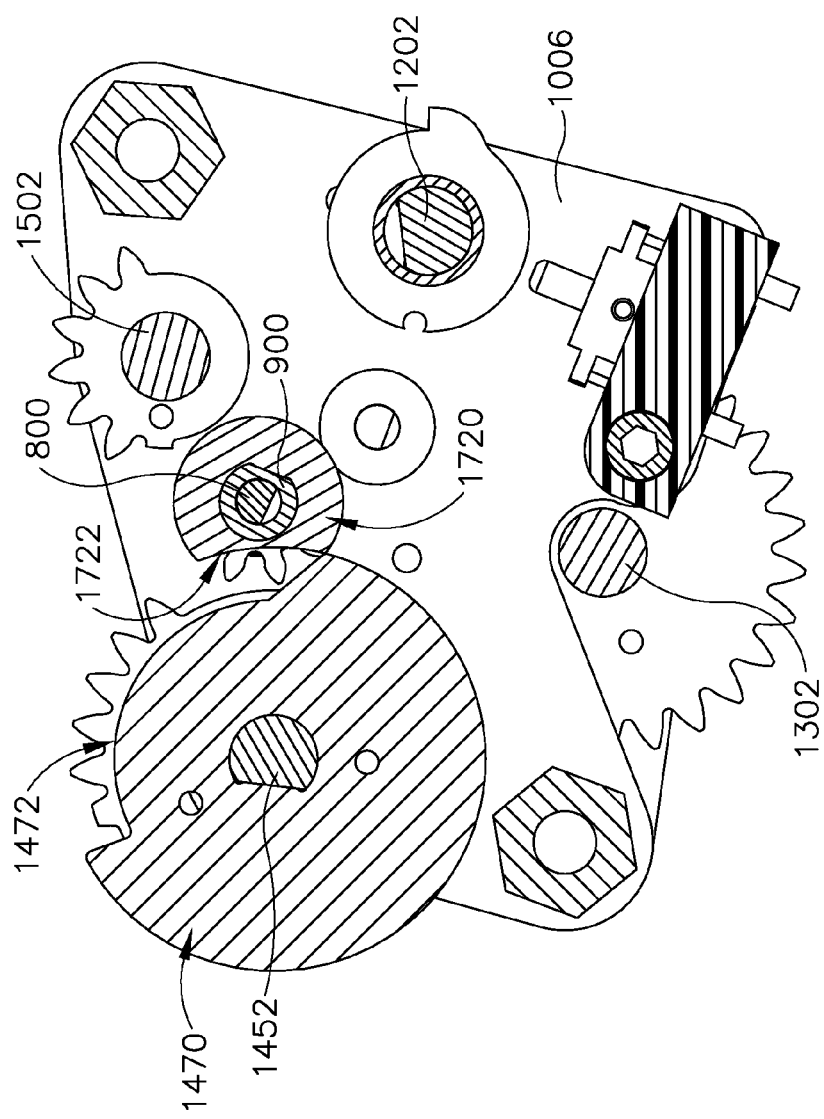
FIG. 30 depicts a cross-sectional view of the transmission assembly of FIG. 16, taken along line K-K of FIG. 19, with the transmission assembly at the second stage of operation.

As best seen by comparing FIG. 20G with FIG. 26, the above-described clockwise rotation of shaft assembly (1500) has caused shaft assembly (1600) (including output shaft (800)) to rotate counterclockwise due to engagement between teeth (1522) of first sector gear (1520) and teeth (1612) of spur gear (1610). However, as shown in FIG. 27, protrusion (1452) of third rotary cam (1450) has moved into engagement with first rotary cam (1620) at arcuate recess (1622), thereby holding first rotary cam (1620) and the rest of shaft assembly (1600) (including output shaft (800)) in the position shown in FIGS. 21-31. Similarly, as shown in FIG. 28, protrusion (1532) of first rotary cam (1530) has moved into engagement with first arcuate recess (1632) of second rotary cam (1630), thereby further holding second rotary cam (1620) and the rest of shaft assembly (1600) (including output shaft (800)) in the position shown in FIGS. 21-31. As shown in FIG. 29, protrusion (1542) of second rotary cam (1530) as moved into engagement with arcuate recess (1712) of first rotary cam (1710), thereby holding rotary cam (1710) and the rest of shaft assembly (1700) (including output shaft (900)) in the position shown in FIGS. 21-31. However, as will be described below, the rotational position of shaft assembly (1700) (including output shaft (900)) is different in the stage depicted in FIGS. 21-32 relative to the position of shaft assembly (1700) (including output shaft (900)) in the stage depicted in FIGS. 20A-20M. As shown in FIG. 30, fourth rotary cam (1470) has moved to a position where it will engage arcuate recess (1722) of second rotary cam (1720) upon subsequent rotation of shaft assembly (1400), which will hold rotary cam (1720) and the rest of shaft assembly (1700) (including output shaft (900)) stationary upon further rotation of shaft assembly (1400).

Figure 31:
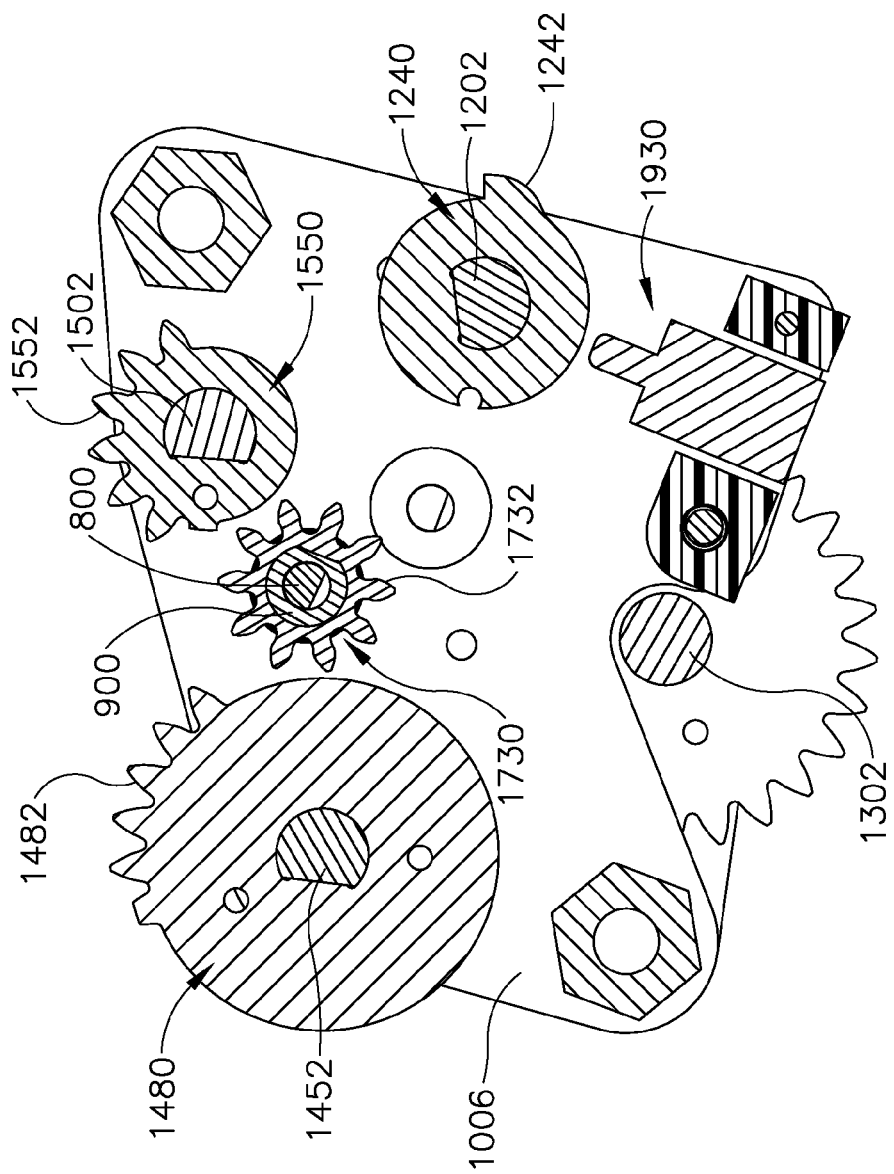
FIG. 31 depicts a cross-sectional view of the transmission assembly of FIG. 16, taken along line L-L of FIG. 19, with the transmission assembly at the second stage of operation.
Figure 32:
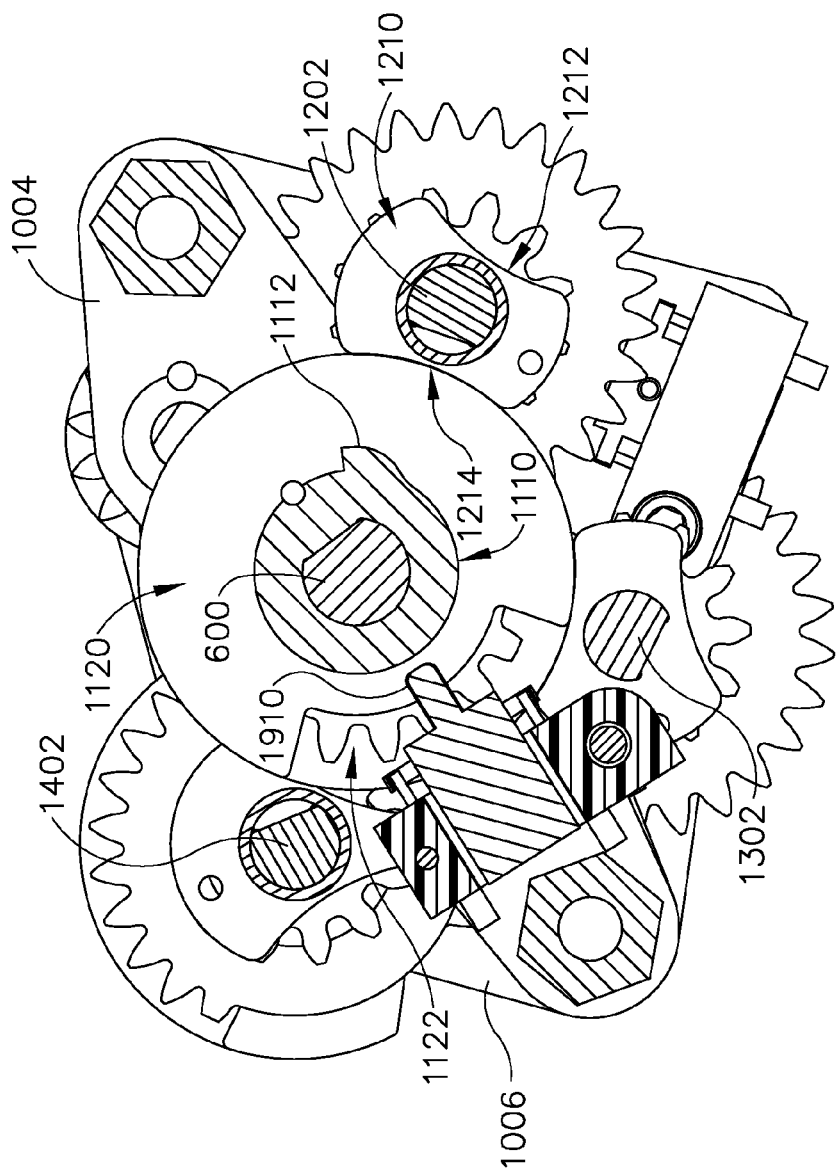
FIG. 32 depicts a cross-sectional view of the transmission assembly of FIG. 16, taken along line A-A of FIG. 19, with the transmission assembly at a third stage of operation.

As best seen by comparing FIG. 20L with FIG. 31, the above-described clockwise rotation of shaft assembly (1500) has caused shaft assembly (1700) (including output shaft (900)) to rotate counterclockwise due to engagement between teeth (1552) of second sector gear (1550) and teeth (1732) of spur gear (1730). As noted above, engagement between protrusion (1542) of second rotary cam (1530) and arcuate recess (1712) of first rotary cam (1710) holds the rotational position of shaft assembly (1700) once it has reached this position. It should be understood from the foregoing that both output shafts (800, 900) have rotated counterclockwise during the transition of end effector (200) from the configuration shown in FIG. 8B to the configuration shown in FIG. 8C. This counterclockwise rotation of output shafts (800, 900) is synchronized at the same rate of rotation. Thus, the synchronized rotation of output shafts (800, 900) provides rotation of the entire grasping arm (250) about axis (140); while still keeping jaws (260, 270) consistently open during this movement.

3. Grasping Needle with Needle Receiving Arm

Figure 33:
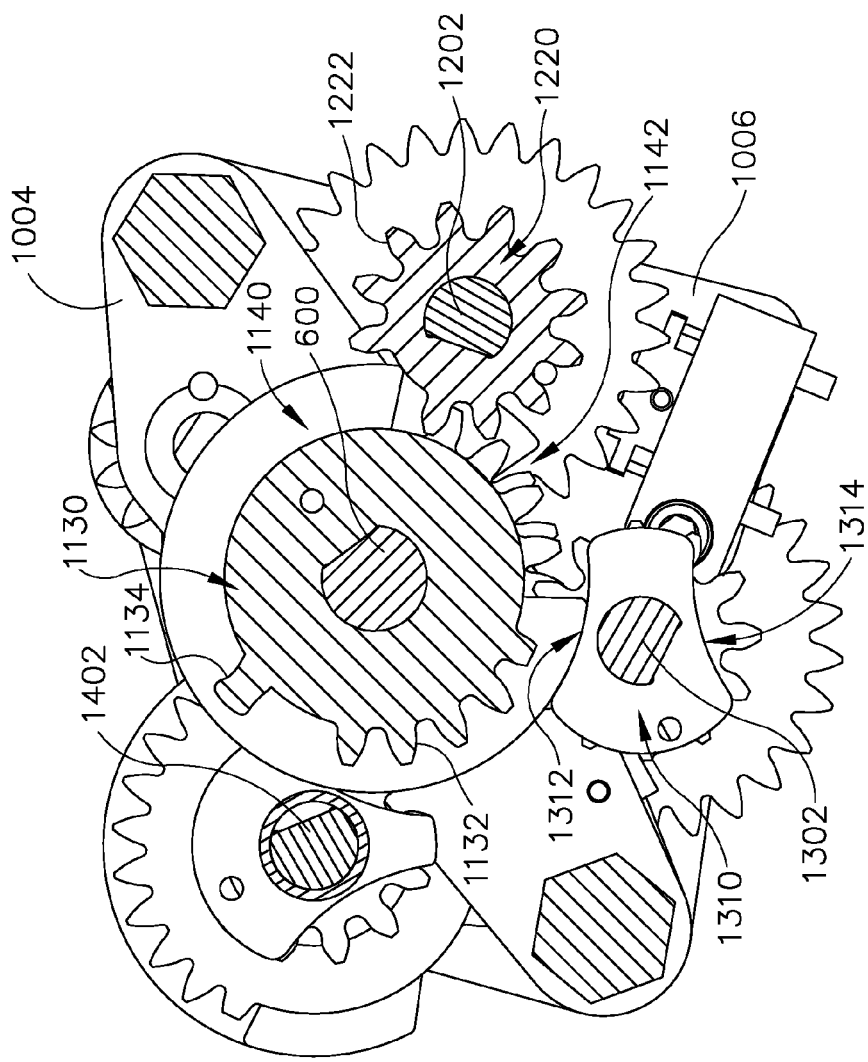
FIG. 33 depicts a cross-sectional view of the transmission assembly of FIG. 16, taken along line B-B of FIG. 19, with the transmission assembly at the third stage of operation.
Figure 34:
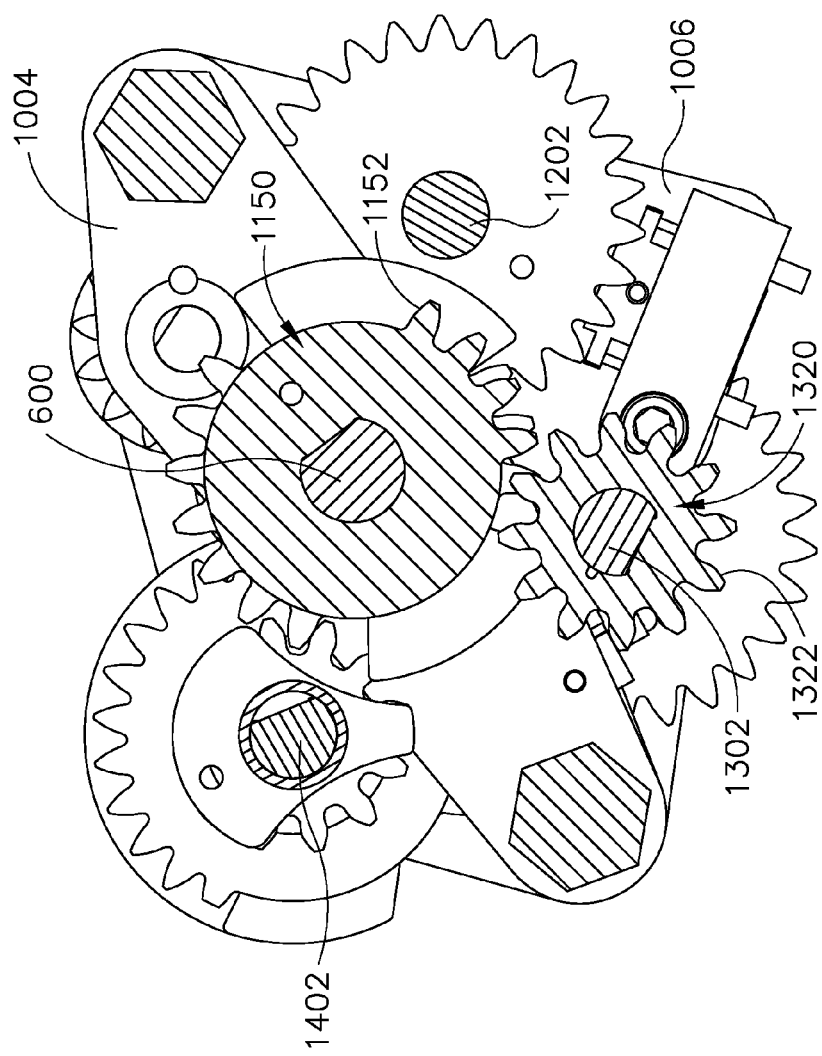
FIG. 34 depicts a cross-sectional view of the transmission assembly of FIG. 16, taken along line C-C of FIG. 19, with the transmission assembly at the third stage of operation.

With arms (210, 250) still in the position shown in FIG. 8C, the components of transmission assembly (1000) are actuated from the configuration shown in FIGS. 21-31 to the configuration shown in FIGS. 32-42 to grasp needle (50) with jaws (260, 270) of arm (250). In particular, motor (28) is activated to rotate input shaft (600) and the rest of shaft assembly (1100) clockwise. As best seen by comparing FIG. 21 with FIG. 32, this has moved second rotary cam (1120) into engagement with second arcuate recess (1214) of first rotary cam (1210), thereby holding first rotary cam (1210) and the rest of shaft assembly (1200) stationary in the position shown in FIGS. 32-42. However, as will be described below, the rotational position of shaft assembly (1200) is different in the stage depicted in FIGS. 32-42 relative to the position of shaft assembly (1200) in the stage depicted in FIGS. 21-31. As shown in FIG. 33, third rotary cam (1140) remains engaged with first arcuate recess (1312) of first rotary cam (1312), thereby continuing to hold shaft assembly (1300) stationary at this stage. It should be understood that, due to the coupling between shaft assembly (1300) and output shaft (700) as described above, the relative positioning of jaws (220, 230) remains positively fixed at this stage, with jaws (220, 230) continuing to firmly grasp needle (50).

As best seen by comparing FIG. 22 with FIG. 33, the clockwise rotation of shaft assembly (1100) has caused shaft assembly (1200) to rotate counterclockwise due to engagement between teeth (1132) of first sector gear (1130) and teeth (1222) of sector gear (1220). As noted above, engagement between second rotary cam (1120) and second arcuate recess (1214) of first rotary cam (1210) holds the rotational position of shaft assembly (1200) once it has reached this position. As best seen by comparing FIG. 20C with FIG. 34, teeth (1152) of second sector gear (1150) are now positioned to engage teeth (1322) of spur gear (1320), such that subsequent clockwise rotation of shaft assembly (1100) will rotate shaft assembly (1300) counterclockwise. As best seem in FIG. 35, fourth rotary cam (1160) of shaft assembly (1100) remains disengaged from first rotary cam (1410), with recessed region (1164) providing full clearance for first rotary cam (1410) and the rest of shaft assembly (1400) to rotate as described below. However, fourth rotary cam (1160) is positioned to engage second arcuate recess (1414) of first rotary cam (1410) upon subsequent clockwise rotation of shaft assembly (1100), to thereby hold the position of first rotary cam (1410) and the rest of shaft assembly (1400) upon subsequent clockwise rotation of shaft assembly (1100).

Figure 36:
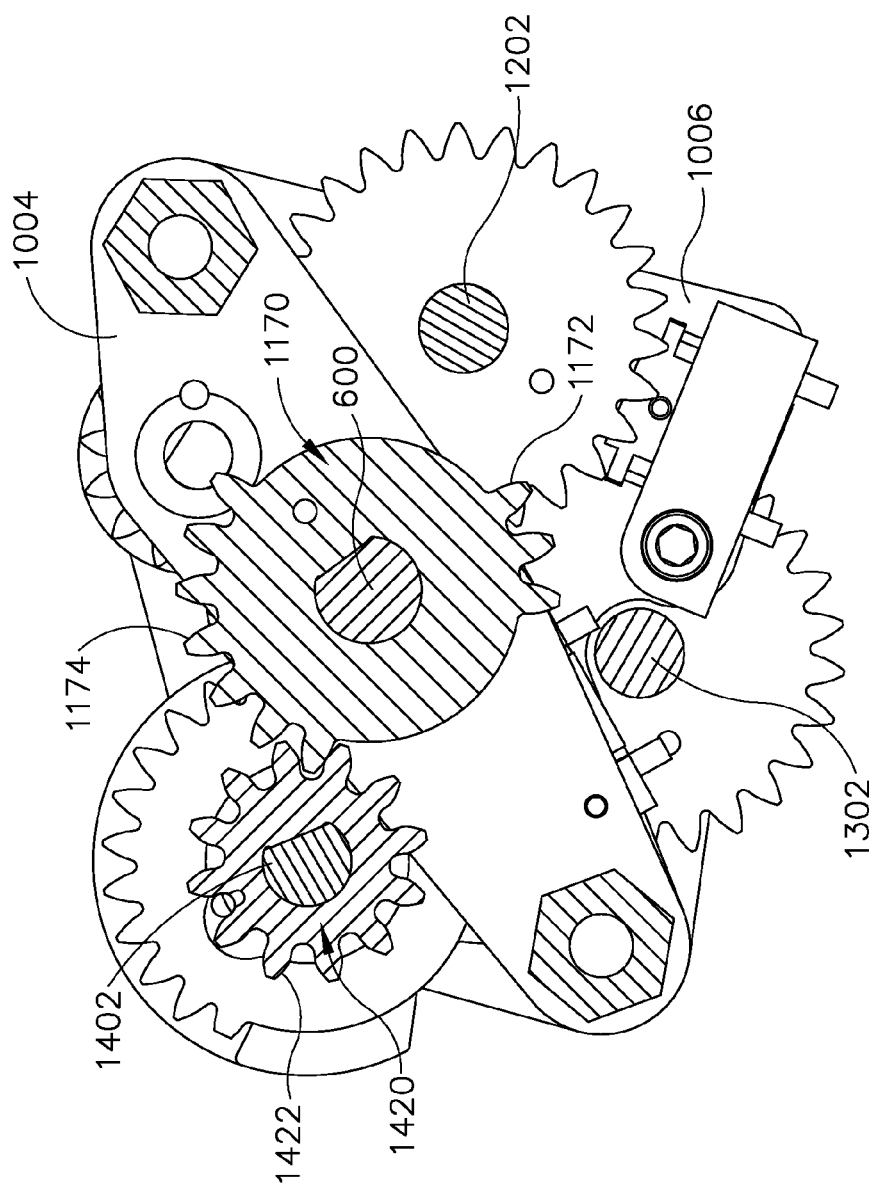
FIG. 36 depicts a cross-sectional view of the transmission assembly of FIG. 16, taken along line E-E of FIG. 19, with the transmission assembly at the third stage of operation.
Figure 37:
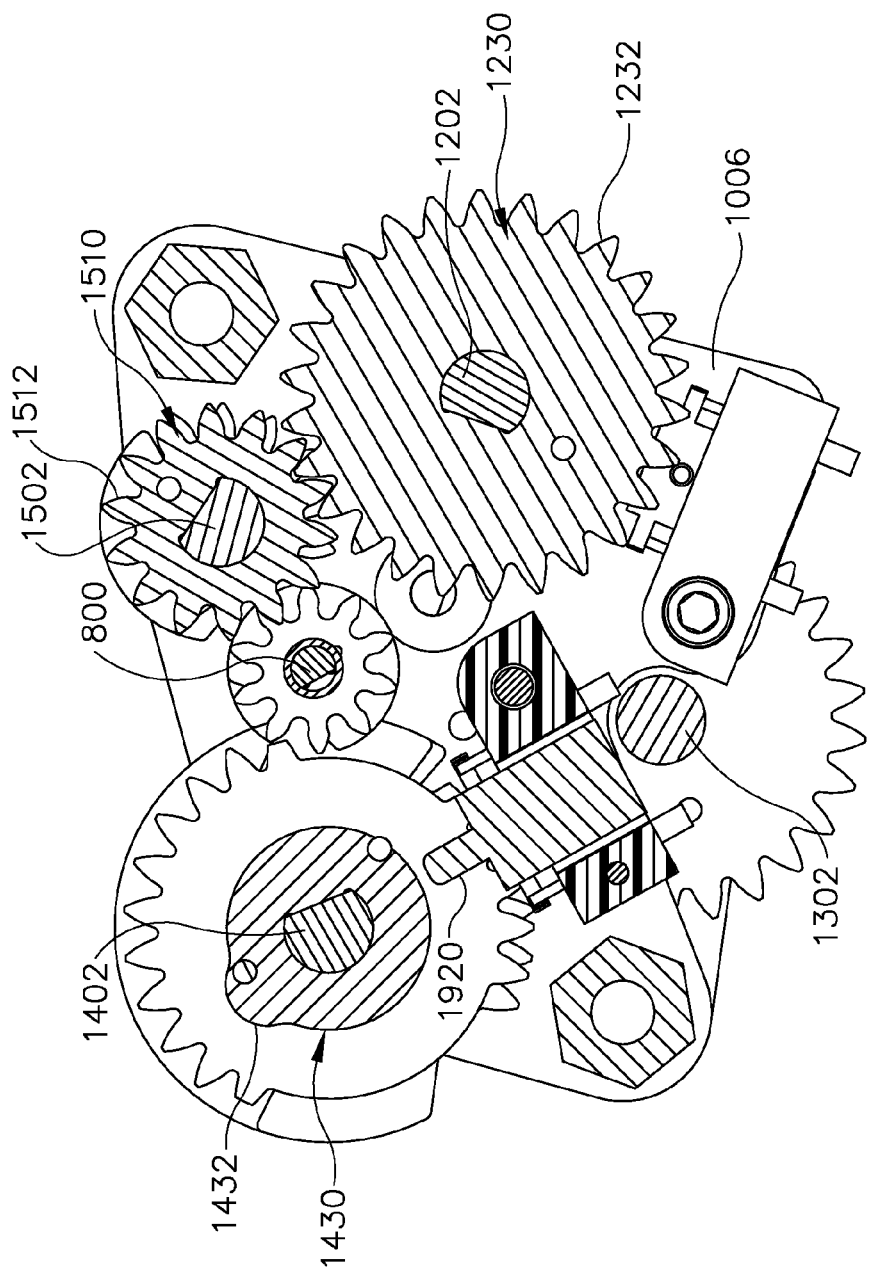
FIG. 37 depicts a cross-sectional view of the transmission assembly of FIG. 16, taken along line F-F of FIG. 19, with the transmission assembly at the third stage of operation.

As best seen by comparing FIG. 24 with FIG. 36, the clockwise rotation of shaft assembly (1100) has caused shaft assembly (1400) to rotate counterclockwise due to engagement between teeth (1174) of sector gear (1170) and teeth (1422) of spur gear (1420). As best seen by comparing FIG. 25 with FIG. 37, the counterclockwise rotation of shaft assembly (1200) has caused shaft assembly (1500) to rotate clockwise due to engagement between teeth (1232) of spur gear (1230) and teeth (1512) of spur gear (1510). As noted above, engagement between second rotary cam (1120) and second arcuate recess (1214) of first rotary cam (1210) holds the rotational position of shaft assembly (1200) once it has reached this position. It should therefore be understood that engagement between teeth (1232) of spur gear (1230) and teeth (1512) of spur gear (1510) holds the rotational position of shaft assembly (1500) once it has reached this position.

Figure 38:
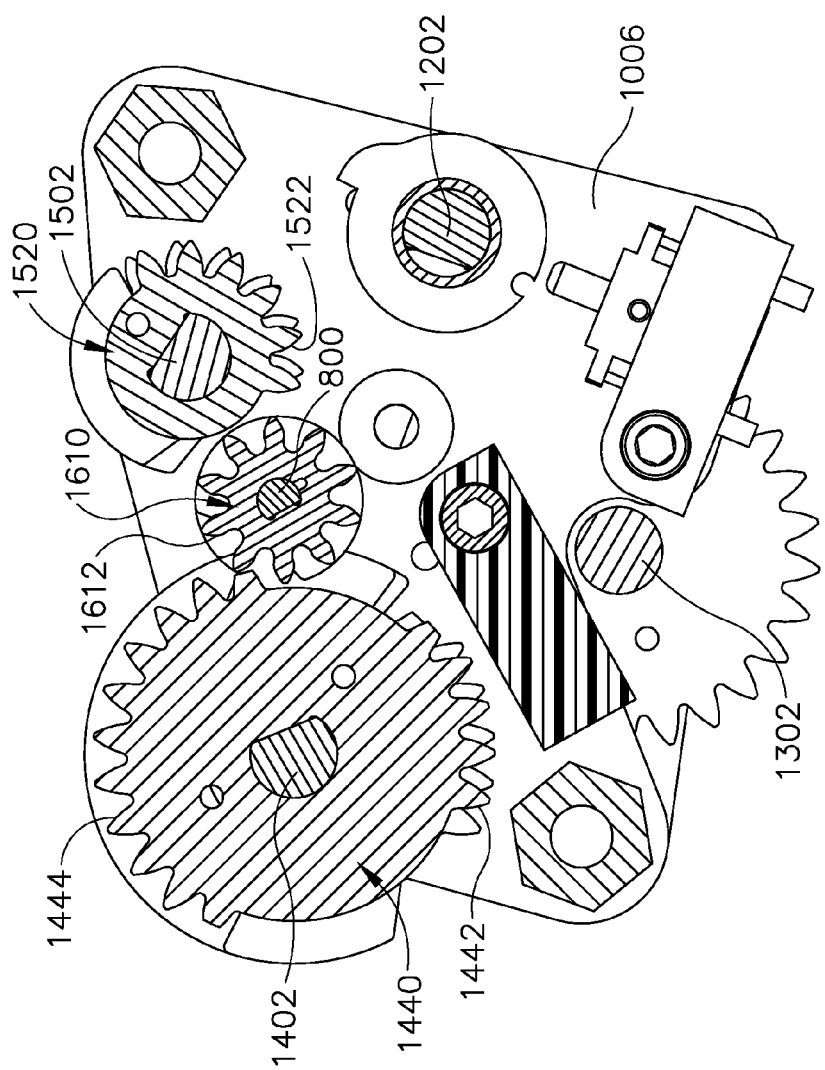
FIG. 38 depicts a cross-sectional view of the transmission assembly of FIG. 16, taken along line G-G of FIG. 19, with the transmission assembly at the third stage of operation.
Figure 39:
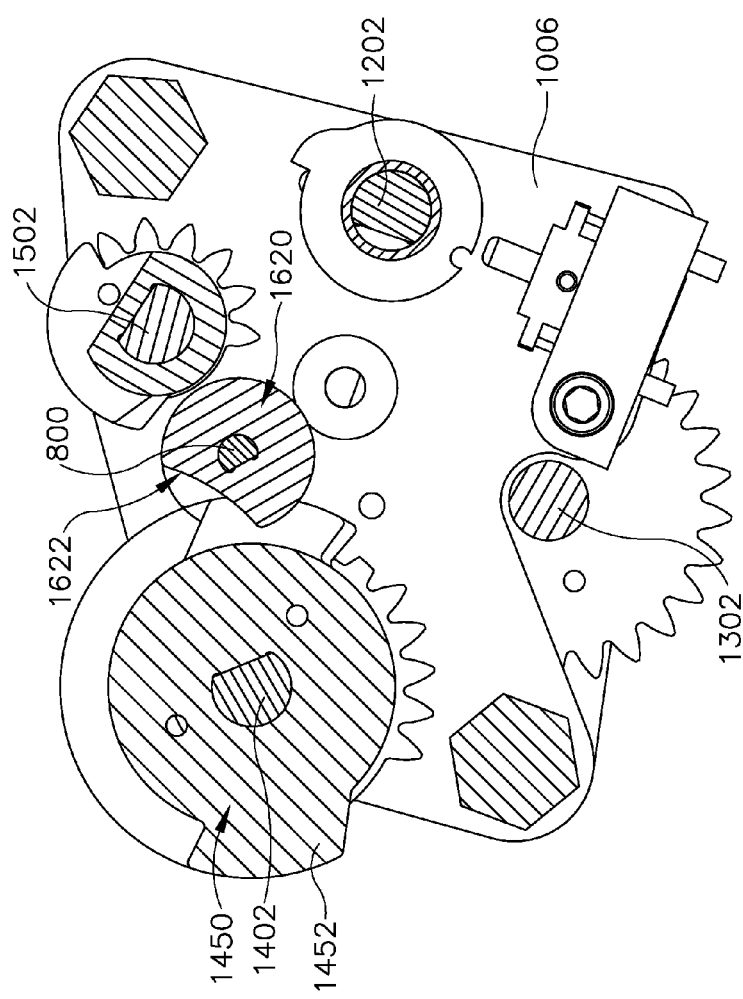
FIG. 39 depicts a cross-sectional view of the transmission assembly of FIG. 16, taken along line H-H of FIG. 19, with the transmission assembly at the third stage of operation.
Figure 40:
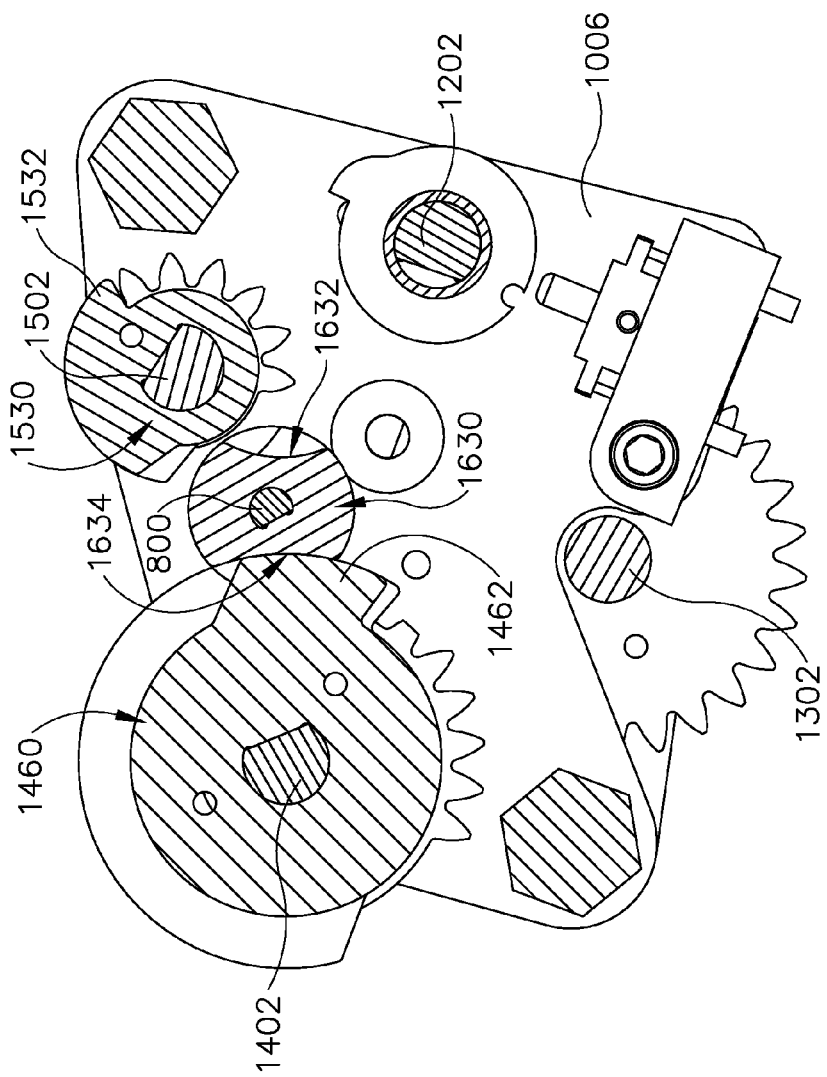
FIG. 40 depicts a cross-sectional view of the transmission assembly of FIG. 16, taken along line I-I of FIG. 19, with the transmission assembly at the third stage of operation.

As best seen by comparing FIG. 26 with FIG. 38, the counterclockwise rotation of shaft assembly (1400) has caused shaft assembly (1600) (including output shaft (800)) to rotate clockwise due to engagement between teeth (1444) of sector gear (1440) and teeth (1612) of spur gear (1610). As seen by comparing FIG. 27 with FIG. 39, protrusion (1452) of third rotary cam (1450) has moved out of engagement with arcuate recess (1622) of first rotary cam (1620), to thereby permit the rotation of shaft assembly (1600) by shaft assembly (1400). As shown by comparing FIG. 28 with FIG. 40, protrusion (1532) of first rotary cam (1530) has also moved out of engagement with first arcuate recess (1632) of second rotary cam (1630) to further permit the rotation of shaft assembly (1600) by shaft assembly (1400). However, protrusion (1462) of fourth rotary cam (1460) has moved into engagement with second arcuate recess (1634) of second rotary cam (1630), thereby holding the rotational position of shaft assembly (1600) (including output shaft (800)) once it has reached this position.

Figure 41:
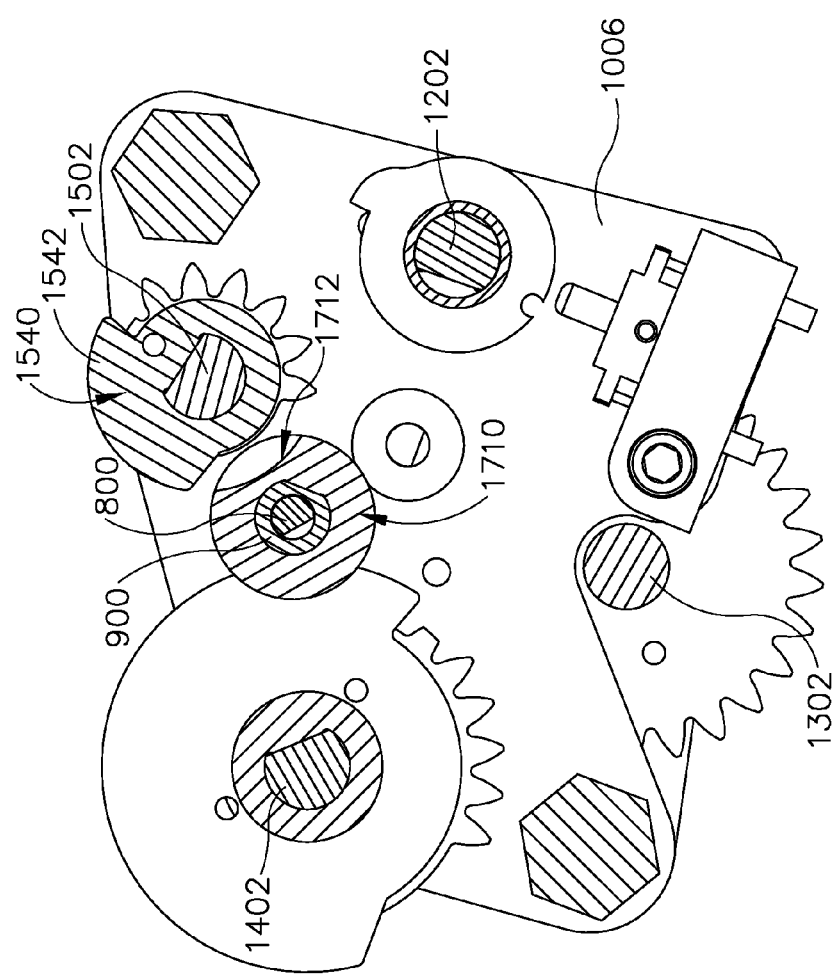
FIG. 41 depicts a cross-sectional view of the transmission assembly of FIG. 16, taken along line J-J of FIG. 19, with the transmission assembly at the third stage of operation.
Figure 42:
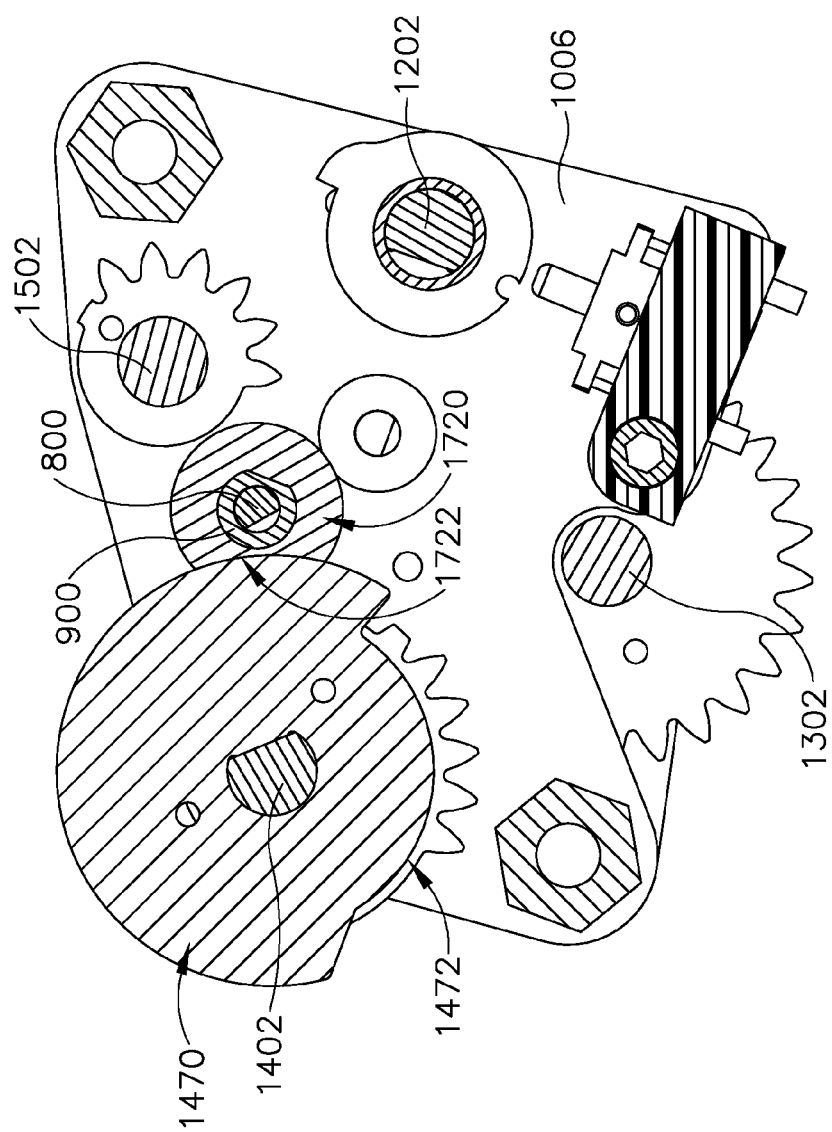
FIG. 42 depicts a cross-sectional view of the transmission assembly of FIG. 16, taken along line K-K of FIG. 19, with the transmission assembly at the third stage of operation.
Figure 43:
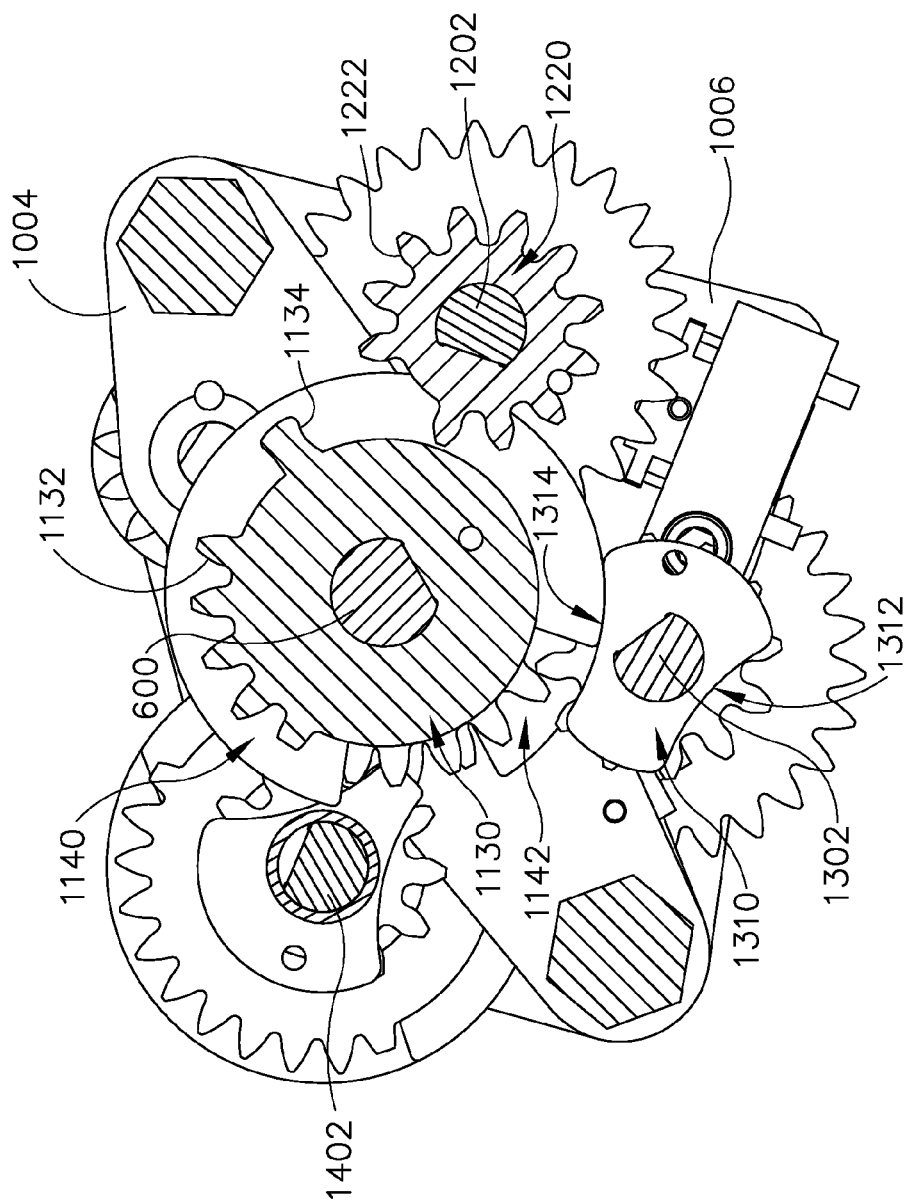
FIG. 43 depicts a cross-sectional view of the transmission assembly of FIG. 16, taken along line B-B of FIG. 19, with the transmission assembly at a fourth stage of operation.
Figure 44:
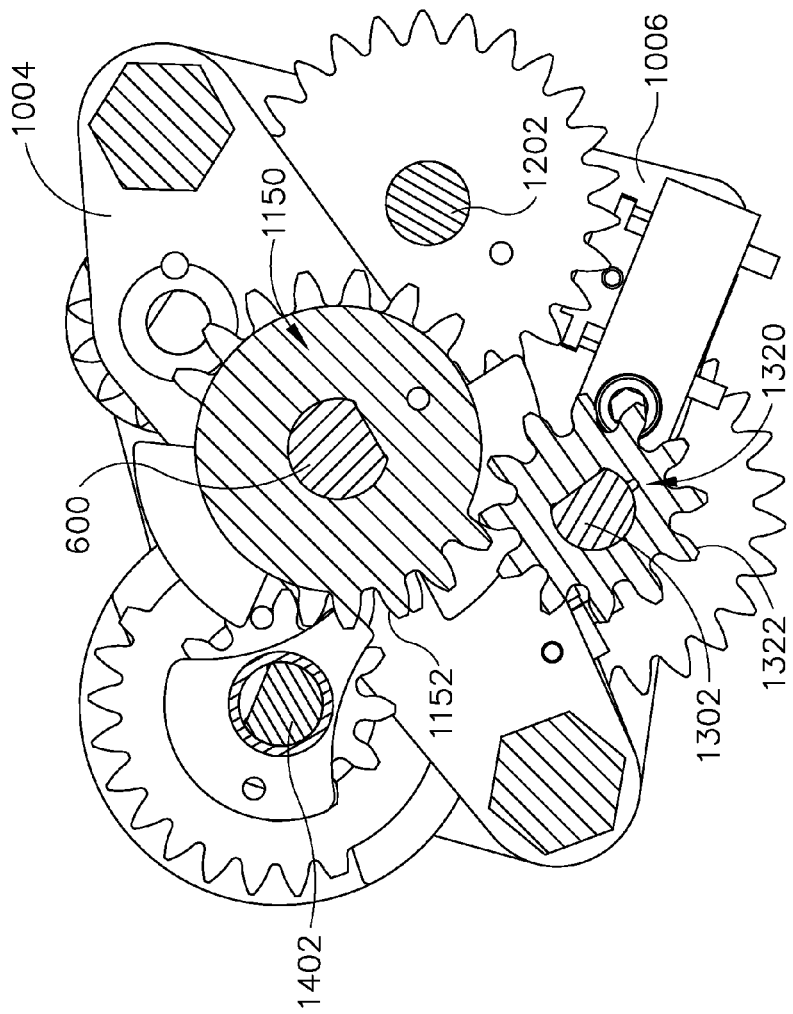
FIG. 44 depicts a cross-sectional view of the transmission assembly of FIG. 16, taken along line C-C of FIG. 19, with the transmission assembly at the fourth stage of operation.

As best seen by comparing FIG. 29 with FIG. 41, protrusion (1542) of second rotary cam (1530) as moved out of engagement with arcuate recess (1712) of first rotary cam (1710), such that second rotary cam (1530) no longer holds the position of first rotary cam (1710) or the rest of shaft assembly (1700). However, as shown in FIG. 42, fourth rotary cam (1470) has moved into engagement with arcuate recess (1722) of second rotary cam (1720), such that fourth rotary cam (1470) holds the position of second rotary cam (1720) and the rest of shaft assembly (1700) (including output shaft (900)) during the entire transition from the configuration shown in FIGS. 21-31 to the configuration shown in FIGS. 32-42.

It should be understood from the foregoing that output shaft (800) rotates clockwise while output shaft (900) remains stationary during the transition of transmission assembly (1000) from the configuration shown in FIGS. 21-31 to the configuration shown in FIGS. 32-42. Since output shaft (800) is coupled with drive shaft (284) and output shaft (900) is coupled with hollow shaft (280), it will be understood that this rotation of output shaft (800) (and drive shaft (284)) relative to shaft (900) (and hollow shaft (280)) will cause opposing translation of jaws (260, 270) to grasp needle (50). It will also be understood that the positive fixation of the rotational positions of output shafts (800, 900) once transmission assembly (1000) reaches the configuration shown in FIGS. 32-42 will firmly maintain the grasp of needle (50) by jaws (260, 270) until transmission assembly (1000) is actuated to release needle (50) from jaws (260, 270).

4. Releasing Needle from Needle Driving Arm

Still referring to FIG. 8C, once needle (50) is grasped with jaws (260, 270) of arm (250), the components of transmission assembly (1000) are actuated from the configuration shown in FIGS. 32-42 to the configuration shown in FIGS. 43-50 to release needle (50) from jaws (220, 230) of arm (210). In particular, motor (28) is activated to continue rotating input shaft (600) and the rest of shaft assembly (1100) clockwise. Second rotary cam (1120) of shaft assembly (1100) continues to engage first arcuate recess (1214) of first rotary cam (1210), thereby continuing to hold shaft assembly (1200) stationary throughout this transition. As best seen by comparing FIG. 33 with FIG. 43, this has moved third rotary cam (1140) in such a way that recessed region (1142) passes over first rotary cam (1310), providing clearance for rotary cam (1310) and the rest of shaft assembly (1300) to rotate. However, third rotary cam (1140) holds rotary cam (1310) and the rest of shaft assembly (1300) upon reaching this stage. As best seen by comparing FIG. 34 with FIG. 44, the clockwise rotation of shaft assembly (1100) has caused shaft assembly (1300) to rotate counterclockwise due to engagement between teeth (1152) of second sector gear (1150) and teeth (1322) of spur gear (1320).

Figure 35:
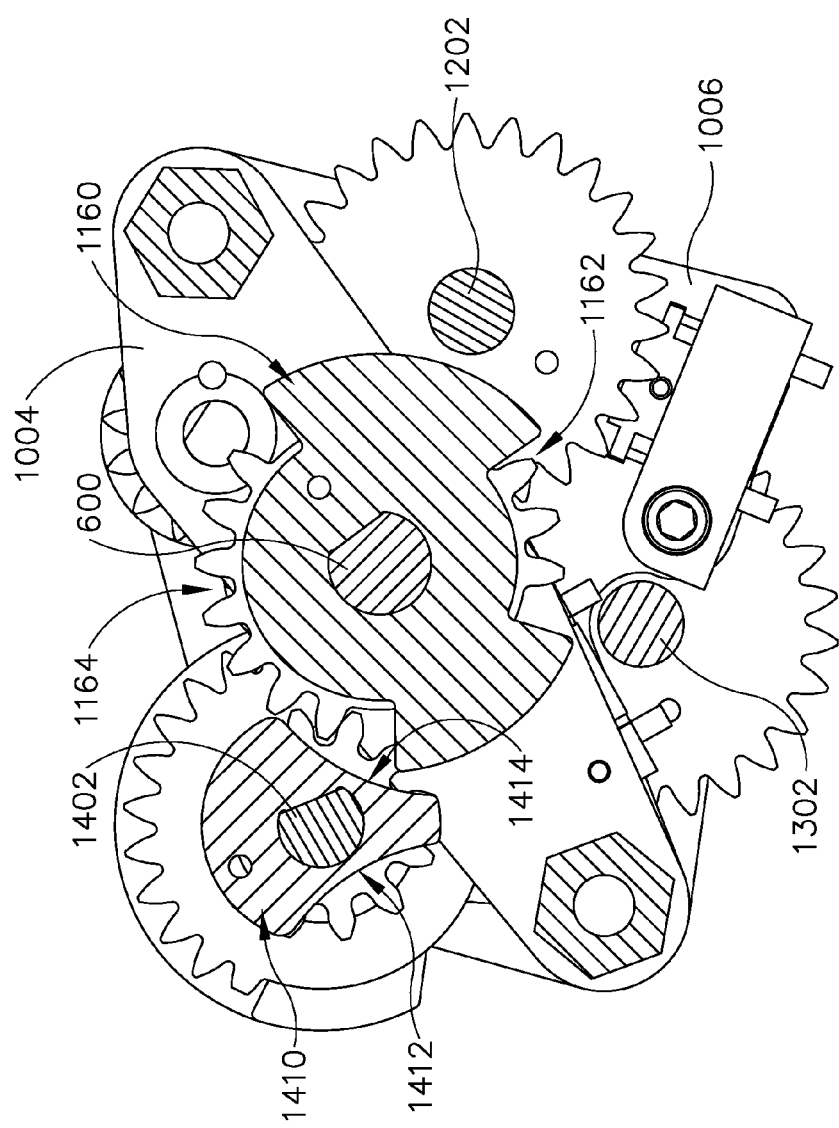
FIG. 35 depicts a cross-sectional view of the transmission assembly of FIG. 16, taken along line D-D of FIG. 19, with the transmission assembly at the third stage of operation.
Figure 45:
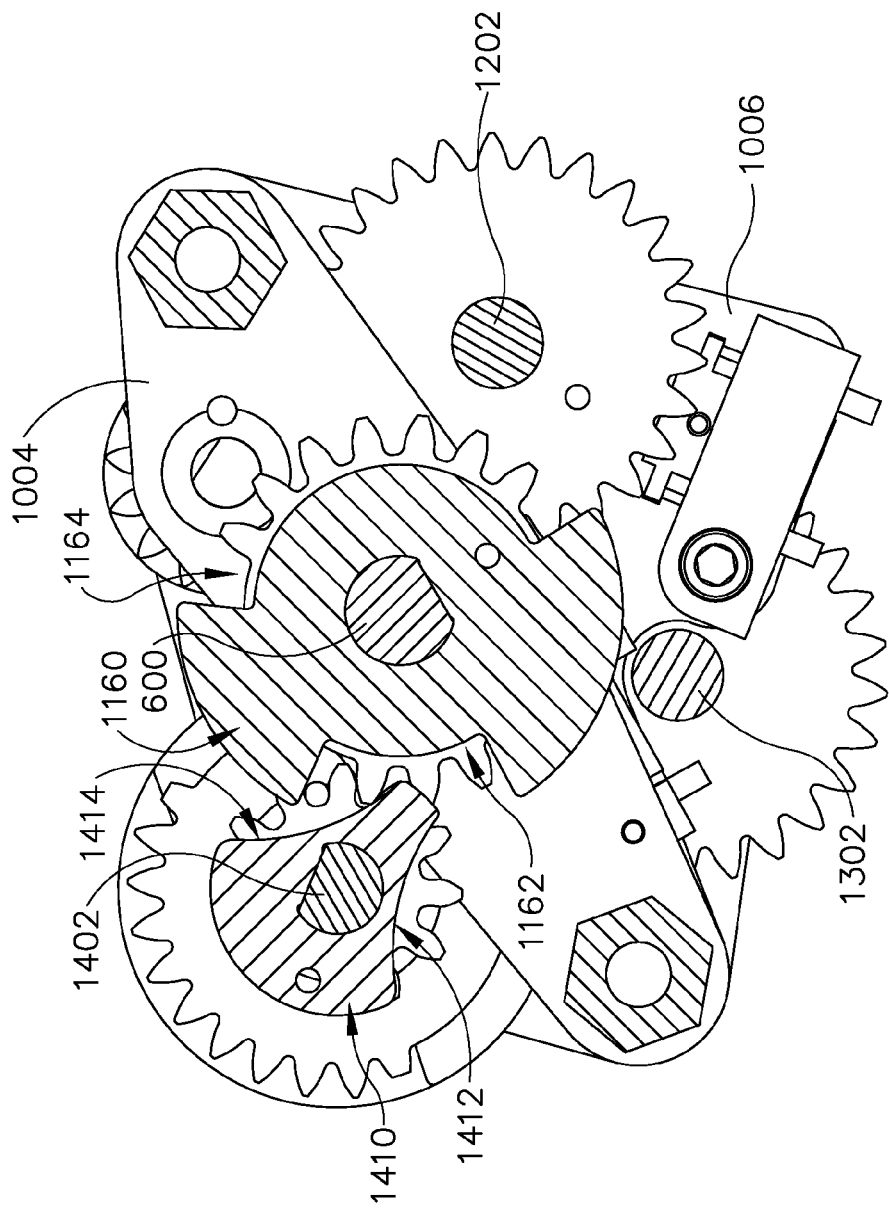
FIG. 45 depicts a cross-sectional view of the transmission assembly of FIG. 16, taken along line D-D of FIG. 19, with the transmission assembly at the fourth stage of operation.
Figure 46:
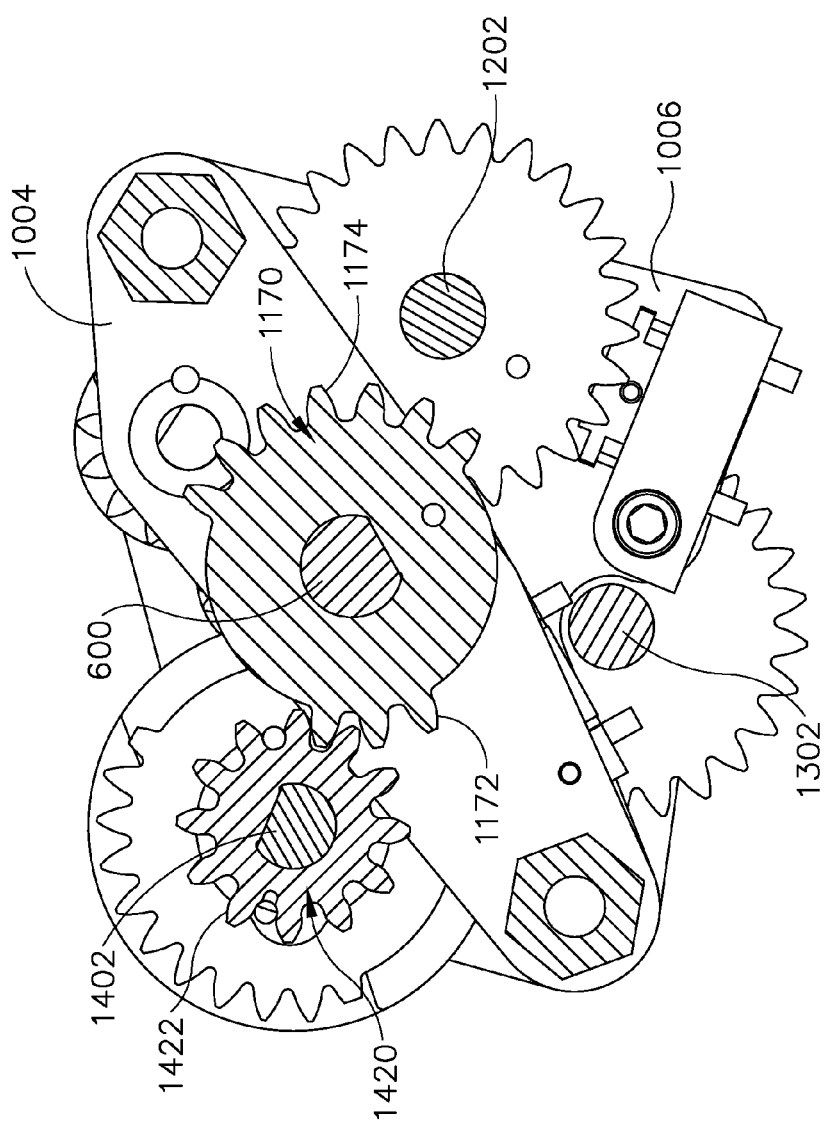
FIG. 46 depicts a cross-sectional view of the transmission assembly of FIG. 16, taken along line E-E of FIG. 19, with the transmission assembly at the fourth stage of operation.

As best seen by comparing FIG. 35 with FIG. 45, fourth rotary cam (1160) has rotated in such a way that it briefly engaged second arcuate recess (1414) of first rotary cam (1410), to briefly hold the rotational position of first rotary cam (1410) and the rest of shaft assembly (1400); yet such that first recessed region (1162) is now positioned to provide clearance for some subsequent degree of rotation of first rotary cam (1410) and the rest of shaft assembly (1400). As shown in FIG. 46, teeth (1172) of sector gear (1170) have been positioned to engage teeth (1422) of spur gear (1420), such that subsequent clockwise rotation of shaft assembly (1100) will rotate shaft assembly (1400) counterclockwise.

Figure 47:
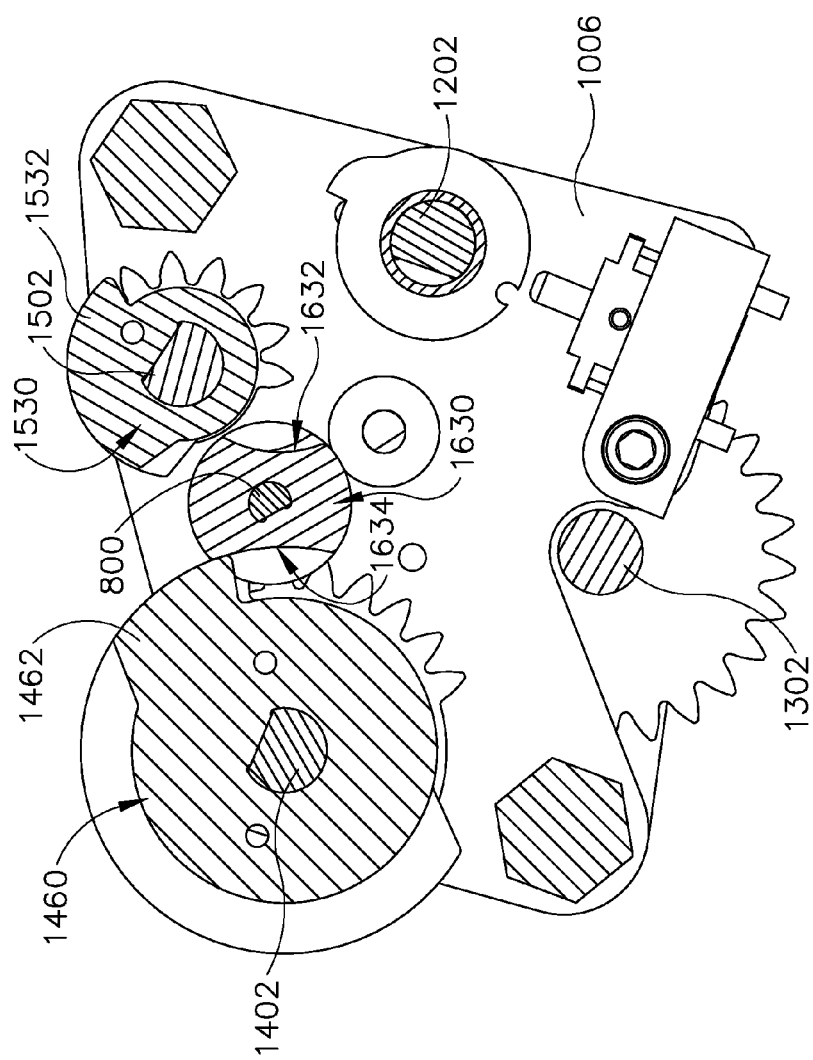
FIG. 47 depicts a cross-sectional view of the transmission assembly of FIG. 16, taken along line I-I of FIG. 19, with the transmission assembly at the fourth stage of operation.
Figure 48:
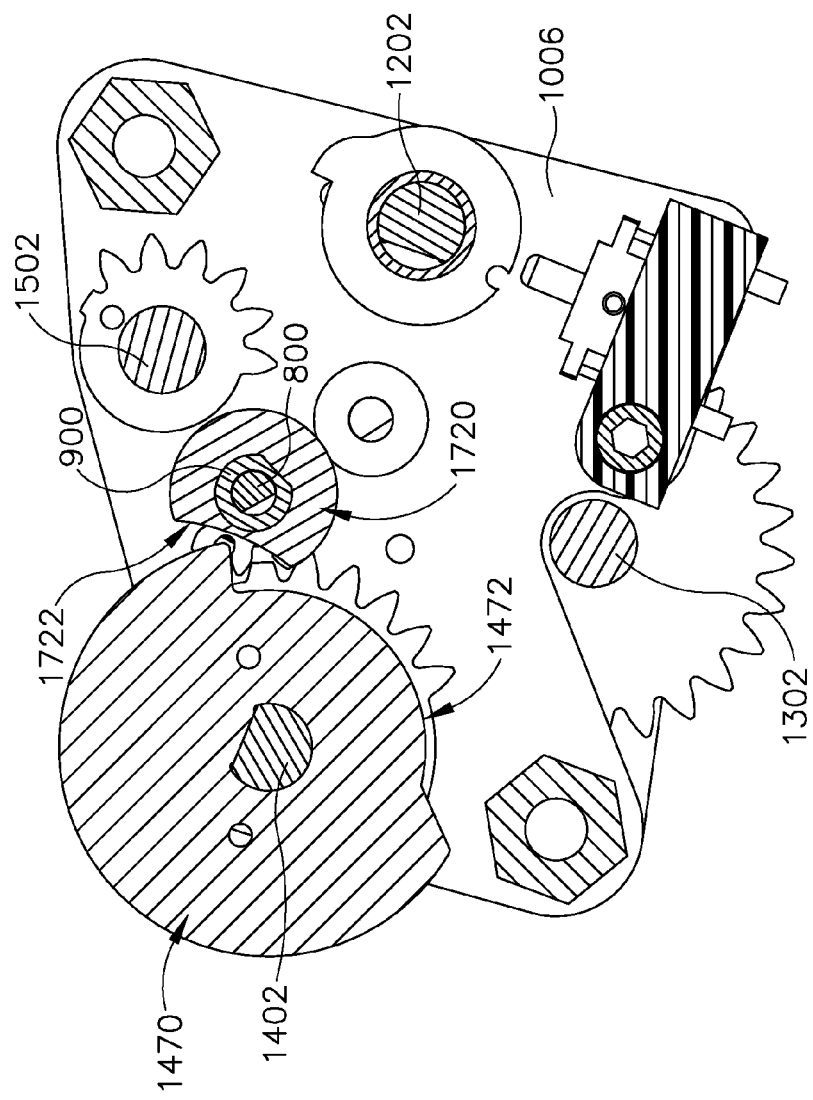
FIG. 48 depicts a cross-sectional view of the transmission assembly of FIG. 16, taken along line K-K of FIG. 19, with the transmission assembly at the fourth stage of operation.
Figure 49:
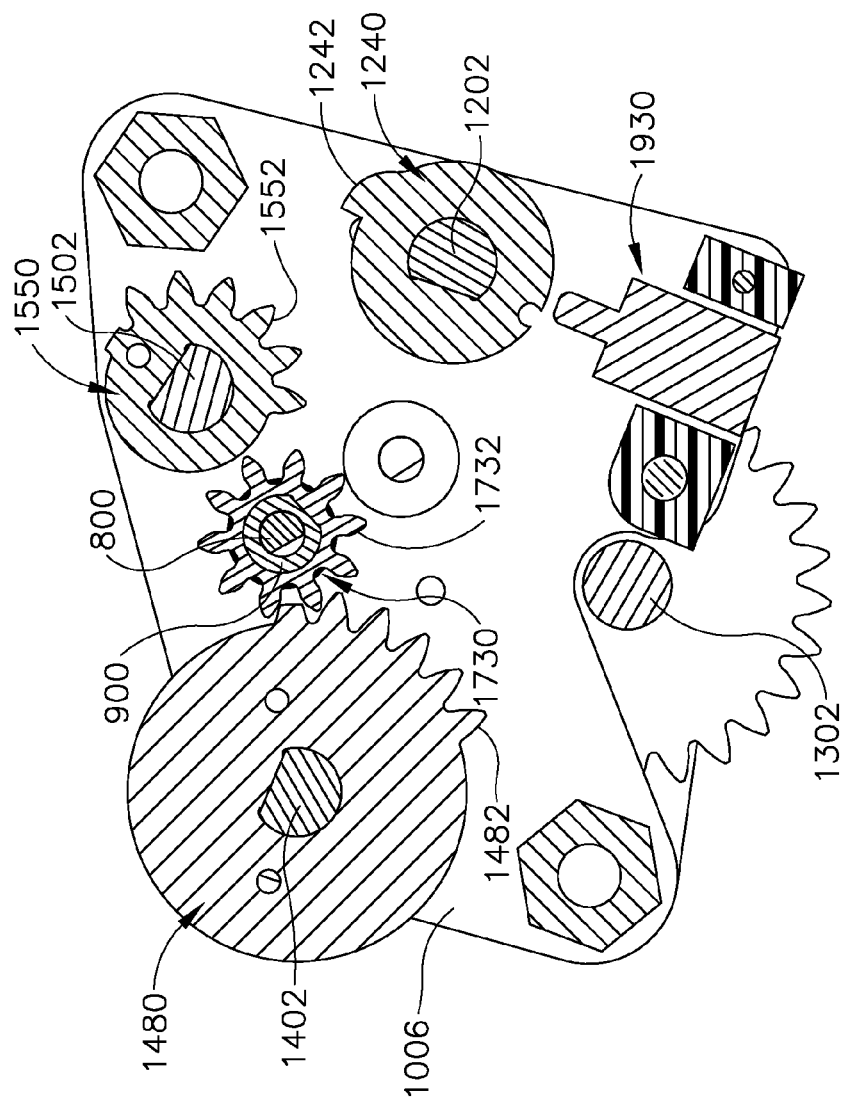
FIG. 49 depicts a cross-sectional view of the transmission assembly of FIG. 16, taken along line L-L of FIG. 19, with the transmission assembly at the fourth stage of operation.

As best seen in FIG. 47, protrusion (1462) of fourth rotary cam (1460) continues to engage second arcuate recess (1634) of second rotary cam (1630), thereby continuing to hold the rotational position of shaft assembly (1600) (including output shaft (800)). As shown in FIG. 48, fourth rotary cam (1470) has moved out of engagement with arcuate recess (1722) of second rotary cam (1720), such that fourth rotary cam (1470) no longer holds the rotational position of shaft assembly (1700). In addition, second sector gear (1480) has been rotated such that teeth (1482) of second sector gear (1480) are now positioned to engage teeth (1732) of spur gear (1730); such that subsequent rotation of shaft assembly (1400) will rotate shaft assembly (1700) (including output shaft (900)).

Figure 50:
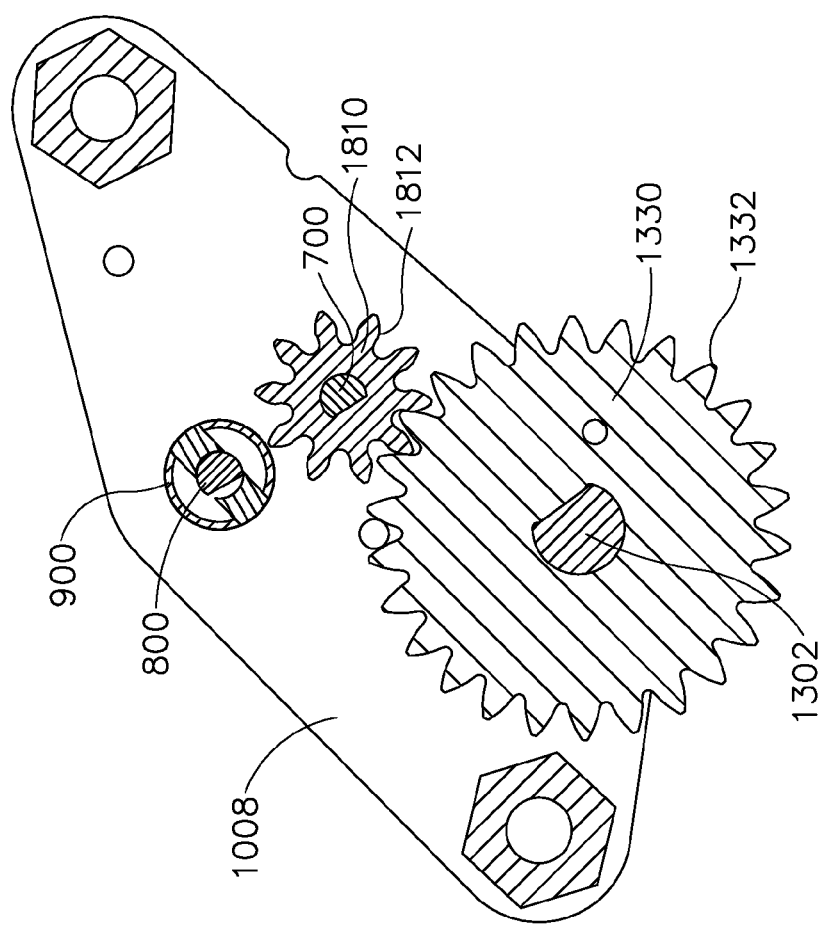
FIG. 50 depicts a cross-sectional view of the transmission assembly of FIG. 16, taken along line M-M of FIG. 19, with the transmission assembly at the fourth stage of operation.

As best seen by comparing FIG. 20M with FIG. 50, counterclockwise rotation of shaft assembly (1300) has caused shaft assembly (1800) (including output shaft (700)) to rotate clockwise due to engagement between teeth (1332) of spur gear (1330) and teeth (1812) of spur gear (1810). As noted above output shaft (700) and drive shaft (244) rotate together unitarily; while hollow shaft (240) is always held stationary throughout operation of suturing instrument (10) due to engagement between a boss of handle portion (20) and a notch (484) formed in the proximal end of hollow shaft (240). It should be understood that the above-described rotation of output shaft (700) (and drive shaft (244)) relative to handle portion (20) (and hollow shaft (240)) will cause opposing translation of jaws (220, 230) to release needle (50). It should also be understood that the rotational position of output shafts (800, 900) has been held during the transition of transmission assembly (1000) from the configuration shown in FIGS. 32-42 to the configuration shown in FIGS. 43-50. It should therefore be understood that jaws (260, 270) of arm (250) still maintain a firm grasp of needle during this transition, such that full control of needle (250) is transitioned from arm (210) to arm (250) at this stage.

Figure 51:
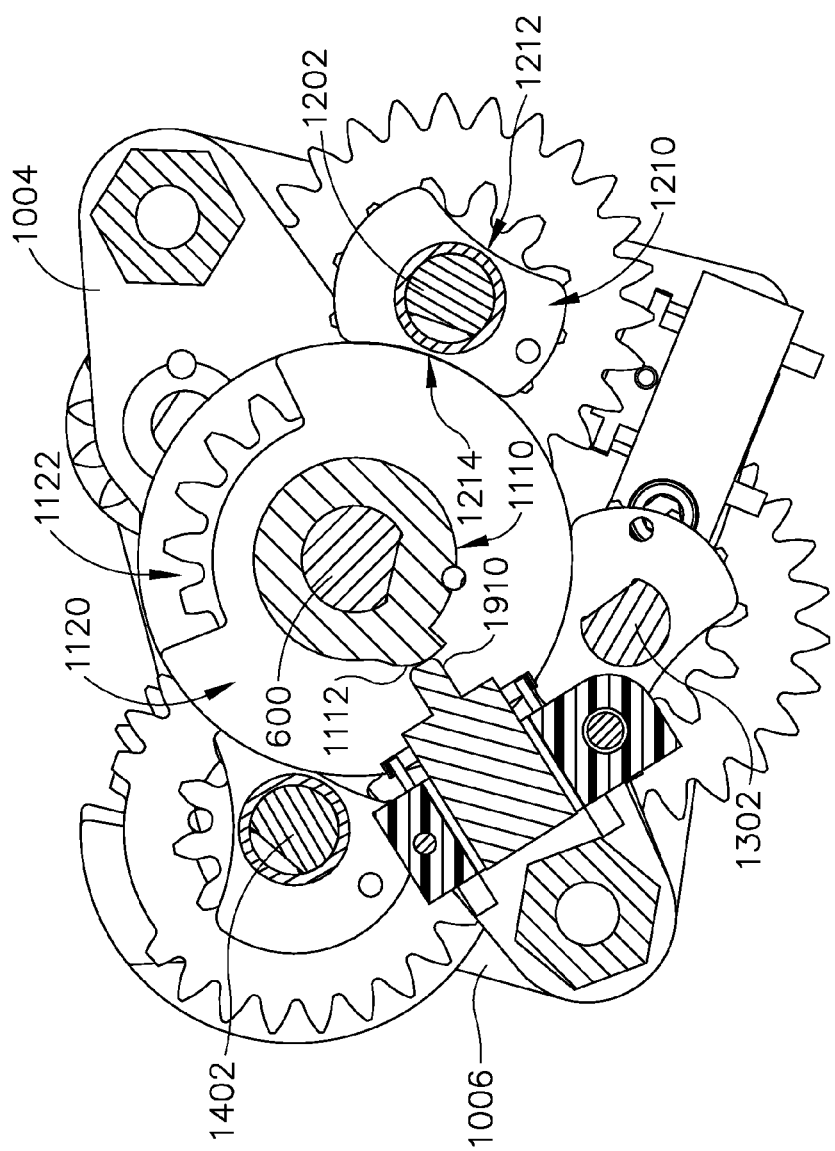
FIG. 51 depicts a cross-sectional view of the transmission assembly of FIG. 16, taken along line A-A of FIG. 19, with the transmission assembly at a fifth stage of operation.

5. Pulling Needle and Suture Through Tissue, and Pulling End Effector Away from Tissue With control of needle (50) being fully transferred from arm (210) to arm (250), arm (250) is rotated about axis (140) to pull suture (60) and the remainder of needle (50) through tissue (300, 302) as shown in FIG. 8D. The components of transmission assembly (1000) are actuated from the configuration shown in FIGS. 43-50 to the configuration shown in FIGS. 51-56 to provide this motion of arm (250). As shown in FIG. 51, second rotary cam (1120) of shaft assembly (1100) continues to engage first arcuate recess (1214) of first rotary cam (1210), thereby continuing to hold shaft assembly (1200) stationary throughout this transition. As also shown in FIG. 51, protrusion (1112) of first rotary cam (1110) engages limit switch (1910) upon reaching this stage, thereby sending a signal to a control module indicating that end effector (200) has reached the configuration and position shown in FIG. 8D. This may trigger a variety of responses. For instance, this may automatically stop motor (28) to stop rotation of components of transmission assembly (1000), requiring the surgeon to engage rocker (24) or release and re-engage rocker (24) to continue operation of suturing instrument (10). In addition or in the alternative, triggering of limit switch (1910) may provide a form of audio feedback (e.g., beep or other audible tone, etc.) and/or visual feedback (e.g., illumination or blinking of an LED, etc.) to the surgeon indicating that end effector (200) has reached this operational stage. Other suitable responses that may be triggered by activation of limit switch (1910) will be apparent to those of ordinary skill in the art in view of the teachings herein.

Figure 52:
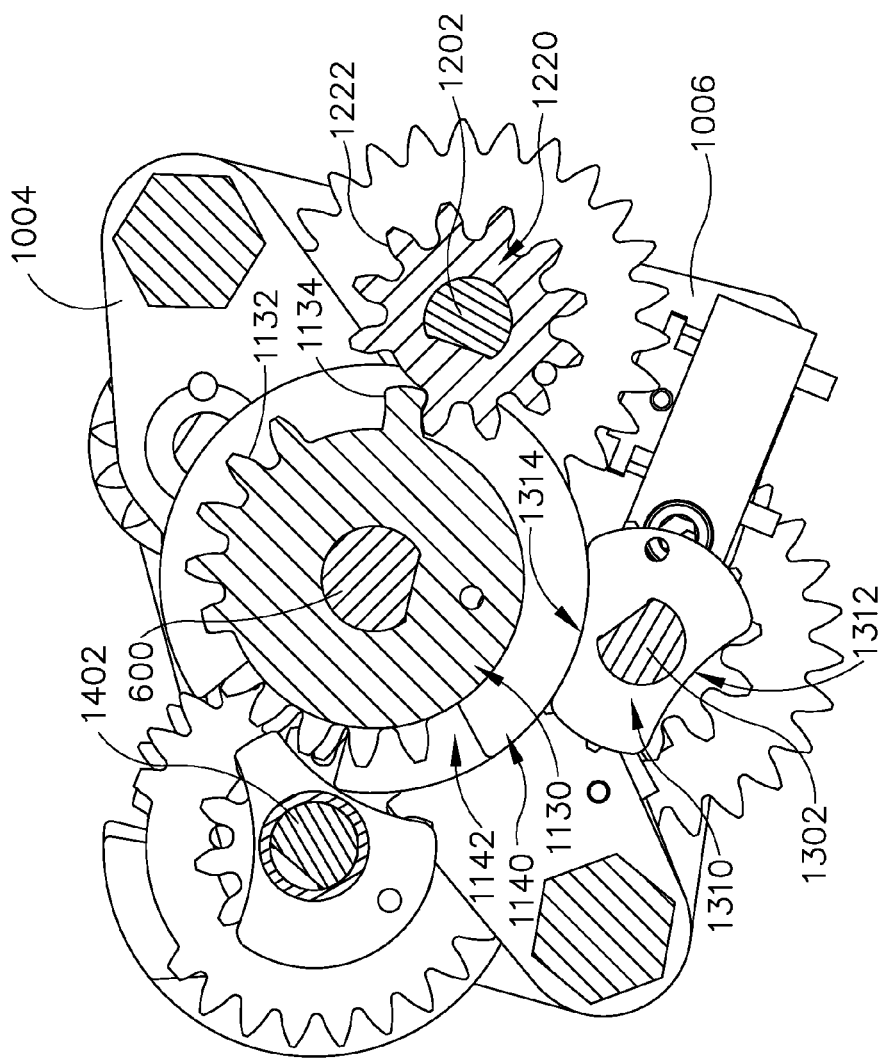
FIG. 52 depicts a cross-sectional view of the transmission assembly of FIG. 16, taken along line B-B of FIG. 19, with the transmission assembly at the fifth stage of operation.

As shown in FIG. 52, first sector gear (1130) has been rotated to a position where tooth (1134) makes initial contact with teeth (1222) of sector gear (1220), such that subsequent rotation of first sector gear (1130) will rotate sector gear (1220) and the rest of shaft assembly (1200). As also shown in FIG. 52, third rotary cam (1140) continues to hold rotary cam (1310) and the rest of shaft assembly (1300) at this stage. Thus, jaws (220, 230) of arm (210) remain open through this stage.

Figure 53:
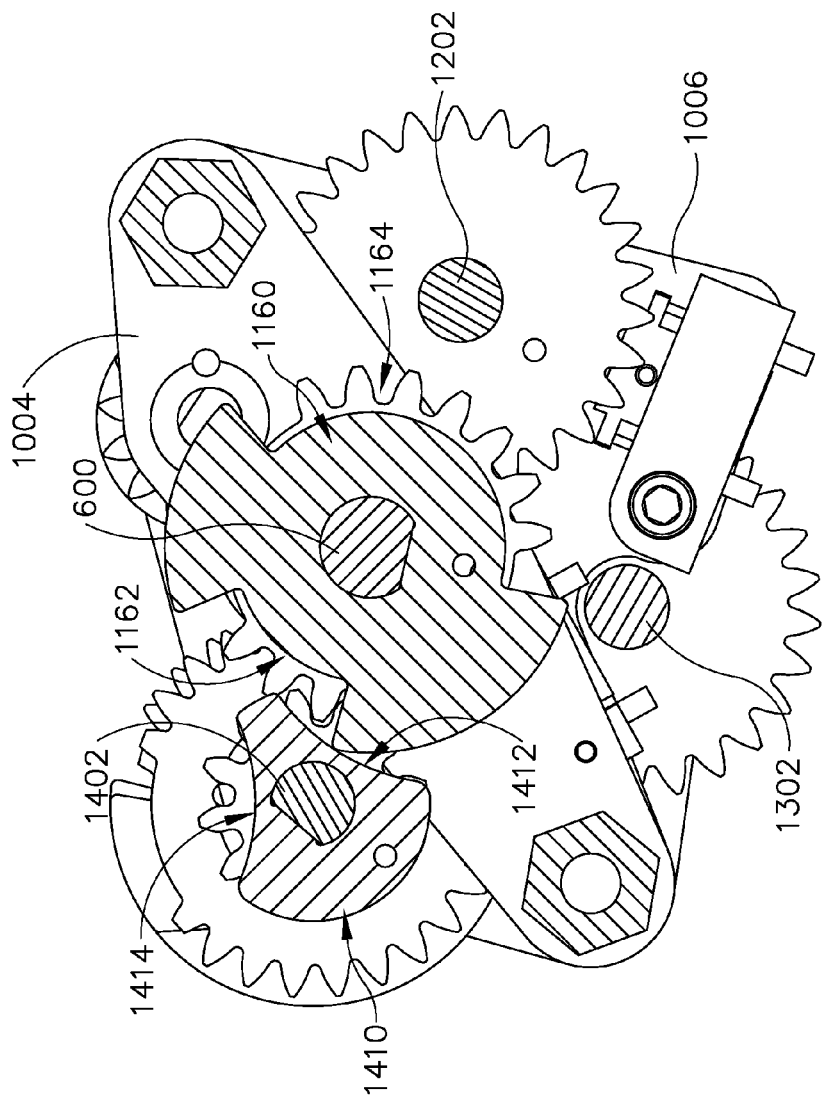
FIG. 53 depicts a cross-sectional view of the transmission assembly of FIG. 16, taken along line D-D of FIG. 19, with the transmission assembly at the fifth stage of operation.
Figure 54:
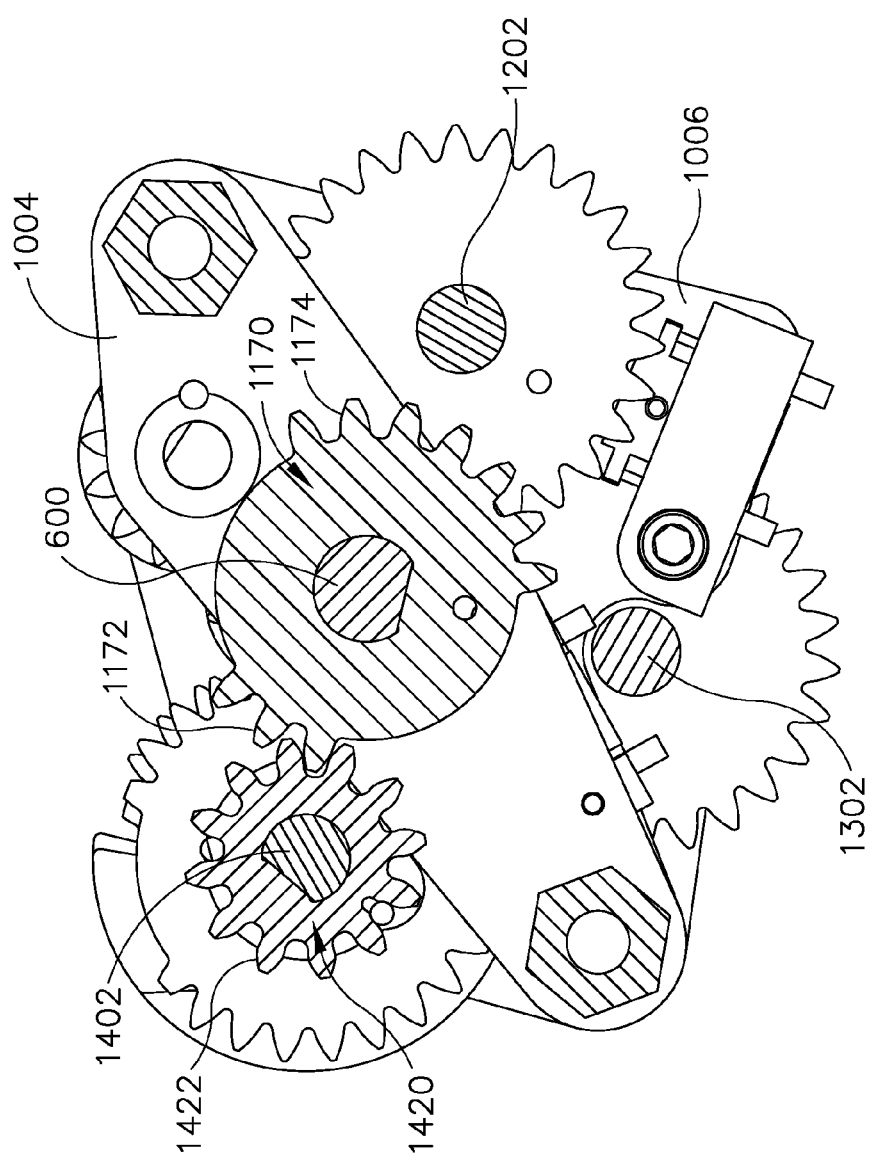
FIG. 54 depicts a cross-sectional view of the transmission assembly of FIG. 16, taken along line E-E of FIG. 19, with the transmission assembly at the fifth stage of operation.
Figure 55:
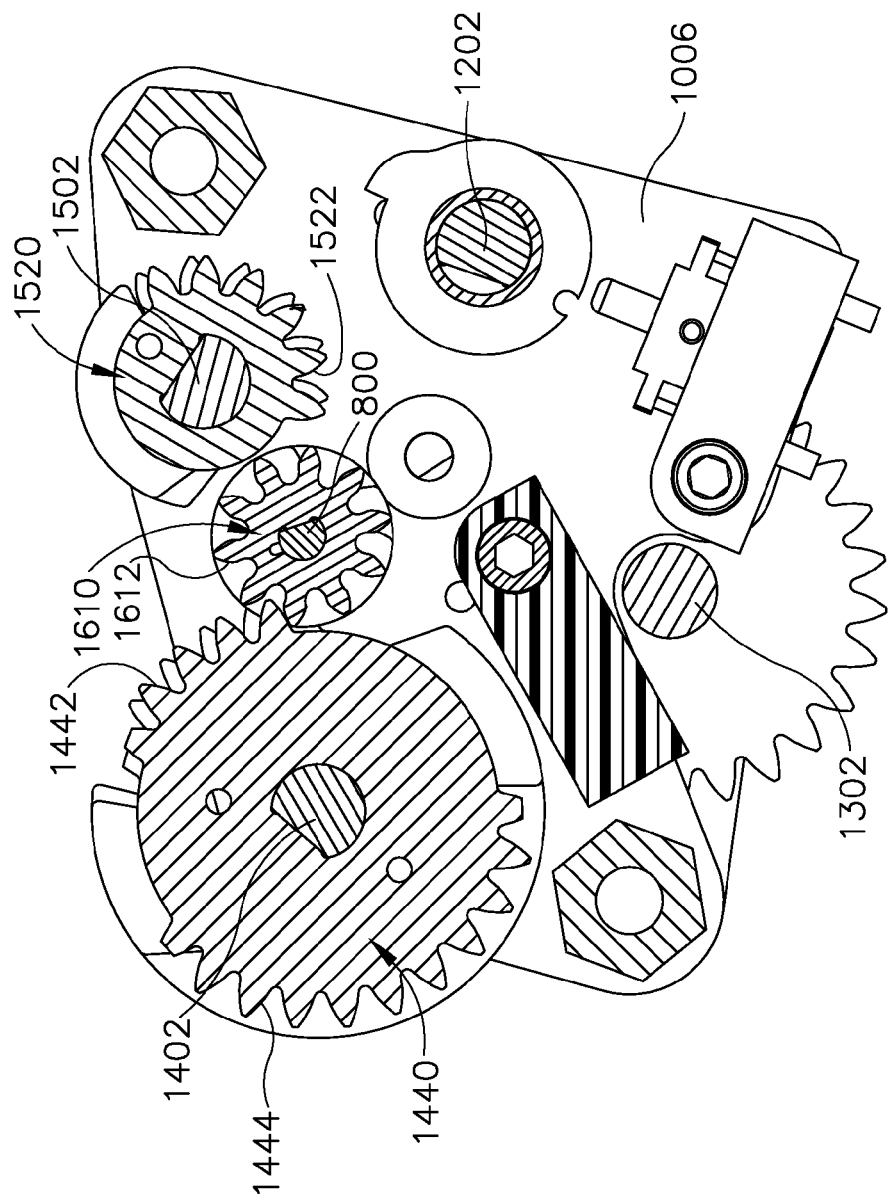
FIG. 55 depicts a cross-sectional view of the transmission assembly of FIG. 16, taken along line G-G of FIG. 19, with the transmission assembly at the fifth stage of operation.
Figure 56:
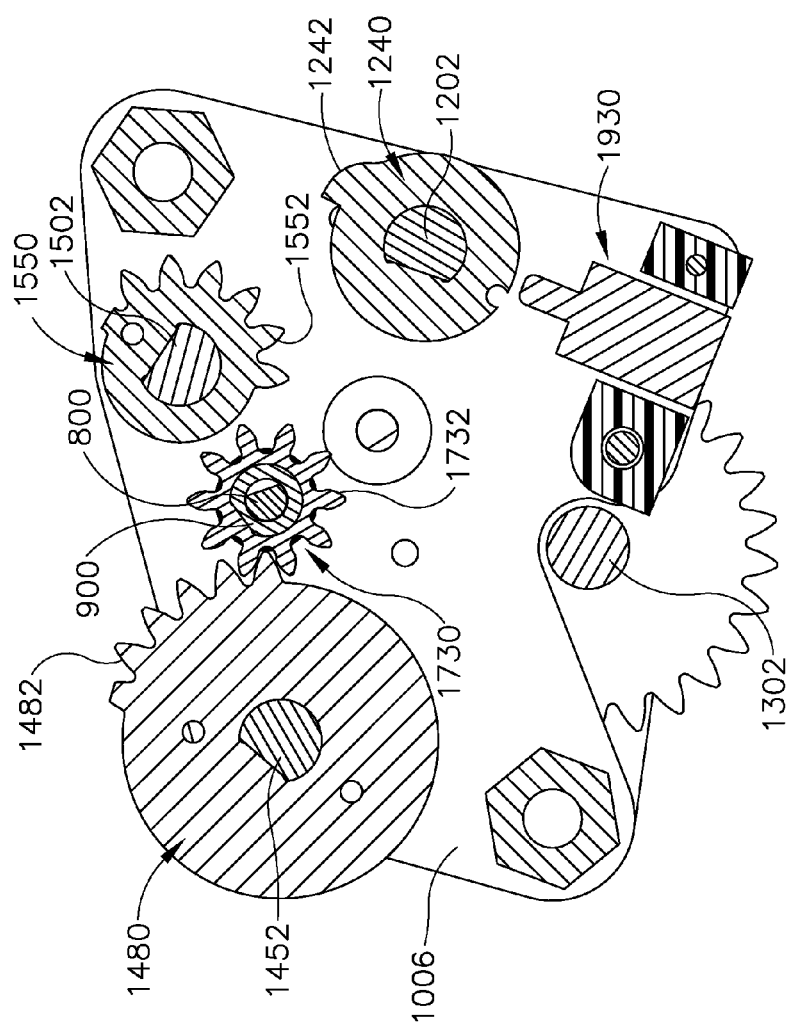
FIG. 56 depicts a cross-sectional view of the transmission assembly of FIG. 16, taken along line L-L of FIG. 19, with the transmission assembly at the fifth stage of operation.

As best seen by comparing FIG. 45 with FIG. 53, first recessed region (1162) of fourth rotary cam (1160) has provided clearance for counterclockwise rotation of first rotary cam (1410) and the rest of shaft assembly (1400). As best seen by comparing FIG. 46 with FIG. 54, this counterclockwise rotation of first rotary cam (1410) and the rest of shaft assembly (1400) is provided through engagement between teeth (1172) of sector gear (1170) and teeth (1422) of spur gear (1420). As shown in FIG. 55, this counterclockwise rotation of shaft assembly (1400) has caused clockwise rotation of shaft assembly (1600) (including output shaft (800)) through engagement between teeth (1442) of sector gear (1440) and teeth (1612) of spur gear (1600). As shown in FIG. 56, the counterclockwise rotation of shaft assembly (1400) has also caused clockwise rotation of shaft assembly (1700) (including output shaft (900)) through engagement between teeth (1482) of sector gear (1480) and teeth (1732) of spur gear (1730). It should be understood from the foregoing that both output shafts (800, 900) have rotated clockwise during the transition of end effector (200) from the configuration shown in FIG. 8C to the configuration shown in FIG. 8D. This clockwise rotation of output shafts (800, 900) is synchronized at the same rate of rotation. Thus, the synchronized rotation of output shafts (800, 900) provides rotation of the entire grasping arm (250) about axis (140); while still keeping jaws (260, 270) consistently closed during this movement.

Next, the surgeon pulls the entire end effector (200) away from tissue layers (300, 302), along a path that is substantially transverse to axis (130), as shown in FIG. 8E. The components of transmission assembly (1000) remain in the configuration shown in FIGS. 51-56 during this stage. In other words, motor (28) stays inactive and jaws (260, 270) are positively held closed while jaws (220, 230) are held open.

6. Positioning Needle Receiving Arm for Receipt of Needle by Needle Driving Arm

With end effector (200) positioned sufficiently away from tissue layers (300, 302), second grasping arm (250) is rotated about axis (140) to the position shown in FIG. 8F. The components of transmission assembly (1000) are actuated from the configuration shown in FIGS. 51-56 back to the configuration shown in FIGS. 43-50 to provide this motion of arm (250). It should be understood that the motion of motor (28) is reversed to rotate input shaft (600) in a direction opposite to the direction of rotation associated with the transition from FIG. 8C to FIG. 8D described above. With this providing rotation of the components of transmission assembly (1000) in the opposite direction, the driving interactions within transmission assembly (1000) are reversed while the holding interactions within transmission assembly (1000) are the same as those described above with respect to the transition from FIG. 8C to FIG. 8D (and the corresponding transition from FIGS. 43-50 to FIGS. 51-56).

7. Grasping Needle with Needle Driving Arm

With arms (210, 250) still in the position shown in FIG. 8F, the components of transmission assembly (1000) are actuated from the configuration shown in FIGS. 43-50 to the configuration shown in FIGS. 32-42 to grasp needle (50) with jaws (220, 230) of arm (210). It should be understood that the motion of motor (28) continues to be reversed to rotate input shaft (600) in a direction opposite to the direction of rotation associated with the transition from FIGS. 32-42 to FIGS. 43-50 described above. Thus, with this providing rotation of the components of transmission assembly (1000) in the opposite direction, the driving interactions within transmission assembly (1000) are reversed while the holding interactions within transmission assembly (1000) are the same as those described above with respect to the transition from FIGS. 32-42 to FIGS. 43-50 described above. It should be understood that jaws (260, 270) of arm (250) still maintain a firm grasp of needle during this stage.

8. Releasing Needle from Needle Receiving Arm

Still referring to FIG. 8F, once needle (80) is grasped with jaws (220, 230) of arm (210), the components of transmission assembly (1000) are actuated from the configuration shown in FIGS. 32-42 to the configuration shown in FIGS. 21-31 to release needle (50) from jaws (260, 270) of arm (250). It should be understood that the motion of motor (28) continues to be reversed to rotate input shaft (600) in a direction opposite to the direction of rotation associated with the transition from FIGS. 21-31 to FIGS. 32-42 described above. Thus, with this providing rotation of the components of transmission assembly (1000) in the opposite direction, the driving interactions within transmission assembly (1000) are reversed while the holding interactions within transmission assembly (1000) are the same as those described above with respect to the transition from FIGS. 21-31 to FIGS. 32-42 described above.

9. Moving Needle Receiving Arm to Expose Sharp Tip of Needle

With control of needle (50) being fully transferred from arm (250) to arm (210), arm (250) is rotated about axis (140) to expose sharp tip (52) of needle (50) as shown in FIG. 8G. The components of transmission assembly (1000) are actuated from the configuration shown in FIGS. 21-31 back to the configuration shown in FIGS. 20A-20M to provide this motion of arm (250). It should be understood that the motion of motor (28) continues to be reversed to rotate input shaft (600) in a direction opposite to the direction of rotation associated with the transition from FIG. 8B to FIG. 8C described above. With this providing rotation of the components of transmission assembly (1000) in the opposite direction, the driving interactions within transmission assembly (1000) are reversed while the holding interactions within transmission assembly (1000) are the same as those described above with respect to the transition from FIG. 8B to FIG. 8C (and the corresponding transition from FIGS. 20A-20M to FIGS. 21-31).

It should also be understood that, upon reaching the configuration shown in FIG. 8G, protrusion (1242) of second rotary cam (1240), engages limit switch (1930), indicating that end effector (200) has reached the configuration and position shown in FIG. 8D. This may trigger a variety of responses. For instance, this may automatically stop motor (28) to stop rotation of components of transmission assembly (1000), requiring the surgeon to engage rocker (24) or release and re-engage rocker (24) to continue operation of suturing instrument (10). In addition or in the alternative, triggering of limit switch (1930) may provide a form of audio feedback (e.g., beep or other audible tone, etc.) and/or visual feedback (e.g., illumination or blinking of an LED, etc.) to the surgeon indicating that end effector (200) has reached this operational stage. Other suitable responses that may be triggered by activation of limit switch (1930) will be apparent to those of ordinary skill in the art in view of the teachings herein.

10. Repositioning End Effector for Subsequent Stitches

Next, the surgeon rotates the entire instrument (10) about longitudinal axis (130) to position sharp tip (52) above tissue layers (300, 302), as shown in FIG. 8H. The components of transmission assembly (1000) remain in the configuration shown in FIGS. 20A-20M during this stage. Having reached the configuration shown in FIG. 8H, end effector (200) may be moved back toward tissue layers (300, 302), such as along a path transverse to axis (130), to again reach the position shown in FIG. 8A. The above described cycle may then be repeated as many times as desired until an appropriate number of stitches have been made through tissue layers (300, 302). The free end of suture (50) may then be knotted, clipped, or otherwise secured. Other suitable ways in which instrument (10) may be used and/or operable will be apparent to those of ordinary skill in the art in view of the teachings herein.

It should be understood from the foregoing that, at any given stage of operation of transmission assembly (1000), each shaft assembly (1100, 1200, 1300, 1400, 1500, 1600, 1700, 1800) is either being actively driven by a gear or is being positively held stationary through engagement between gears or cam features. At no stage of operation is any shaft assembly (1100, 1200, 1300, 1400, 1500, 1600, 1700, 1800) left free from engagement with any other shaft assembly (1100, 1200, 1300, 1400, 1500, 1600, 1700, 1800). Thus, movement of all shaft assemblies (1100, 1200, 1300, 1400, 1500, 1600, 1700, 1800) is precisely controlled in the present example, with transmission assembly (1000) lacking any form of "slop" or lost motion. However, some alternative versions may permit some degree of slop or lost motion, if desired.

While cam components are described above as being engaged by only one other component at only one surface at any given time, it should be understood that such cam components may be engaged by more than one component and/or at more than one surface at any given time. For instance, first rotary cam (1210) may be simultaneously engaged by one holding component at first arcuate recess (1212) and another holding component at second arcuate recess (1214). As another merely illustrative example, first rotary cam (1620) may have an additional scalloped/arcuate recess that is engaged by a holding component at the same time another holding component engages arcuate recess (1622). Similarly, in instances where the rotational position of a shaft assemblies (1100, 1200, 1300, 1400, 1500, 1600, 1700, 1800) is held by just one rotary cam at a given time, one or more additional rotary cams (and/or other features) may be provided to simultaneously further hold the rotational position of shaft assembly (1100, 1200, 1300, 1400, 1500, 1600, 1700, 1800). Other suitable variations and ways of implementing them will be apparent to those of ordinary skill in the art in view of the teachings herein.

VI. Miscellaneous

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
    (a) a shaft assembly having a proximal end, a distal end, and a longitudinal axis, the shaft assembly comprising:
        (i) an outer sheath,
        (ii) a first shaft pair extending through at least a portion of the outer sheath, the first shaft pair comprising:
            (A) a first outer drive shaft, and
            (B) a first inner drive shaft extending through at least a portion of the first outer drive shaft, wherein the first inner drive shaft is coaxial with the first outer drive shaft, wherein the first inner drive shaft comprises a first discrete threaded section and a second discrete threaded section, wherein the first and second discrete threaded sections of the first inner drive shaft are separate from each other on the first inner drive shaft such that rotating the first inner drive shaft simultaneously rotates the first and second discrete threaded sections thereon, and
        (iii) a second shaft pair extending parallel to the first shaft pair through at least a portion of the outer sheath, the second shaft pair shaft pair comprising:
            (A) a second outer drive shaft, and
            (B) a second inner drive shaft extending through at least a portion of the second outer drive shaft, wherein the second inner drive shaft is coaxial with the second outer drive shaft wherein the second inner drive shaft comprises a first discrete threaded section and a second discrete threaded section, wherein the first and second discrete threaded sections of the second inner drive shaft are separate from each other on the second inner drive shaft such that rotating the second inner drive shaft simultaneously rotates the first and second discrete threaded sections thereon; and (b) an end effector located at the distal end of the shaft assembly, wherein the end effector comprises:

(i) a first driven feature configured to actuate having a first drive feature and a second drive feature, wherein the first drive feature is operatively coupled with the first threaded section of the first inner drive shaft and the second drive feature is operatively coupled with the second threaded section of the first inner drive shaft, wherein the first and second threaded sections of the first inner drive shaft are configured to simultaneously engage the first and second drive features of the first driven feature when rotated and simultaneously move each of the first and second drive features such that the first driven feature actuates, and (ii) a second driven feature configured to actuate having a first drive feature and a second drive feature, wherein the first drive feature is operatively coupled with the first threaded section of the second inner drive shaft and the second drive feature is operatively coupled with the second threaded section of the second inner drive shaft, wherein the first and second threaded sections of the second inner drive shaft are configured to simultaneously engage the first and second drive features of the second driven feature when rotated and simultaneously move each of the first and second drive features such that the second driven feature actuates.

2. The apparatus of claim 1, wherein the first inner drive shaft comprises a beam section extending along part of the length of the first inner drive shaft, wherein the second inner drive shaft comprises a beam section extending along part of the length of the second inner drive shaft.

3. The apparatus of claim 1, wherein the shaft assembly and the end effector are dimensioned to fit through a surgical trocar.

4. The apparatus of claim 1, further comprising a handle assembly positioned at a proximal end of the shaft assembly, wherein the handle assembly is operable to selectively activate at least one of the shaft pairs.

5. The apparatus of claim 4, wherein the handle assembly further includes at least one motor in communication with at least one of the shaft pairs.

6. The apparatus of claim 1, wherein the first shaft pair is operable to rotate the first driven feature relative to the outer sheath.

7. The apparatus of claim 1, wherein the first driven feature comprises an arm having movable jaws, wherein the first shaft pair is operable to actuate the jaws of the arm.

8. The apparatus of claim 1, wherein the first threaded section of each of the first and second inner drive shafts has threading oriented with a first pitch, wherein the second threaded section of each of the first and second inner drive shafts has threading oriented with a second pitch, wherein the second pitch is opposite from the first pitch such that the first threaded section of each of the first and second inner drive shafts respectively moves each of the first drive features a first direction and the second threaded section of each of the first and second inner drive shaft respectively moves each of the second drive features a second direction, wherein the second direction is opposite the first direction for actuating the first and second driven features.

9. The apparatus of claim 8, wherein the first driven feature comprises an arm having a first jaw and a second jaw, wherein the first and second jaws respectively comprise the first and second drive features in the form of first and second linear drive features, wherein the first linear drive feature comprises a threading meshing with the threading of the first threaded section of the first inner drive shaft, wherein the second linear drive feature comprises a threading meshing with the threading of the second threaded section of the first inner drive shaft, and wherein the first linear drive feature is configured to move linearly in the first direction and the second linear drive feature is configured to move linearly in the opposite second direction such that the first jaw moves linearly in the first direction and the second jaw moves linearly in the opposite second direction for at least one of opening and closing the first and second jaws.

10. The apparatus of claim 1, wherein at least one of the outer drive shafts comprise one or more torsional cutouts.

11. The apparatus of claim 1, wherein the first driven feature comprises a first arm extending along a first arm axis, wherein the first arm axis is offset from the longitudinal axis of the shaft assembly.

12. The apparatus of claim 11, wherein the first arm axis is coaxial with the first outer drive shaft and the first inner drive shaft.

13. The apparatus of claim 11, wherein the first arm further includes a dogleg feature, wherein the dogleg feature is positioned between a distal portion of the first arm and a proximal portion of the first arm, wherein the proximal portion of the first arm extends along the first arm axis, wherein the distal portion of the first arm extends along an axis that is parallel to yet offset from the first arm axis.

14. The apparatus of claim 1, wherein the second driven feature comprises a second arm extending along a second arm axis, wherein the second arm axis is coaxial with the second outer drive shaft and the second inner drive shaft.

15. The apparatus of claim 1, further comprising one or more spacer bushings, wherein each spacer bushing defines a pair of apertures, wherein the first outer drive shaft is disposed in one of the apertures, wherein the second outer drive shaft is disposed in another of the apertures such that the one or more spacer bushings are configured to maintain the parallel relationship between the first and second shaft pairs.

16. An apparatus, comprising:

(a) a shaft assembly having a proximal end, a distal end, and a longitudinal axis, the shaft assembly comprising:

(i) an outer sheath, (ii) a first shaft pair extending along a first longitudinal axis through at least a portion of the outer sheath, the first shaft pair comprising:

(A) a first outer drive shaft, and (B) a first inner drive shaft extending through at least a portion of the first outer drive shaft, wherein the first inner drive shaft is coaxial with the first outer drive shaft, and (iii) a second shaft pair extending along a second longitudinal axis parallel to the first longitudinal axis through at least a portion of the outer sheath, the second shaft pair shaft pair comprising:

(A) a second outer drive shaft, and (B) a second inner drive shaft extending through at least a portion of the second outer drive shaft, wherein the second inner drive shaft is coaxial with the second outer drive shaft; and (b) an end effector located at the distal end of the shaft assembly, wherein the end effector comprises:

(i) a first jaw pair, wherein the first shaft pair is operable to actuate each of the jaws of the first jaw pair simultaneously in opposite linear directions relative to the first inner drive shaft along a first path that is parallel to the first longitudinal axis, and (ii) a second jaw pair, wherein the second shaft pair is operable to actuate each of the jaws of the second jaw pair simultaneously in opposite linear directions relative to the second inner drive shaft along a second path that is parallel to the second longitudinal axis.

17. The apparatus of claim 16, wherein the first jaw pair and the second jaw pair are operable to selectively grasp and release a suture needle.

18. The apparatus of claim 16, wherein the shaft assembly further comprises a distal cap, wherein the distal cap defines a first aperture and a second aperture, wherein the first aperture comprises a pair of opposing keyways, wherein the second aperture comprises a first inner wall and a second outer wall, and wherein the second outer wall defines an arcuate keyway.

19. The apparatus of claim 18, wherein the first inner drive shaft comprises a first pair of fins, wherein the second inner drive shaft comprises a second pair of fins, wherein the pair of opposing keyways in the first aperture are sized to receive the first pair of pins, and wherein the arcuate keyway is configured to receive one fin of the second pair of fins.

20. An apparatus, comprising:
(a) a shaft assembly having a proximal end, a distal end, and a longitudinal axis, the shaft assembly comprising:
(i) an outer sheath,
(ii) a first shaft pair extending through at least a portion of the outer sheath, the first shaft pair having a first portion configured to rotate and a second portion configured to translate, wherein the first portion directly engages the second portion such that rotation of the first portion of the first shaft pair is configured to translate the second portion of the first shaft pair, and
(iii) a second shaft pair extending parallel to the first shaft pair through at least a portion of the outer sheath, the second shaft pair having a first portion configured to rotate and a second portion configured to translate, wherein the first portion directly engages the second portion such that rotation of the first portion of the second shaft pair is configured to translate the second portion of the second shaft pair; and (b) an end effector located at the distal end of the shaft assembly, wherein the end effector comprises:
(i) a first jaw pair connected to the translatable second portion of the first shaft pair, the first jaw pair having a first jaw and a second jaw, wherein the first shaft pair is operable to actuate the first jaw pair, wherein the first jaw and the second jaw of the first jaw pair are operable to translate with opposing translational motions relative to the rotatable first portion of the first shaft pair by converting rotational motion of the first portion of the first shaft pair into opposing translational motions of the second portion of the first shaft pair, and
(ii) a second jaw pair connected to the translatable second portion of the second shaft pair, the second jaw pair having a first jaw and a second jaw, wherein the second shaft pair is operable to actuate the second jaw pair, wherein the first jaw and the second jaw of the second jaw pair are operable to translate with opposing translational motions relative to the rotatable first portion of the second shaft pair by converting rotational motion of the first portion of the second shaft pair into opposing translational motions of the second portion of the second shaft pair, wherein the first and second jaw pairs are operable to selectively grasp and release a suture needle.

* * * * *